United States Patent
Fikes et al.

(10) Patent No.: US 8,007,810 B2
(45) Date of Patent: Aug. 30, 2011

(54) HLA-A2 TUMOR ASSOCIATED ANTIGEN PEPTIDES AND COMPOSITIONS

(75) Inventors: John D. Fikes, San Diego, CA (US); Glenn Ishioka, San Diego, CA (US); Alessandro Sette, La Jolla, CA (US); Robert W. Chesnut, Cardiff-by-the-Sea, CA (US)

(73) Assignee: Biotech Synergy, Inc., La Jolla, CA (US)

( * ) Notice: Subject to any disclaimer, the term of this patent is extended or adjusted under 35 U.S.C. 154(b) by 0 days.

(21) Appl. No.: 12/710,836

(22) Filed: Feb. 23, 2010

(65) Prior Publication Data

US 2010/0209493 A1    Aug. 19, 2010

Related U.S. Application Data

(63) Continuation of application No. 10/553,703, filed as application No. PCT/US2004/011895 on Apr. 16, 2004, now abandoned.

(60) Provisional application No. 60/463,724, filed on Apr. 18, 2003.

(51) Int. Cl.
| | |
|---|---|
| A61K 39/00 | (2006.01) |
| A61K 38/17 | (2006.01) |
| A61K 9/127 | (2006.01) |
| A61P 35/00 | (2006.01) |
| C07K 35/00 | (2006.01) |

(52) U.S. Cl. .................. 424/185.1; 424/277.1; 530/300
(58) Field of Classification Search .................. None
See application file for complete search history.

(56) References Cited

OTHER PUBLICATIONS

Marchland et al (European Journal of Cancer, 2003, vol. 39, pp. 70-77).*

* cited by examiner

*Primary Examiner* — Karen Canella
(74) *Attorney, Agent, or Firm* — Adriano & Associates

(57) ABSTRACT

A peptide or composition comprising at least one HLA-A2 epitope or analog from CEA, HER2/neu, MAGE2, MAGE3, or p53.

11 Claims, 4 Drawing Sheets

Figure 1:
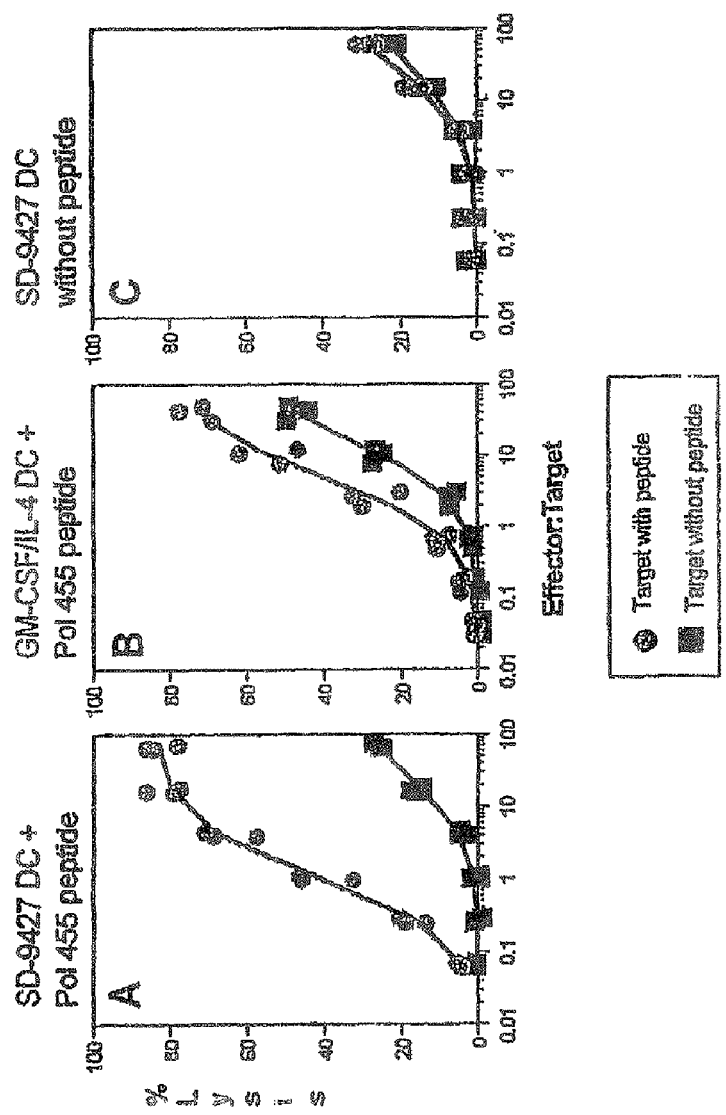

Splenic DC from ProGP-Treated Mice Induce CTL Responses *In Vivo*

Schematic of Dendritic Cell Pulsing and Testing for a Cellular Vaccine Embodiment

HLA-A2 TUMOR ASSOCIATED ANTIGEN PEPTIDES AND COMPOSITIONS

CROSS-REFERENCE TO RELATED APPLICATIONS

This application is a continuation of U.S. patent application Ser. No. 10/553,703, filed Apr. 16, 2004, which is a U.S. national phase of International Appl. No. PCT/US2004/011895, filed Apr. 16, 2004, said PCT/US2004/011895 claims the benefit of U.S. Provisional Appl. No. 60/463,724, filed Apr. 18, 2003, all of which are herein incorporated by reference.

BACKGROUND OF THE INVENTION

1. Field of the Invention

This invention relates to the field of biology. In a particular embodiment, it relates to peptides, polynucleotides, and compositions useful to monitor or elicit an immune response to selected tumor-associated antigens.

2. Related Art

The field of immunotherapy is yielding new approaches for the treatment of, cancer, including the development of improved cancer vaccines (Krul, K. G., *Decision Resources*, 10.1-10.25 (1998)). While vaccines provide a mechanism of directing immune responses towards the tumor cells, there are a number of mechanisms by which tumor cells circumvent immunological processes (Pardoll, D. M., *Nature Medicine* (Vaccine Supplement), 4:525-531 (1998)). Recent advances indicate that the efficacy of peptide vaccines may be increased when combined with approaches which enhance the stimulation of immune responses, such as the use of Interleukin-2 or autologous dendritic cells (DC) (Abbas et al., eds., *Cellular and Molecular Immunology*, 3$^{rd}$ Edition, W. B. Saunders Company, pub. (1997)).

In a Phase I study, Murphy, et al., demonstrated that Human Leukocyte Antigen (HLA)-A2-binding peptides corresponding to sequences present in prostate specific antigen (PSA) stimulated specific cytotoxic T-cell lymphocyte (CTL) responses in patients with prostate cancer (Murphy et al., *The Prostate* 29:371-380 (1996)). Rosenberg, et al., evaluated the safety and mechanism of action of a synthetic HLA-A2 binding peptide derived from the melanoma associated antigen, gp100, as a cancer vaccine to treat patients with metastatic melanoma (Rosenberg et al., *Nature Med.*, 4:321-327 (1998)). Based on immunological assays, 91% of patients were successfully immunized with the synthetic peptide. In addition, 42% (13/31) of patients who received the peptide vaccine in combination with IL-2 treatment, demonstrated objective cancer responses. In addition, Nestle, et al., reported the vaccination of 16 melanoma patients with peptide- or tumor lysate-pulsed DC (Nestle et al., *Nature Med* 4:328-332 (1998)). Peptide-pulsed DC induced immune responses in 11/12 patients immunized with a vaccine comprised of 1-2 peptides. Objective responses were evident in 5/16 (3 peptide-pulsed, 2 tumor-lysate pulsed) patients evaluated in this study. These Phase I safety studies provided evidence that HLA-A2 binding peptides of known tumor-associated antigens demonstrate the expected mechanism of action. These vaccines were generally safe and well tolerated. Vaccine molecules related to at leaset four cancer antigens, CEA, HER2/neu, MAGE2, and, MAGE3 have been disclosed. (Kawashima et al., *Human Immunology*, 59:1-14 (1998))

Preclinical studies have shown that vaccine-pulsed DC mediate anti-tumor effects through the stimulation of anti-gen-specific CTL (Mandelboim et al., *Nature Med.*, 1: 1179-1183 (1995); Celluzzi et al., *J Exp Med* 183:283-287 (1996); Zitvogel et al., *J Exp Med* 183:87-97 (1996); Mayordomo et al., *Nature Med* 1:1297-1302 (1995)). CTL directly lyse tumor cells and also secrete an array of cytokines such as interferon gamma (IFNγ), tumor necrosis factor (TNF) and granulocyte-macrophage colony stimulating factor (GM-CSF), that further amplify the immune reactivity against the tumor cells. CTL recognize tumor associated antigens (TAA) in the form of a complex composed of 8-11 amino acid residue peptide epitopes, bound to Major Histocompatibility Complex (MHC) molecules (Schwartz, B. D., *The human major histocompatibility complex HLA in basic & clinical immunology* Stites et al., eds., Lange Medical Publication: Los Altos, pp. 52-64, 4$^{th}$ ed.). Peptide epitopes are generated through intracellular processing of proteins. The processed peptides bind to newly synthesized MHC molecules and the epitope-MHC complexes are expressed on the cell surface. These epitope-MHC complexes are recognized by the T cell receptor of the CTL. This recognition event is required for the activation of CTL as well as induction of the effector functions such as lysis of the target tumor cell.

MHC molecules are highly polymorphic proteins that regulate T cell responses (Schwartz, B. D., *The human major histocompatibility complex HLA in basic & clinical immunology* Stites et al., eds., Lange Medical Publication: Los Altos, pp. 52-64, 4$^{th}$ ed.). The species-specific MHC homologues that display CTL epitopes in humans are termed human leukocyte antigen ("HLA"). HLA class I molecules can be divided into several families or "supertypes" based upon their ability to bind similar repertoires of peptides. Vaccines which bind to multiple HLA supertypes, such as for example A2, A3, and B7, will afford broad, non-ethnically biased population coverage. As seen in Table 1, population coverage is approximately 84-90% for various ethnicities, with an average coverage of the sample ethnicities at approximately 87%.

One of the main factors contributing to the dynamic interplay between host and disease is the immune response mounted against the pathogen, infected cell, or malignant cell. In many conditions such immune responses control the disease. Several animal model systems and prospective studies of natural infection in humans suggest that immune responses against a pathogen can control the pathogen, prevent progression to severe disease and/or eliminate the pathogen. A common theme is the requirement for a multispecific T cell response, and that narrowly focused responses appear to be less effective.

In the cancer setting there are several findings that indicate that immune responses can impact neoplastic growth:

First, the demonstration in many different animal models, that anti-tumor T cells, restricted by MHC class I, can prevent or treat tumors.

Second, encouraging results have come from immunotherapy trials.

Third, observations made in the course of natural disease correlated the type and composition of T cell infiltrate within tumors with positive clinical outcomes (Coulie P G, et al. Antitumor immunity at work in a melanoma patient In *Advances in Cancer Research*, 213-242, 1999).

Moreover, tumors commonly have the ability to mutate, thereby changing their immunological recognition. For example, the presence of monospecific CTL was also correlated with control of tumor growth, until antigen loss emerged (Riker A, et al., Immune selection after antigen-specific immunotherapy of melanoma *Surgery*, August: 126(2):112-20, 1999; Marchand M, et al., Tumor regressions were observed in patients with metastatic melanoma treated with an antigenic peptide derived from the MAGE-3 gene and presented by HLA-A1 *Int. J. Cancer* 80(2):219-30, Jan. 18, 1999). Similarly, loss of beta 2 microglobulin was detected in 5/13 lines established from melanoma patients after receiving immunotherapy at the National Cancer Institute (Restifo N P, et al., Loss of functional Beta2-microglobulin in metastatic melanomas from five patients receiving immunotherapy *Journal of the National Cancer Institute*, Vol. 88 (2), 100-108, January 1996). It has long been recognized that HLA class I is frequently altered in various tumor types. This deservation has led to a hypothesis that this phenomenon might reflect immune pressure exerted on the tumor by means of class I restricted CTL. The extent and degree of alteration in HLA class I expression appears to be reflective of past immune pressures, and may also have prognostic value (van Duinen S G, et al., Level of HLA antigens in locoregional metastases and clinical course of the disease in patients with melanoma *Cancer Research* 48, 1019-1025, February 1988; Möller P, et ed., Influence of major histocompatibility complex class I and II antigens on survival in colorectal carcinoma *Cancer Research* 51, 729-736, January 1991). Taken together, these observations provide a rationale for immunotherapy of cancer and infectious disease, and suggest effective strategies that are needed to counteract the complex series of pathological changes associated with disease.

The frequency of alterations in class I expression is the subject of numerous studies (Algarra I, et al., The HLA crossroad in tumor immunology *Human Immunology* 61, 65-73, 2000). Rees and Mian estimate allelic loss to occur overall in 3-20% of tumors, and allelic deletion to occur in 15-50% of tumors. It should be noted that each cell carries two separate sets of class I genes, each gene carrying one HLA-A and one HLA-B locus. Thus, fully heterozygous individuals carry two different HLA-A molecules and two different HLA-B molecules. Accordingly, the actual frequency of losses for any specific allele could be as little as one quarter of the overall frequency. They also note that, in general, a gradient of expression exists between normal cells, primary tumors and metastatic tumors. In a study from Natali and coworkers (Natali P G, et al., Selective changes in expression of HLA class I polymorphic determinants in human solid tumors *PNAS USA* 86:6719-6723, September 1989), solid tumors were investigated for total HLA expression, using the W6/32 antibody, and for allele-specific expression of the A2 antigen, as evaluated by use of the BB7.2-antibody. Tumor samples were derived from primary or metastatic tumors, for 13 different tumor types, and scored as "negative" if less than 20%, "reduced" if in the 30-80% range, and "normal" above 80%. All tumors, both primary and metastatic, were HLA positive with W6/32. In terms of A2 expression, a reduction was noted in 16.1% of the cases, and A2 was scored as undetectable in 39.4% of the cases. Gamido and coworkers (Gamido F, et al., Natural history of HLA expression during tumour development *Immunol Today* 14(10):491-99, 1993) emphasize that HLA changes appear to occur at a particular step in the progression from benign to most aggressive. Jiminez et al (Jiminez P, et al., Microsatellite instability analysis in tumors with different mechanisms for total loss of BMA expression. *Cancer Immunol* Immunother 48:684-90, 2000) have analyzed 118 different tumors (68 colorectal, 34 laryngeal and 16 melanomas). The frequencies reported for total loss of HLA expression were 11% for colon, 18% for melanoma and 13% for larynx. Thus, HLA class I expression is altered in a large fraction of the tumor types, possibly as a reflection of immune pressure, or simply a reflection of the accumulation of pathological changes and alterations in diseased cells.

A majority of tumors express HLA class I, with a general tendency for the more severe alterations to be found in later stage and less differentiated tumors. This pattern is encouraging in the context of immunotherapy, especially considering that: 1) the relatively low sensitivity of immunohistochemical techniques might underestimate HLA expression in tumors; 2) class I expression can be induced in tumor cells as a result of local inflammation and lymphokine release; and, 3) class I negative cells are sensitive to lysis by NK cells.

Currently there are a number of unmet needs in the area of cancer treatment. This is evidenced by the side effects associated with existing therapies employed for cancer treatment and the fact that less than 50% of patients are cured by current therapies. Therefore, an opportunity exists for a product with the ability to either increase response rates, duration of response, overall survival, disease free survival and/or quality of life.

SUMMARY OF THE INVENTION

In some embodiments, the invention is directed to an isolated peptide comprising or consisting of one or more HLA-A2 epitopes and/or HLA-A2 analogs. The peptide may comprise mutiple epitopes and/or analogs, and may comprise additional amino acid residues, including but not limited to, other CTL epitopes, universal HTL epitopes, HTL epitopes, linkers, spacers, carriers, etc.

In further embodiments, the invention is directed to polynucleotides encoding such peptides.

In further embodiments, the invention is directed to a composition comprising two, three, four, five, six, seven, eight, nine, ten, eleven or twelve peptide epitopes and/or analogs. One or more of the peptides and/or analogs in these embodiments may also further comprise additional amino acid residues including, but not limited to, other CTL epitopes, HTL epitopes, universal HTL epitopes, linkers, spacers, carriers, etc.

In further embodiments, the invention is directed to a composition comprising one or more of the above peptides and/or polynucleotides and one or more additional components. Additional components include diluents, excipients, CTL epitopes, HTL epitopes, carriers, liposomes, HLA heavy chains, β2-microglobulin, strepavidin, antigen-presenting cells, adjuvants, etc.

In further embodiments, the invention is directed to prophylactic, therapeutic, diagnostic, and prognostic methods using the peptides, polynucleotides, and compositions of the invention.

BRIEF DESCRIPTION OF THE DRAWINGS/FIGURES

FIG. 1 depicts that splenic DC from ProGP-treated mice induce CTL responses in vivo. In FIG. 1, Splenic DC from ProGP treated HLA-A2.1 transgenic mice (33 μg/mouse, QD, SC for 7 days) were pulsed in vitro with HBV Pol 455 peptide ($10^6$ cell per ml peptide at 10 μg/ml) in Opti-MEM I medium (Gibco Life Sciences) containing 3 μg/ml β2-microglobulin (Scripps Laboratories). After peptide pulsing for 3 hr at room temperature, DC were washed twice and $10^6$ cells were injected IV into groups of three transgenic mice. Epitope-pulsed GM-CSF/IL-4 expanded DC and "mock-pulsed" ProGP derived DC were also tested for comparison. Seven days after receiving the primary immunization with DC, animals were boosted with the same DC populations. At fourteen days after the primary immunization, spleen cells from immunized animals were restimulated twice in vitro in the presence of the Pol 455 peptide. CTL activity following restimulations was measured using a standard $^{51}$Cr release assay in which the lysis of $^{51}$Cr-labeled HLA-A2.1-transfected Jurkat target cells was measured in the presence (circle symbols) or absence of peptide (square symbols). The data points shown in Panels A-C represent a composite of lytic activity from a triplicate set of cultures. Panel A, splenic DC from ProGP (SD-9427) treated animals pulsed with the HBV Pol 455 peptide. Panel B, GM-CSF/IL-4 expanded DC pulsed with HBV Pol 455 peptide. Panel C, mock-pulsed DC from ProGP treated animals. Studies were performed at Epimmune Inc., San Diego, Calif.

Figure 2:
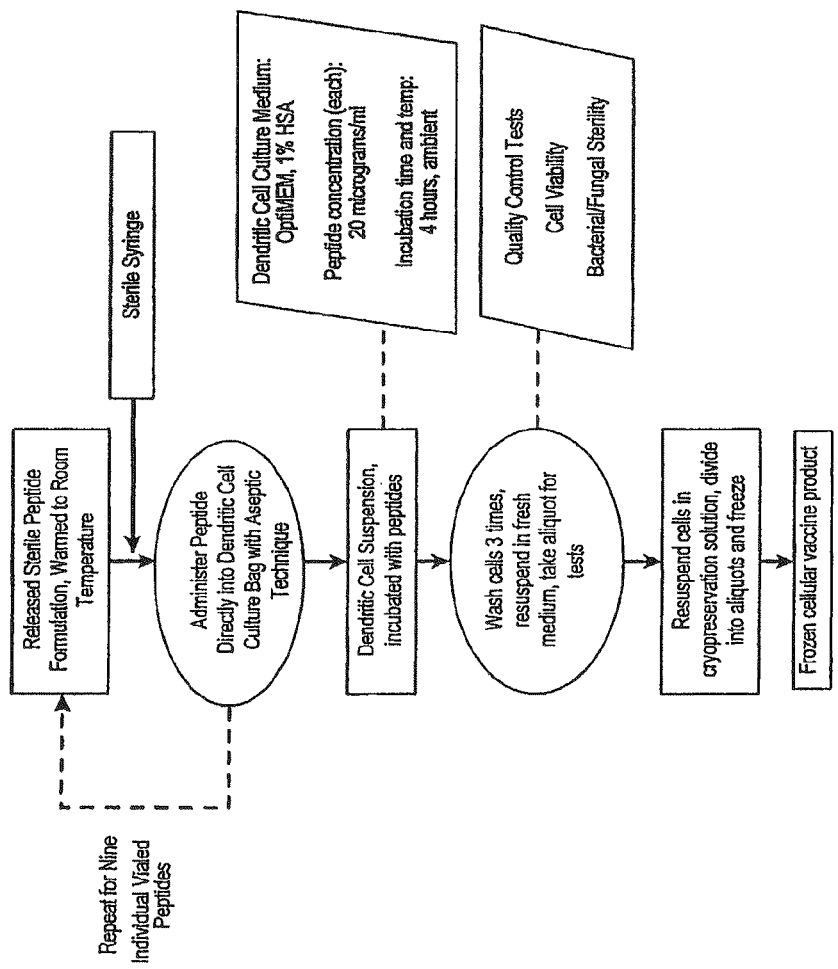

FIG. 2 presents a schematic of a dendritic cell pulsing and testing procedure.

Figure 3A:
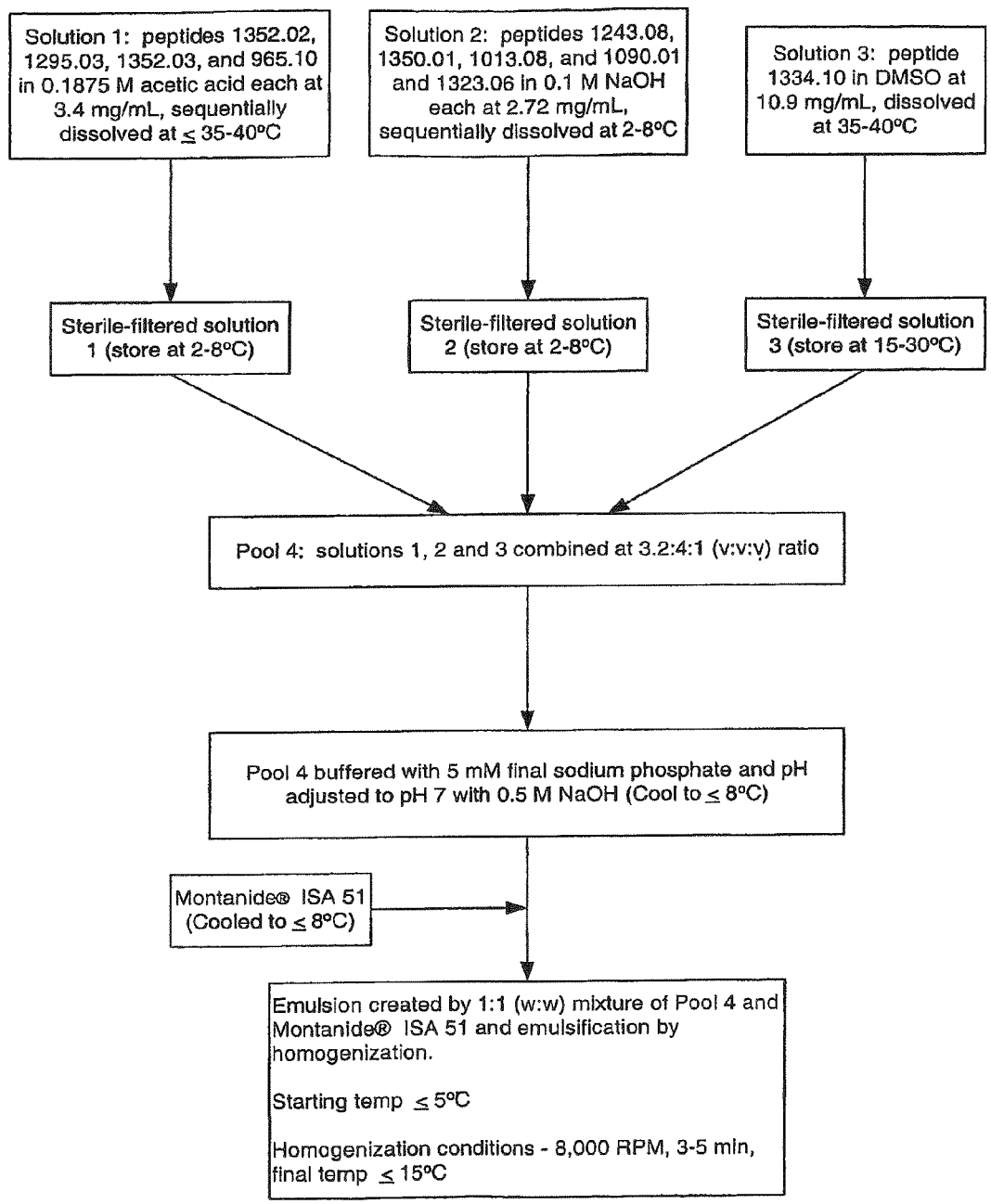

FIG. 3A shows a flow chart of the preparation of Drug Product.

Figure 3B:
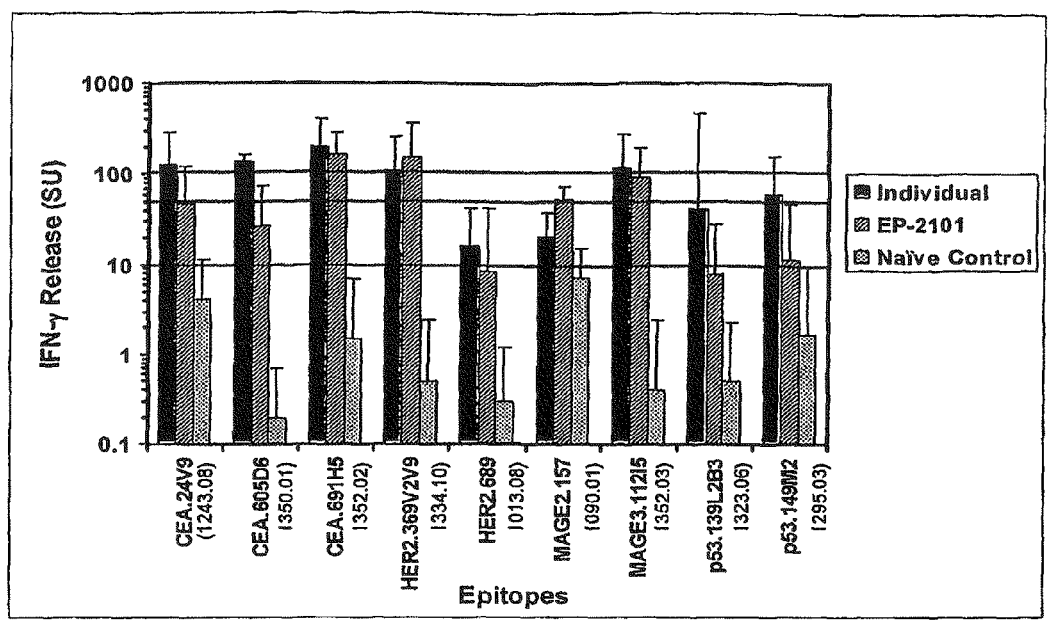

FIG. 3B shows multi-epitope CTL induction in HLA-A2.1/K$^b$ transgenic mice immunized with the EP-2101 vaccine. Mice were immunized with 50 µg of EP-2101 (10 mg/ml emulsion dose) or co-immunized with 50 µg of each CTL epitope individually with an equal dose of PADRE® epitope in Montanide® ISA 51 adjuvant (latter responses designated as "Individual"). Eleven to 14 days later, splenocytes from primed animals were stimulated with each CTL peptide in vitro and six days later CTL activity from triplicate cultures were measured with an in situ IFN-γ ELISA. As a control, splenocytes from naïve mice or mice injected with a Montanide® ISA 51 emulsion prepared without peptide were also stimulated with peptide in vitro and CTL activity was measured under identical conditions (responses designated as "Naïve control"). Data shown for each epitope is the geometric mean CTL response from 6-10 independent experiments. CTL responses are expressed in secretory units (SU) with 1 SU defined as the release of 100 pg/well of IFN-γ by 10$^6$ effector cells.

DETAILED DESCRIPTION OF THE INVENTION

This invention provides peptides that can be used to monitor an immune response to a tumor associated antigen or to create a cancer vaccine that stimulates the cellular arm of the immune system, especially when one or more peptides are combined. In particular embodiments, compositions mediate immune responses against tumors in individuals who bear at least one allele of HLA-A2 and/or HLA-A2 supertype. Such compositions will generally be referred to as A2 compositions (or combinations thereof).

An A2 composition may, for example, act as a vaccine to stimulate the immune system to recognize and kill tumor cells, leading to increased quality of life, and/or disease-free or overall survival rates for patients treated for cancer. In a preferred embodiment, a composition of the invention such as a vaccine will be administered to HLA-A2 or HLA-A2 supertype positive individuals who have a cancer that expresses at least one of the TAAs from which the epitopes or analogs were selected (e.g., CEA, p53, HER2/neu, MAGE2/3), examples of such cancers being breast, colon, lung, ovarian and gastric cancers and for MAGE 2/3, some melanomas. Thereby, an A2 composition, e.g., vaccine, improves the standard of care for patients being treated for breast, colon, lung, ovarian or gastric cancers, or melanoma.

A2 compositions, e.g., vaccines, of the invention comprise peptides bearing A2 motifs or A2 supermotifs (A2 epitopes and/or A2 analogs), as described herein, and/or nucleic acids encoding such peptides. Such compositions may also comprise a PADRE® epitope.

The peptides and corresponding nucleic acids and compositions of the present invention are useful for stimulating an immune response to TAAs by stimulating the production of CTL and optionally HTL responses, e.g. therapeutic prophylaxis, and are also useful for monitoring an immune response, e.g., diagnosis and prognosis. The peptides, which contain A2 epitopes derived directly or indirectly (i.e. by analoging) from native TAA protein amino acid sequences, are able to bind to HLA molecules and stimulate an immune response to TAAs. The complete sequence of the TAAs proteins analyzed described as SEQ ID NOs:11-15 herein can be obtained from GenBank. See Table 2.

The epitopes of the invention have been identified in a number of ways, as will be discussed below. Also discussed in greater detail is an embodiment of the invention in which analogs have been derived wherein the binding activity for HLA molecules or T cell receptor molecules was modulated by modifying specific amino acid residues to create analogs which exhibit altered (e.g., improved) immunogenicity.

DEFINITIONS

The invention can be better understood with reference to the following definitions:

Throughout this disclosure, "binding data" results are often expressed in terms of "$IC_{50}$'s." $IC_{50}$ is the concentration of peptide in a binding assay at which 50% inhibition of binding of a reference peptide is observed. Given the conditions in which the assays are run (i.e., limiting HLA proteins and labeled peptide concentrations), these values approximate $K_D$ values. Assays for determining binding are described in detail, e.g., in PCT publications WO 94/20127 and WO 94/03205, and other publications such Sidney et al., *Current Protocols in Immunology* 18.3.1 (1998); Sidney, et al., *J. Immunol.* 154:247 (1995); and Sette, et al., *Mol. Immunol.* 31:813 (1994). It should be noted that $IC_{50}$ values can change, often dramatically, if the assay conditions are varied, and depending on the particular reagents used (e.g., HLA preparation, etc.). For example, excessive concentrations of HLA molecules will increase the apparent measured $IC_{50}$ of a given ligand.

Alternatively, binding is expressed relative to a reference peptide. Although as a particular assay becomes more, or less, sensitive, the $IC_{50}$'s of the peptides tested may change somewhat, the binding relative to the reference peptide will not significantly change. For example, in an assay run under conditions such that the $IC_{50}$ of the reference peptide increases 10-fold, the $IC_{50}$ values of the test peptides will also shift approximately 10-fold. Therefore, to avoid ambiguities, the assessment of whether a peptide is a good (i.e. high), intermediate, weak, or negative binder is generally based on its $IC_{50}$, relative to the $IC_{50}$ of a standard peptide. The Tables included in this application present binding data in a preferred biologically relevant form of $IC_{50}$ nM.

Binding may also be determined using other assay systems including those using: live cells (e.g., Ceppellini et al., *Nature* 339:392 (1989); Christnick et al., *Nature* 352:67 (1991); Busch et al., *Int. Immunol* 2:443 (1990); Hill et al., *J. Immunol.* 147:189 (1991); del Guercio et al., *J. Immunol.* 154:685 (1995)), cell free systems using detergent lysates (e.g., Cerundolo et al., *J. Immunol.* 21:2069 (1991)), immobilized purified MHC (e.g., Hill et al., *J. Immunol.* 152, 2890 (1994); Marshall et al., *J. Immunol.* 152:4946 (1994)), ELISA systems (e.g., Reay et al., *EMBO J.* 11:2829 (1992)), surface plasmon resonance (e.g., Khilko et al., *J. Biol. Chem.* 268: 15425 (1993)); high flux soluble phase assays (Hammer et al., *J. Exp. Med.* 180:2353 (1994)), and measurement of class I MHC stabilization or assembly (e.g., Ljunggren et al., *Nature* 346:476 (1990); Schumacher; et al., *Cell* 62:563 (1990); Townsend et al., *Cell* 62:285 (1990); Parker et al., *J. Immunol.* 149:1896 (1992)).

As used herein, "high affinity" with respect to HLA class I molecules is defined as binding with an $IC_{50}$ or $K_D$ value, of 50 nM or less, "intermediate affinity" is binding with an $IC_{50}$ or $K_D$ value of between 50 and about 500 nM, "weak affinity" is binding with an $IC_{50}$ or $K_D$ value of between about 500 and about 5000 nM. "High affinity" with respect to binding to HLA class II molecules is defined as binding with an $IC_{50}$ or $K_D$ value of 100 nM or less; "intermediate affinity" is binding with an $IC_{so}$ or $K_D$ value of between about 100 and about 1000 nM.

A "computer" or "computer system" generally includes: a processor and related computer programs; at least one information storage/retrieval apparatus such as a hard drive, a disk drive or a tape drive; at least one input apparatus such as a keyboard, a mouse, a touch screen, or a microphone; and display structure, such as a screen or a printer. Additionally, the computer may include a communication channel in communication with a network. Such a computer may include more or less than what is listed above.

"Cross-reactive binding" indicates that a peptide is bound by more than one HLA molecule; a synonym is degenerate binding.

The term "derived" when used to discuss an epitope is a synonym for "prepared." A derived epitope can be isolated from a natural source, or it can be synthesized in accordance with standard protocols in the art. Synthetic epitopes can comprise artificial amino acid residues "amino acid mimetics," such as D isomers of natural occurring L amino acid residues or non-natural amino acid residues such as cyclohexylalanine. A derived or prepared epitope can be an analog of a native epitope.

A "diluent" includes sterile liquids, such as water and oils, including those of petroleum, animal, vegetable or synthetic origin, such as peanut oil, soybean oil, mineral oil, sesame oil and the like. Water is a preferred diluent for pharmaceutical compositions. Saline solutions and aqueous dextrose and glycerol solutions can also be employed as diluents, particularly for injectable solutions.

A "dominant epitope" is an epitope that induces an immune response upon immunization with a whole native antigen (see, e.g., Sercarz, et al., *Annu. Rev. Immunol.* 11:729-766, 1993). Such a response is cross-reactive in vitro with an isolated peptide epitope.

An "epitope" is the collective features of a molecule, such as primary, secondary and tertiary peptide structure, and charge, that together form a site recognized by an immunoglobulin, T cell receptor or HLA molecule. Alternatively, an epitope can be defined as a set of amino acid residues which is involved in recognition by a particular immunoglobulin, or in the context of T cells, those residues necessary for recognition by T cell receptor proteins and/or Major Histocompatibility Complex (MHC) receptors. Epitopes are present in nature, and can be isolated, purified or otherwise prepared or derived by humans. For example, epitopes can be prepared by isolation from a natural source, or they can be synthesized in accordance with standard protocols in the art. Synthetic epitopes can comprise artificial amino acid residues, "amino acid mimetics," such as D isomers of naturally-occurring L amino acid residues or non-naturally-occurring amino acid residues such as cyclohexylalanine. Throughout this disclosure, epitopes may be referred to in some cases as peptides or peptide epitopes. The epitopes and analogs of the invention are set forth in Table 3.

It is to be appreciated that proteins or peptides that comprise an epitope or an analog of the invention as well as additional amino acid(s) are still within the bounds of the invention. In certain embodiments, the peptide comprises a fragment of an antigen. A "fragment of an antigen" or "antigenic fragment" or simply "fragment" is a portion of an antigen which has 100% identity with a wild type antigen or naturally-occurring variant thereof. The fragment may or may not comprise an epitope of the invention. The fragment may be less than or equal to 600 amino acid residues, less than or equal to 500 amino acid residues, less than or equal to 400 amino acid residues, less than or equal to 250 amino acid residues, less than or equal to 100 amino acid residues, less than or equal to 85 amino acid residues, less than or equal to 75 amino acid residues, less than or equal to 65 amino acid residues, or less than or equal to 50 amino acid residues in length. In certain embodiments, a fragment is e.g., less than 101 or less than 51 amino acid residues in length, in any increment down to 5 amino acid residues in length. For example, the fragment may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues in length. In preferred embodiments, a peptide is 9, 10, or 11 amino acid residues in length.

In certain embodiments, there is a limitation on the length of a peptide of the invention. The embodiment that is length-limited occurs when the protein or peptide comprising an epitope of the invention comprises a region (i.e., a contiguous series of amino acid residues) having 100% identity with a native sequence. In order to avoid the definition of epitope from reading, e.g., on whole natural molecules, there is a limitation on the length of any region that has 100% identity with a native peptide sequence. Thus, for a peptide comprising an epitope of the invention and a region with 100% identity with a native peptide sequence, the region with 100% identity to a native sequence generally has a length of: less than or equal to 600 amino acid residues, often less than or equal to 500 amino acid residues, often less than or equal to 400 amino acid residues, often less than or equal to 250 amino acid residues, often less than or equal to 100 amino acid residues, often less than or equal to 85 amino acid residues, often less than or equal to 75 amino acid residues, often less than or equal to 65 amino acid residues, and often less than or equal to 50 amino acid residues. In certain embodiments, an "epitope" of the invention is comprised by a peptide having a region with less than 51 amino acid residues that has 100% identity to a native peptide sequence, in any increment down to 5 amino acid residues; for example 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 amino acid residues.

Accordingly, peptide or protein sequences longer than 600 amino acid residues are within the scope of the invention, provided that they do not comprise any contiguous sequence of more than 600 amino acid residues that have 100% identity with a native peptide sequence. For any peptide that has five contiguous residues or less that correspond to a native sequence, there is no limitation on the maximal length of that peptide in order to fall within the scope of the invention. It is presently preferred that a peptide of the invention (e.g., a peptide comprising an epitope of the invention) be less than 600 residues long in any increment down to eight amino acid residues. In a preferred embodiment, peptides of the invention are 9, 10 or 11 amino acid residues in length.

"Human Leukocyte Antigen" or "HLA" is a human class I or class II Major Histocompatibility Complex (MHC) protein (see, e.g., Stites, et al., IMMUNOLOGY, 8$^{TH}$ ED., Lange Publishing, Los Altos, Calif. (1994).

An "HLA supertype or HLA family", as used herein, describes sets of HLA molecules grouped on the basis of shared peptide-binding specificities. HLA class I molecules that share somewhat similar binding affinity for peptides bearing certain amino acid motifs are grouped into such HLA supertypes. The terms HLA superfamily, HLA supertype family, HLA family, and HLA xx-like molecules (where "xx" denotes a particular HLA type), are synonyms. See, e.g., the HLA-A2 motif and super motifs are detailed in Tables 4A, 4B, 4C, and 4D.

As used herein, "high affinity" with respect to HLA class I molecules is defined as binding with an $IC_{50}$, or $K_D$ value, of 50 nM or less; "intermediate affinity" is binding with an $IC_{50}$ or $K_D$ value of between about 50 and about 500 nM; "weak affinity" is binding with an $IC_{50}$ or $K_D$ value between about 500 and about 5000 nM. "High affinity" with respect to binding to HLA class II molecules is defined as binding with an $IC_{50}$ or $K_D$ value of 100 nM or less; "intermediate affinity" is binding with an $IC_{50}$ or $K_D$ value of between about 100 and about 1000 nM. See "binding data."

An "$IC_{50}$" is the concentration of peptide in a binding assay at which 50% inhibition of binding of a reference peptide is observed. Given the conditions in which the assays are run (i.e., limiting HLA proteins and labeled peptide concentrations), these values approximate $K_D$ values. See "binding data."

The terms "identical" or percent "identity," in, the context of two or more peptide sequences or antigen fragments, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

An "immunogenic" peptide or an "immunogenic" epitope or "peptide epitope" is a peptide that comprises an allele-specific motif or supermotif such that the peptide will bind an HLA molecule and induce a CTL and/or HTL response. Thus, immunogenic peptides of the invention are capable of binding to an appropriate HLA molecule and thereafter inducing a cytotoxic T lymphocyte (CTL) response, or a helper T lymphocyte (HTL) response, to the peptide.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. An "isolated" epitope refers to an epitope that does not include the whole sequence of the antigen from which the epitope was derived. Typically the "isolated" epitope does not have attached thereto additional amino acid residues that result in a sequence that has 100% identity over the entire length of a native sequence. The native sequence can be a sequence such as a tumor-associated antigen from which the epitope is derived. Thus, the term "isolated" means that the material is removed from its original environment (e.g., the natural environment if it is naturally occurring). For example, a naturally-occurring polynucleotide or peptide present in a living animal is not isolated, but the same polynucleotide or peptide, separated from some or all of the coexisting materials in the natural system, is isolated. Such a polynucleotide could be part of a vector, and/or such a polynucleotide or peptide could be part of a composition, and still be "isolated" in that such vector or composition is not part of its natural environment. Isolated RNA molecules include in vivo or in vitro RNA transcripts of the DNA molecules of the present invention, and further include such molecules produced synthetically.

"Major Histocompatibility Complex" or "MHC" is a cluster of genes that plays a role in control of the cellular interactions responsible for physiologic immune responses. In humans, the MHC complex is also known as the human leukocyte antigen (HLA) complex. For a detailed description of the MHC and HLA complexes, see, Paul, FUNDAMENTAL IMMUNOLOGY, 3' ED., Raven Press, New York (1993).

A "native" or a "wild type" sequence refers to a sequence found in nature. Such a sequence may comprise a longer sequence in nature.

A "negative binding residue" or "deleterious residue" is an amino acid residue which, if present at certain positions (typically not primary anchor positions) in a peptide epitope, results in decreased binding affinity of the peptide for its corresponding HLA molecule.

The terms "peptide" and "peptide epitope" are used interchangeably with "oligopeptide" in the present specification to designate a series of residues, typically L-amino acid residues, connected one to the other, typically by peptide bonds between the α-amino and carboxyl groups of adjacent amino acid residues.

"Synthetic peptide" refers to a peptide that is obtained from a non-natural source, e.g., is man-made. Such peptides may be produced using such methods as chemical synthesis or recombinant DNA technology. "Synthetic peptides" include "fusion proteins."

A "PanDR binding" peptide, a "PanDR binding epitope," or "PADRE®" peptide (Epimmune, San Diego, Calif.) is a member of a family of molecules that binds more than one HLA class II DR molecule. The pattern that defines the PADRE® family of molecules can be referred to as an HLA Class II supermotif. A PADRE® molecule binds to HLA-DR molecules and stimulates in vitro and in vivo human helper T lymphocyte (HTL) responses. For a further definition of the PADRE® family, see copending application U.S. Ser. No. 09/709,774, filed Nov. 11, 2000; and 09/707,738, filed Nov. 6, 2000; PCT publication Nos WO 95/07707, and WO 97/26784; U.S. Pat. Nos. 5,736,142 issued Apr. 7, 1998; 5,679,640, issued Oct. 21, 1997; and 6,413,935, issued Jul. 2, 2002.

"Pharmaceutically acceptable" refers to a generally non-toxic, inert, and/or physiologically compatible composition or component of a composition.

A "pharmaceutical excipient" or "excipient" comprises a material such as an adjuvant, a carrier, pH-adjusting and buffering agents, tonicity adjusting agents, wetting agents, preservatives, and the like. A "pharmaceutical excipient" is an excipient which is pharmaceutically acceptable.

The term "motif" refers to a pattern of residues in an amino acid sequence of defined length, preferably a peptide of less than about 15 ammo acid residues in length, or less than about 13 amino acid residues in length, usually from about 8 to about 13 amino acid residues (e.g., 8, 9, 10, 11, 12, or 13) for a class I HLA motif and from about 6 to about 25 amino acid residues (e.g., 6, 7, 8, 9, 10, 11, 12, 13, 14, 15, 16, 17, 18, 19, 20, 21, 22, 23, 24, or 25) for a class U HLA motif, which is recognized by a particular HLA molecule. Motifs are typically different for each HLA protein encoded by a given human HLA allele. These motifs often differ in their pattern of the primary and secondary anchor residues. In preferred embodiments, an MHC class I motif identifies a peptide of 9, 10, Or 11 amino acid residues in length.

A "supermotif" is a peptide binding specificity shared by HLA molecules encoded by two or more HLA alleles. Preferably, a supermotif-bearing peptide is recognized with high or intermediate affinity (as defined herein) by two or more HLA antigens.

A "primary anchor residue" is an amino acid at a specific position along a peptide sequence which is understood to provide a primary contact point between the immunogenic peptide and the HLA molecule. One, two or three, primary anchor residues within a peptide of defined length minimally defines a "motif" for an immunogenic peptide. These residues are understood to fit in close contact with peptide binding grooves of an HLA molecule, with their side chains buried in specific pockets of the binding grooves themselves. In one embodiment of an HLA class I motif, the primary anchor residues are located at position 2 (from the amino terminal position) and at the carboxyl terminal position of a peptide epitope in accordance with the invention. The primary anchor positions for the A2 motif and supermotif of HLA Class I are set forth in Tables 4A, 4B, 4C, and 4D. For example, analog peptides can be created by altering the presence or absence of particular residues in these anchor positions. Such analogs are used to modulate the binding affinity of an epitope comprising a particular motif or supermotif.

A "secondary anchor residue" is an amino acid at a position other than a primary anchor position in a peptide which may influence peptide binding. A secondary anchor residue occurs at a significantly higher frequency among HLA-bound peptides than would be expected by random distribution of amino acid residues at a given position. A secondary anchor residue can be identified as a residue which is present at a higher frequency among high or intermediate affinity binding peptides, or a residue otherwise associated with high or intermediate affinity binding. The secondary anchor residues are said to occur at "secondary anchor positions." For example, analog peptides can be created by altering the presence or absence of particular residues in these secondary anchor positions. Such analogs are used to finely modulate the binding affinity of an epitope comprising a particular motif or supermotif. The terminology "fixed peptide" is generally used to refer to an analog peptide that has changes in primary anchore position; not secondary. A "cryptic epitope" elicits a response by immunization with an isolated peptide, but the response is not cross-reactive in vitro when intact whole protein, which comprises the epitope, is used as an antigen.

"Promiscuous recognition" by a TCR is where a distinct peptide is recognized by various T cell clones in the context of various HLA molecules. Promiscuous binding by an HLA molecule is synonymous with cross-reactive binding.

A "protective immune response" or "therapeutic immune response" refers to a CTL and/or an HTL response to an antigen derived from an pathogenic antigen (e.g., an antigen from an infectious agent or a tumor antigen), which in some way prevents or at least partially arrests disease symptoms, side effects or progression. The immune response may also include an antibody response which has been facilitated by the stimulation of helper T cells.

The term "residue" refers to an amino acid residue or amino acid mimetic residue incorporated into a peptide or protein by an amide bond or amide bond mimetic.

A "subdominant epitope" is an epitope which evokes little or no response upon immunization with a whole antigen or a fragment of the whole antigen comprising a subdominant epitope and a dominant epitope, which comprise the epitope, but for which a response can be obtained by immunization with an isolated peptide, and this response (unlike the case of cryptic epitopes) is detected when whole antigen or a fragment of the whole antigen comprising a subdominant epitope and a dominant epitope is used to recall the response in vitro or in vivo.

As used herein, a "vaccine" is a composition used for vaccination, e.g., for prophylaxis or therapy, that comprises one or more peptides of the invention. There are numerous embodiments of vaccines in accordance with the invention, such as by a cocktail of one or more peptides; one or more peptides of the invention comprised by a polyepitopic peptide; or nucleic acids that encode such peptides or polypeptides, e.g., a minigene that encodes a polyepitopic peptide. The "one or more peptides" can include any whole unit integer from 1-150, e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I-binding peptides of the invention can be linked or to otherwise be combined with HLA class II-binding peptides, e.g., a PADRE® universal HTL-bindind peptide, to facilitate activation of both cytotoxic T lymphocytes and helper T lymphocytes. Vaccines can comprise peptide pulsed antigen presenting cells, e.g., dendritic cells.

The nomenclature used to describe peptides or proteins follows the conventional practice wherein the amino group is presented to the left (the amino- or N-terminus) and the carboxyl group to the right (the carboxy- or C-terminus) of each amino acid residue. When amino acid residue positions are referred to in a peptide epitope they are numbered in an amino to carboxyl direction with position one being the residue located at the amino terminal end of the epitope, or the peptide or protein of which it may be a part.

In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acid residues having D-forms is represented by a lower case single letter or a lower case three letter symbol. However, when three letter symbols or full names are used without capitals, they may refer to L amino acid residues. Glycine has no asymmetric carbon atom and is simply referred to as "Gly" or "G". The amino acid sequences, of peptides set forth herein are generally designated using the standard single letter symbol. (A, Alanine; C, Cysteine; D, Aspartic Acid; E, Glutamic Acid; F, Phenylalanine; G, Glycine; H, Histidine; I, Isoleucine; K, Lysine; L, Leucine; M, Methionine; N, Asparagine; P, Proline; Q, Glutamine; R, Arginine; S, Serine; T, Threonine; V, Valine; W, Tryptophan; and Y, Tyrosine.) In addition to these symbols, "B" in the single letter abbreviations used herein designates α-amino butyric acid. In some embodiments, α-amino butyric acid may be interchanged with cysteine.

Acronyms used herein are as follows:

| | |
|---|---|
| APC: | Antigen presenting cell |
| CD3: | Pan T cell marker |
| CD4: | Helper T lymphocyte marker |
| CD8: | Cytotoxic T lymphocyte marker |
| CEA: | Carcinoembryonic antigen (see, e.g., SEQ ID NO: 363) |
| CTL: | Cytotoxic T lymphocyte |
| DC: | Dendritic cells. DC function as potent antigen presenting cells by stimulating cytokine release from CTL lines that are specific for a model peptide derived from hepatitis B virus. In vivo experiments using DC pulsed ex vivo with an HBV peptide epitope have stimulated CTL immune responses in vivo following delivery to naïve mice. |
| DLT: | Dose-limiting toxicity, an adverse event related to therapy. |
| DMSO: | Dimethylsulfoxide |
| ELISA: | Enzyme-linked immunosorbant assay |
| E:T: | Effector:Target ratio |
| G-CSF: | Granulocyte colony-stimulating factor |
| GM-CSF: | Granulocyte-macrophage (monocyte)-colony stimulating factor |
| HBV: | Hepatitis B virus |
| HER2/neu: | A tumor associated antigen; c-erbB-2 is a synonym (see, e.g., SEQ ID NO: 364) |
| HLA: | Human leukocyte antigen |
| HLA-DR: | Human leukocyte antigen class II |
| HPLC: | High Performance Liquid Chromatography |
| HTC: | Helper T Cell |
| HTL: | Helper T Lymphocyte. A synonym for HTC. |
| ID: | Identity |
| IFNγ: | Interferon gamma |
| IL-4: | Interleukin-4 |
| IV: | Intravenous |
| $LU_{30\%}$: | Cytotoxic activity for $10^6$ effector cells required to achieve 30% lysis of a target cell population, at a 100:1 (E:T) ratio. |
| MAb: | Monoclonal antibody |
| MAGE: | Melanoma antigen (see, e.g., SEQ ID NO: 365 and 366 for MAGE2 and MAGE3, respectively) |
| MLR: | Mixed lymphocyte reaction |
| MNC: | Mononuclear cells |
| PB: | Peripheral blood |
| PBMC: | Peripheral blood mononuclear cell |
| ProGP ™: | Progenipoietin ™ product (Searle, St. Louis, MO), a chimeric flt3/G-CSF receptor agonist. |
| SC: | Subcutaneous |
| S.E.M.: | Standard error of the mean |
| QD: | Once a day dosing |
| TAA: | Tumor Associated Antigen |
| TNF: | Tumor necrosis factor |
| WBC: | White blood cells |

The following describes the peptides, corresponding nucleic acid molecules, compositions, and methods of the invention in more detail.

A2 Peptides and Polynucleotides of Tumor Associated Antigens

A2 Epitopes and Analogs. In some embodiments, the invention is directed to an isolated peptide comprising or consisting of an epitope and/or analog. In some embodiments, the invention is directed to an isolated polynucleotide encoding such a peptide.

The isolated epitopes and analogs of the invention are all class I binding peptides, i.e., CTL peptides. In particular, the epitopes and analogs of the invention comprise an A2 motif or supermotif. Epitopes and analogs of the invention are those set forth in Table 3 (SEQ ID NOs:1-10). A2 epitopes and analogs of the invention may be referred to herein as "epitopes" and "analogs" or referred to by Table or referred to by SEQ ID NO. Other epitopes and analogs are referred to herein as CTL epitopes or CTL peptides and HTL epitopes or HTL peptides.

Peptides and Polynucleotides. In some embodiments, the invention is directed to an isolated peptide comprising or consisting of an epitope and/or analog, wherein the epitope or analog consists of a sequence selected from those in Table 3 (SEQ ID NOs:1-10).

Preferably, the peptide comprises or consists of an epitope or analog consisting of a sequence in Table 3.

Peptides of the invention may be fusion proteins of epitope(s) and/or analog(s) to CTL epitope(s), and/or HTL epitope(s), and/or linker(s), and/or spacer(s), and/or carrier(s), and/or additional amino acid residue(s), and/or may comprise or consist of homopolymers of an epitope or analog or heteropolymers of epitopes and/or analogs, as is described in detail below.

Peptides which comprise an epitope and/or analog of the invention may comprise or consist of a fragment of an antigen ("fragment" or "antigenic fragment"), wherein the fragment comprises an epitope and/or analog. The fragment may be a portion of CEA, HER2/neu MAGE2, MAGE3, and/or p53 (SEQ ID Nos:11, 12, 13, 14, and 15, respectively). The epitope of the invention may be within the fragment or may be linked directly or indirectly, or otherwise connected to the fragment.

The fragment may comprise or consist of a region of a native antigen that contains a high concentration of class I and/or class II epitopes, preferably it contains the greatest number of epitopes per amino acid length. Such epitopes can be present in a frame-shifted manner, e.g., a 10 amino acid long peptide could contain two 9 amino acid residue long epitopes and one 10 amino acid residue long epitope.

The fragment may be less than or equal to 600 amino acid residues, less than or equal to 500 amino acid residues, less than or equal to 400 amino acid residues, less than or equal to 250 amino acid residues, less than or equal to 100 amino acid residues, less than or equal to 85 amino acid residues, less than or equal to 75 amino acid residues, less than or equal to 65 amino acid residues, or less than or equal to 50 amino acid residues in length. In certain embodiments, a fragment is less than 101 amino acid residues in length, in any increment down to 5 amino acid residues in length. For example, the fragment may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues in length. In preferred embodiments, fragments are 9, 10, or 11 amino acid residues in length.

Fragments of the full length CEA antigen may be fragments from about residue 1-20, 21-40, 41-60, 61-80, 81-100, 101-120, 121-140, 141-160, 161-180, 181-200, 201-220, 221-240, 241-260, 261-280, 281-300, 301-320, 321-340, 341-360, 361-380, 381-400, 401-420, 421-440, 441-460, 461-480, 481-500, 501-520, 521-540, 541-560, 561-580, 581-600, 601-620, 621-640, 641-660, 661-680 or 681 to the C-terminus of the antigen.

Fragments of the full length HER2/neu antigen may be fragments from about residue 1-20, 21-40, 41-60, 61-80, 81-100, 101-120, 121-140, 141-160, 161-180, 181-200, 201-220, 221-240, 241-260, 261-280, 281-300, 301-320, 321-340, 341-360, 361-380, 381-400, 401-420, 421-440, 441-460, 461-480, 481-500, 501-520, 521-540, 541-560, 561-580, 581-600, 601-620, 621-640, 641-660, 661-680, 681-700, 701-720, 721-740, 741-760, 761-780, 781-800, 801-820, 821-840, 841-860, 861-880, 881-900, 901-920, 921-940, 941-960, 961-980, 981-1000, 1001-1020, 1021-1040, 1041-1060, 1061-1080, 1081-1100, 1101-1120, 1121-1140, 1141-1160, 1161-1180, 1181-1200, 1201-1220, 1221-1240, or 1241 to the C-terminus of the antigen.

Fragments of the full length MAGE-2 antigen may be fragments from about residue 1-20, 21-40, 41-60, 61-80, 81-100, 101-120, 121-140, 141-160, 161-180, 181-200, 201-220, 221-240, 241-260, 261-280, 281-300 or 301 to the C-terminus of the antigen.

Fragments of the full length MAGE-3 antigen may be fragments from about residue 1-20, 21-40, 41-60, 61-80, 81-100, 101-120, 121-140, 141-160, 161-180, 181-200, 201-220, 221-240, 241-260, 261-280, 281-300 or 301 to the C-terminus of the antigen.

Fragments of the full length p53 antigen may be fragments from about residue 1-20, 21-40, 41-60, 61-80, 81-100, 101-120, 121-140, 141-160, 161-180, 181-200, 201-220, 221-240, 241-260, 261-280, 281-300, 301-320, 321-340, 341-360, 361-380 or 381 to the C-terminus of the antigen.

Peptides which comprise an epitope and/or analog of the invention may be a fusion protein comprising one or more amino acid residues in addition to the epitope, analog, or fragment. Fusion proteins include homopolymers and heteropolymers, as described below.

In some embodiments, the peptide comprises or consists of multiple epitopes and/or analogs, e.g., 2, 3, 4, 5, 6, 7, 8, 9 or 10 epitopes and/or analogs of the invention. In some embodiments, the peptide comprises at least 1, at least 2, at least 3, at least 4, at least 5, at least 6, at least 7, at least 8, at least 9 or at least 10 epitopes and/or analogs of the invention.

The peptide may also exclude any one or several epitopes and/or analogs selected from those in Table 3 (SEQ ID NOs: 1-10). Epitopes/analogs which may preferably be excluded from peptides of the invention are SEQ ID NOs:1-10.

The peptide may also be a homopolymer of one epitope or analog or the peptide may be a heteropolymer which contains at least two different epitopes and/or analogs. Polymers have the advantage of increased probability for immunological reaction and, where different epitopes/analogs are used to make up the polymer, the ability to induce antibodies and/or T cells that react with different antigenic determinants of the antigen(s) targeted for an immune response.

A homopolymer may comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, or 150 copies of the same epitope or analog.

A heteropolymer may comprise one or more copies of an individual epitope or analog and one or more copies of one or more different epitopes and/or analogs of the invention. The epitopes and/or analogs that form a heteropolymer may all be from the same antigen, e.g., may be from CEA, p53, MAGE2/3, HER2/neu or other antigens herein or known in the art, or may be from different antigens, preferably TAAs. Combinations of epitopes and/or analogs that may form a heteropolymer include those combinations described above. Heteropolymers may contain multiple copies of one or more epitopes and/or analogs.

Thus, peptides of the invention such as heteropolymers may comprise a first epitope and/or analog and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 other (different) epitopes and/or analogs.

Peptides of the invention may also comprise additional amino acid residues.

In some embodiments, the peptides may also comprise a number of CTL and/or HTL epitopes, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 CTL and/or HTL epitopes.

The CTL and/or HTL epitope and the epitope/analog of the invention may be from the same TAA or from different TAAs.

Thus, for example, if the epitope and/or analog is from CEA, the CTL peptide and/or HTL peptide may also be from CEA. Alternatively, the CTL peptide and/or HTL peptide may be from another antigen, preferably a TAA antigen such as p53, MAGE2/3 or HER2/neu. As another example, if the epitope and/or analog is from p53, the CTL peptide and/or HTL peptide may be from p53 or, alternatively, may be from MAGE2/3, HER2/neu, or CEA.

The CTL peptide and/or HTL peptide may be from tumor-associated antigens such as but not limited to, melanoma antigens MAGE-1, MAGE-2, MAGE-3, MAGE-11, MAGE-A10, as well as BAGE, GAGE, RAGE, MAGE-C1, LAGE-1, CAG-3, DAM, MUC1, MUC2, MUC18, NY-ESO-1, MUM-1, CDK4, BRCA2, NY-LU-1, NY-LU-7, NY-LU-12, CASP8, RAS, KTAA-2-5, SCCs, p53, p73, CEA, HER1/neu, Melan-A, gp100, tyrosinase, TRP2, gp75/TRP1, kallikrein, prostate-specific membrane antigen (PSM), prostatic acid phosphatase (PAP), prostate-specific antigen (PSA), PT1-1, β-catenin, PRAME, Telomerase, FAK, cyclin D1 protein, NOEY2, EGF-R, SART-1, CAPB, HPVE7, p15, Folate receptor CDC27, PAGE-1, and PAGE-4 (See, e.g., Table 16).

Non-limiting examples of CTL peptides and HTL peptides are disclosed in WO 01/42270, published 14 Jun. 2001; WO 01/41788, published 14 Jun. 2001; WO 01/42270, published 14 Jun. 2001; WO 01/45728, published 28 Jun. 2001; and WO 01/41787, published 14 Jun. 2001.

The HTL peptide may comprise a synthetic peptide such as a Pan-DR-binding epitope (e.g., a PADRE® peptide, Epimmune Inc., San Diego, Calif., described, for example, in U.S. Pat. No. 5,736,142), for example, having the formula aKX-VAAZTLKAAa, where "X" is either cyclohexylalanine, phenylalanine, or tyrosine; "Z" is either tryptophan, tyrosine, histidine or asparagine; and "a" is either D-alanine or L-alanine (SEQ ID NO: 746). Certain pan-DR binding epitopes comprise all "L" natural amino acid residues; these molecules can be provided as peptides or in the form of nucleic acids that encode the peptide. See also, U.S. Pat. Nos. 5,679,640 and 6,413,935.

The peptide may comprise additional amino acid residues. Such additional amino acid residues may be Ala, Arg, Asn, Asp, Cys, Gln, Gly, Glu, H is, Ile, Leu, Lys, Met, Phe, Pro, Ser, Thr, Tyr, Trp, Val, amino acid mimetics, and other unnatural amino acid residues such as those described below. Additional amino acid residues may provide for ease of linking peptides one to another, for linking epitopes and/or analogs to one another, for linking epitopes and/or analogs to CTL and/or HTL epitopes, for coupling to a carrier support or larger peptide, for modifying the physical or chemical properties of the peptide, or oligopeptide, or the like. Amino acid residues such as Ala, Arg, Asn, Asp, Cys, Gln, Gly, Glu, H is, Ile, Leu, Lys, Met, Phe, Pro, Ser, Thr, Tyr, Trp, or Val, or the like, can be introduced at the C- and/or N-terminus of the peptide and/or can be introduced internally.

The peptide may comprise an amino acid spacer, which may be joined to the epitopes, analogs, CTL epitopes, HTL epitopes, carriers, etc. within a peptide or may be joined to the peptide at the N- and/or C-terminus. Thus, spacers may be at the N-terminus or C-terminus of peptide, or may be internal such that they link or join epitopes, analogs, CTL epitopes, HTL epitopes, carriers, additional amino acid residues, and/or antigenic fragments one to the other.

The spacer is typically comprised of one or more relatively small, neutral molecules, such as amino acid residues or amino acid mimetics, which are substantially uncharged under physiological conditions. The spacers are typically selected from, e.g., Ala, Gly, or other neutral spacers of non-polar amino acid residues or neutral polar amino acid residues. It will be understood that the optionally present spacer may be composed of the same residues or may be composed of one or more different residues and thus may be a homo- or hetero-oligomer of spacer residues. Thus, the spacer may contain more than one Ala residue (poly-alanine) or more than one Gly residue (poly-glycine), or may contain both Ala and Gly residues, e.g., Gly, Gly-Gly-, Ser,Ser-Ser-, Gly-Ser-, Ser-Gly-, etc. When present, the spacer will usually be at least one or two residues, more usually three to six residues and sometimes 10 or more residues, e.g., 3, 4, 5, 6, 7, 8, 9, or 10, or even more residues. (Livingston, B. D. et al. *Vaccine* 19:46524660 (2000)).

Peptides may comprise carriers such as those well known in the art, e.g., thyroglobulin, albumins such as human serum albumin, tetanus toxoid, polyamino acid residues such as poly L-lysine, poly L-glutamic acid, influenza virus proteins, hepatitis B virus core protein, and the like.

In addition, the peptide may be modified by terminal-$NH_2$ acylation, e.g., by alkanoyl ($C_1$-$C_{20}$) or thioglycolyl acetylation, terminal-carboxyl amidation, e.g., ammonia, methylamine, etc. In some instances these modifications may provide sites for linking to a support or other molecule.

The peptides in accordance with the invention can contain modifications such as but not limited to glycosylation, side chain oxidation, biotinylation, phosphorylation, addition of a surface active material, e.g. a lipid, or can be chemically modified, e.g., acetylation, etc. Moreover, bonds in the peptide can be other than peptide bonds, e.g., covalent bonds, ester or ether bonds, disulfide bonds, hydrogen bonds, ionic bonds, etc.

Peptides of the present invention may contain substitutions to modify a physical property (e.g., stability or solubility) of the resulting peptide. For example, peptides may be modified by the substitution of a cysteine (C) with α-amino butyric acid ("B"). Due to its chemical nature, cysteine has the propensity to form disulfide bridges and sufficiently alter the peptide structurally so as to reduce binding capacity. Substituting α-amino butyric acid for C not only alleviates this problem, but actually improves binding and crossbinding capability in certain instances. Substitution of cysteine with α-amino butyric acid may occur at any residue of a peptide, e.g., at either anchor or non-anchor positions of an epitope or analog within a peptide, or at other positions of a peptide.

The peptides can comprise amino acid mimetics or unnatural, amino acid residues, e.g. D- or L-naphylalanine; D- or L-phenylglycine; D- or L-2-thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoro-methyl)-phenylalanine; D-ρ-fluorophenylalanine; D- or L-ρ-biphenyl-phenylalanine; D- or L-ρ-methoxybiphenylphenylalanine; D- or L-2-indole(alkyl)alanines; and, D- or L-alkylalanines, where the alkyl group can be a substituted or unsubstituted methyl, ethyl, propyl, hexyl, butyl, pentyl, iso-propyl, iso-butyl, sec-isotyl, iso-pentyl, or a non-acidic amino acid residues. Aromatic rings of a non-natural amino acid include, e.g., thiazolyl, thiophenyl, pyrazolyl, benzimidazolyl, naphthyl, furanyl, pyrrolyl, and pyridyl aromatic rings. Modified peptides that have various amino acid mimetics or unnatural amino acid residues are particularly useful, as they tend to manifest increased stability in vivo. Such peptides may also possess improved shelf-life or manufacturing properties.

Peptide stability can be assayed in a number of ways. For instance, peptidases and various biological media, such as human plasma and serum, have been used to test stability. See, e.g., Verhoef, et al., *Eur. J. Drug Metab. Pharmacokinetics* 11:291 (1986). Half-life of the peptides of the present invention is conveniently determined using a 25% human serum (v/v) assay. The protocol is generally as follows: Pooled human serum (Type AB, non-heat inactivated) is delipidated by centrifugation before use. The serum is then diluted to 25% with RPMI-1640 or another suitable tissue culture medium. At predetermined time intervals, a small amount of reaction solution is removed and added to either 6% aqueous trichloroacetic acid (TCA) or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

The peptides in accordance with the invention can be a variety of lengths, and either in their neutral (uncharged) forms or in forms which are salts. The peptides in accordance with the invention can contain modifications such as glycosylation, side chain oxidation, or phosphorylation, generally subject to the condition that modifications do not destroy the biological activity of the peptides.

The peptides of the invention may be lyophylized, or may be in crystal form.

It is generally preferable that the epitope be as small as possible while still maintaining substantially all of the immunologic activity of the native protein. When possible, it may be desirable to optimize HLA class I binding epitopes of the invention to a length of about 8 to about 13 amino acid residues, for example, 8, 9, 10, 11, 12 or 13, preferably 9 or 10. It is to be appreciated that one or more epitopes in this size range can be comprised by a longer peptide (see the Definition Section for the term "epitope" for further discussion of peptide length). HLA class II binding epitopes are preferably optimized to a length of about 6 to about 30 amino acid residues in length, e.g., 6, 7, 8, 9, 10, 11, 12, 13, 14, 15, 16, 17, 18, 19, 20, 21, 22, 23, 24, 25, 26, 27, 28, 29 or 30, preferably to between about 13 and about 20 residues, e.g., 13, 14, 15, 16, 17, 18, 19 or 20. Preferably, the epitopes are commensurate in size with endogenously processed pathogen-derived peptides or tumor cell peptides that are bound to the relevant HLA molecules. The identification and preparation of peptides of various lengths can be carried out using the techniques described herein.

Peptides in accordance with the invention can be prepared synthetically, by recombinant DNA technology or chemical synthesis, or can be isolated from natural sources such as native tumors or pathogenic organisms. Epitopes may be synthesized individually or joined directly or indirectly in a peptide. Although the peptide will preferably be substantially free of other naturally occurring host cell proteins and fragments thereof, in some embodiments the peptides may be synthetically conjugated to be joined to native fragments or particles.

The peptides of the invention can be prepared in a wide variety of ways. For relatively short sizes, the peptides can be synthesized in solution or on a solid support in accordance with conventional techniques. Various automatic synthesizers are commercially available and can be used in accordance with known protocols. (See, for example, Stewart & Young, SOLID PHASE PEPTIDE SYNTHESIS, 2D. ED., Pierce Chemical Co., 1984). Further, individual peptides can be joined using chemical ligation to produce larger peptides that are still within the bounds of the invention.

Alternatively, recombinant DNA technology can be employed wherein a nucleotide sequence which encodes a peptide inserted into an expression vector, transformed or transfected into an appropriate host cell and cultivated under conditions suitable for expression. These procedures are generally known in the art, as described generally in Sambrook et al., MOLECULAR CLONING, A LABORATORY MANUAL, Cold Spring Harbor Press, Cold Spring Harbor, N.Y. (1989). Thus, recombinant peptides, which comprise or consist of one or more epitopes of the invention, can be used to present the appropriate T cell epitope.

Polynucleotides encoding each of the peptides above are also part of the invention. As appreciated by one of ordinary skill in the art, various nucleic acids will encode the same peptide due to the redundancy of the genetic code. Each of these nucleic acids falls within the scope of the present invention. This embodiment of the invention comprises DNA and RNA, and in certain embodiments a combination of DNA and RNA. It is to be appreciated that any polynucleotide that encodes a peptide in accordance with the invention falls within the scope of this invention.

The polynucleotides encoding peptides contemplated herein can be synthesized by chemical techniques, for example, the phosphotriester method of Matteucci, et al., *J. Am. Chem. Soc.* 103:3185 (1981). Polynucleotides encoding peptides comprising or consisting of an analog can be made simply by substituting the appropriate and desired nucleic acid base(s) for those that encode the native epitope.

The polynucleotide, e.g. minigene (see below), may be produced by assembling oligonucleotides that encode the plus and minus strands of the polynucleotide, e.g. minigene. Overlapping oligonucleotides (15-100 bases long) may be synthesized, phosphorylated, purified and annealed under appropriate conditions using well known techniques. The ends of the oligonucleotides can be joined, for example, using T4 DNA ligase. A polynucleotide, e.g. minigene, encoding the peptide of the invention, can be cloned into a desired vector such as an expression vector. The coding sequence can then be provided with appropriate linkers and ligated into expression vectors commonly available in the art, and the vectors used to transform suitable hosts to produce the desired peptide such as a fusion protein.

A large number of such vectors and suitable host systems are known to those of skill in the art, and are commercially available. The following vectors are provided by way of example. Bacterial: pQE70, pQE60, pQE-9 (Qiagen), pBS, pD10, phagescript, psiX174, pBluescript SK, pbsks, pNH$_8$A, pNH16a, pNH18A, pNH46A (Stratagene); ptrc99a, pKK223-3, pKK233-3, pDR540, pRIT5 (Pharmacia); pCR (Invitrogen). Eukaryotic: pWLNEO, pSV2CAT, pOG44, pXT1, pSG (Stratagene) pSVK3, pBPV, pMSG, pSVL (Pharmacia); p75.6 (Valentis); pCEP (Invitrogen); pCEI (Epimmune). However, any other plasmid or vector can be used as long as it is replicable and viable in the host.

As representative examples of appropriate hosts, there can be mentioned: bacterial cells, such as *E. coli, Bacillus subtilis, Salmonella typhimurium* and various species within the genera *Pseudomonas, Streptomyces*, and *Staphylococcus*; fungal cells, such as yeast; insect cells such as *Drosophila* and Sf9; animal cells such as COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines or Bowes melanoma; plant cells, etc. The selection of an appropriate host is deemed to be within the scope of those skilled in the art from the teachings herein.

Thus, the present invention is also directed to vectors, preferably expression vectors useful for the production of the peptides of the present invention, and to host cells comprising such vectors.

Host cells are genetically engineered (transduced or transformed or transfected) with the vectors of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the polynucleotides. The culture conditions, such as temperature, pH and the like, are those previously used with the host cell selected for expression, and will be apparent to the ordinarily skilled artisan.

For expression of the peptides, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), ∀-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Yeast, insect or mammalian cell hosts may also be used, employing suitable vectors and control sequences. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5" flanking nontranscribed sequences. Such promoters may also be derived from viral sources, such as, e.g., human cytomegalovirus (CMV-IE promoter) or herpes simplex virus type-1 (HSV TK promoter). Nucleic acid sequences derived from the SV40 splice, and polyadenylation sites can be used to provide the required nontranscribed genetic elements.

Polynucleotides encoding peptides of the invention may also comprise a ubiquitination signal sequence, and/or a targeting sequence such as an endoplasmic reticulum (ER) signal sequence to facilitate movement of the resulting peptide into the endoplasmic reticulum.

Polynucleotides of the invention, e.g., minigenes, may be expressed in human cells. A human codon usage table can be used to guide the codon choice for each amino acid. Such polynucleotides preferably comprise spacer amino acid residues between epitopes and/or analogs, such as those described above, or may comprise naturally-occurring flanking sequences adjacent to the epitopes and/or analogs (and/or CTL and HTL epitopes).

The peptides of the invention can also be expressed by viral or bacterial vectors. Examples of expression vectors include attenuated viral hosts, such as vaccinia or fowlpox. As an example of this approach, vaccinia virus is used as a vector to express nucleotide sequences that encode the peptides of the invention. Vaccinia vectors and methods useful in immunization protocols are described in, e.g., U.S. Pat. No. 4,722,848. Another vector is BCG (Bacille Calmette Guerin). BCG vectors are described by Stover et al., *Nature* 351:456-460 (1991). A wide variety of other vectors useful for therapeutic administration or immunization of the polypeptides of the invention, e.g. adeno and adeno-associated virus vectors, retroviral vectors, *Salmonella typhi* vectors, detoxified anthrax toxin vectors, and the like, will be apparent to those skilled in the art from the description herein. A preferred vector is Modified Vaccinia Ankara (MVA) (e.g., Bavarian Noridic (MVA-BN)).

Standard regulatory sequences well known to those of skill in the art are preferably included in the vector to ensure expression in the human target cells. Several vector elements are desirable: a promoter with a downstream cloning site for polynucleotide, e.g., minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences. A preferred promoter is the CMV-IE promoter.

Polynucleotides, e.g. minigenes, may comprise one or more synthetic or naturally-occurring introns in the transcribed region. The inclusion of mRNA stabilization sequences and sequences for replication in mammalian cells may also be considered for increasing polynucleotide, e.g. minigene, expression.

In addition, the polynucleotide, e.g. minigene, may comprise immunostimulatory sequences (ISSs or CpGs). These sequences may be included in the vector, outside the polynucleotide (e.g. minigene) coding sequence to enhance immunogenicity.

In some embodiments, a bi-cistronic expression vector which allows production of both the polynucleotide (e.g. minigene) encoded peptides of the invention and a second protein (e.g., one that modulates immunogenicity) can be used. Examples of proteins or polypeptides that, if co-expressed with peptides of the invention, can enhance an immune response include cytokines (e.g., IL-2, IL-12, GM-CSF), cytokine-inducing molecules (e.g., Lea), costimulatory molecules, or pan-DR binding proteins (PADRE® molecules, Epimmune, San Diego, Calif.). Helper T cell (HTL) epitopes such as PADRE® molecules can be joined to intracellular targeting signals and expressed separately from expressed peptides of the invention. Specifically decreasing the immune response by co-expression of immunosuppressive molecules (e.g. TGF-β) may be beneficial in certain diseases.

Once an expression vector is selected, the polynucleotide, e.g. minigene, is cloned into the polylinker region downstream of the promoter. This plasmid is transformed into an appropriate bacterial strain, and DNA is prepared using standard techniques. The orientation and DNA sequence of the polynucleotide, e.g. minigene, as well as all other elements included in the vector, are confirmed using restriction mapping, DNA sequence analysis, and/or PCR analysis. Bacterial cells harboring the correct plasmid can be stored as cell banks.

Therapeutic/prophylactic quantities of DNA can be produced for example, by fermentation in *E. coli*, followed by purification. Aliquots from the working cell bank are used to inoculate growth medium, and are grown to saturation in shaker flasks or a bioreactor according to well known techniques. Plasmid DNA is purified using standard bioseparation technologies such as solid phase anion-exchange resins available, e.g., from QIAGEN, Inc. (Valencia, Calif.). If required, supercoiled DNA can be isolated from the open circular and linear forms using gel electrophoresis or other methods.

Purified polynucleotides, e.g. minigenes, can be prepared for injection using a variety of formulations. The simplest of these is reconstitution of lyophilized polynucleotide, e.g. DNA, in sterile phosphate-buffer saline (PBS). This approach, known as "naked DNA," is currently being used by others for intramuscular (IM) administration in clinical trials. To maximize the immunotherapeutic effects of polynucleotide vaccines, alternative methods of formulating purified plasmid DNA may be used. A variety of such methods have been described, and new techniques may become available. Cationic lipids, glycolipids, and fusogenic liposomes can also be used in the formulation (see, e.g., WO 93/24640; Mannino & Gould-Fogerite, *BioTechniques* 6(7): 682 (1988); U.S. Pat. No. 5,279,833; WO 91/06309; and Feigner, et al., *Proc. Nat'l Acad. Sci. USA* 84:7413 (1987). In addition, peptides and compounds referred to collectively as protective, interactive, non-condensing compounds (PINC) can also be complexed to purified plasmid DNA to influence variables such as stability, intramuscular dispersion, or trafficking to specific organs or cell types.

Known methods in the art can be used to enhance delivery and uptake of a polynucleotide in vivo. For example, the polynucleotide can be complexed to polyvinylpyrrolidone (PVP), to prolong the localized bioavailability of the polynucleotide, thereby enhancing uptake of the polynucleotide by the organisum (see e.g., U.S. Pat. No. 6,040,295; EP 0 465 529; WO 98/17814). This approache is thought to be more effective than inoculation with merely "naked" DNA. PVP is a polyamide that is known to form complexes with a wide variety of substances, and is chemically and physiologically inert.

Target cell sensitization can be used as a functional assay of the expression and HLA class I presentation of polynucleotide- (e.g. minigene-) encoded peptides. For example, the polynucleotide, e.g. plasmid DNA, is introduced into a mammalian cell line that is a suitable target for standard CTL chromium release assays. The transfection method used will be dependent on the final formulation. For example, electroporation can be used for "naked" DNA, whereas cationic lipids or PVP-formulated DNA allow direct in vitro transfection. A plasmid expressing green fluorescent protein (GFP) can be co-transfected to allow enrichment of transfected cells using fluorescence activated cell sorting (FACS). The transfected cells are then chromium-51 ($^{51}Cr$) labeled and used as targets for epitope-specific CTLs. Cytolysis of the target cells, detected by $^{51}Cr$ release, indicates both production and HLA presentation of, polynucleotide-, e.g. minigene-, encoded epitopes and/or analogs of the invention, or peptides comprising them. Expression of HTL epitopes may be evaluated in an analogous manner using assays to assess HTL activity.

In vivo immunogenicity is a second approach for functional testing of polynucleotides, e.g. minigenes. Transgenic mice expressing appropriate human HLA proteins are immunized with the polynucleotide, e.g. DNA, product. The dose and route of administration are formulation dependent (e.g., IM for polynucleotide (e.g., naked DNA or PVP-formulated DNA) in PBS, intraperitoneal (IP) for lipid-complexed polynucleotide (e.g., DNA)). Eleven to twenty-one days after immunization, splenocytes are harvested and restimulated for one week in the presence of polynucleotides encoding each peptide being tested. Thereafter, for peptides comprising or consisting of epitopes and/or analogs, standard assays are conducted to determine if there is cytolysis of peptide-loaded, $^{51}$Cr-labeled target cells. Once again, lysis of target cells that were exposed to epitopes and/or analogs corresponding to those encoded by the polynucleotide, e.g. minigene, demonstrates polynucleotide, e.g., DNA, vaccine function and induction of CTLs. Immunogenicity of HTL epitopes is evaluated in transgenic mice in an analogous manner.

Alternatively, the nucleic acids can be administered using ballistic delivery as described, for instance, in U.S. Pat. No. 5,204,253. Using this technique, particles comprised solely of a polynucleotide such as DNA are administered. In a further alternative embodiment for ballistic delivery, polynucleotides such as DNA can be adhered to particles, such as gold particles.

The use of polynucleotides such as multi-epitope minigenes is described herein and in, e.g. co-pending application U.S. Ser. No. 09/311,784; Ishioka et al., *J. Immunol.* 162: 3915-3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a polynucleotide such as a multi-epitope DNA plasmid can be engineered which encodes an epitope derived from multiple regions of a TAA (e.g., p53, HER2/neu, MAGE-2/3, or CEA), a pan-DR binding peptide such as the PADRE® universal helper T cell epitope, and an endoplasmic reticulum-translocating signal sequence. As described in the sections above, a peptide/polynucleotide may also comprise/encode epitopes that are derived from other TAAs.

Thus, the invention includes peptides as described herein, polynucleotides encoding each of said peptides, as well as compositions comprising the peptides and polynucleotides, and includes methods for producing and methods of using the peptides, polynucleotides, and compositions, as further described below.

Compositions. In other embodiments, the invention is directed to a composition comprising one or more peptides and/or a polynucleotide of the invention and optionally another component(s).

In some embodiments, the composition comprises or consists of multiple peptides, e.g., 2, 3, 4, 5, 6, 7, 8, 9 or 10 peptides of the invention. In some embodiments, the composition comprises at least 2, at least 3, at least 4, at least 5, at least 6, at least 7, at least 8, at least 9 or at least 10 peptides of the invention.

Compositions of the invention may comprise polynucleotides encoding the above peptides and/or combinations of peptides.

The composition can comprise at least 2, at least 3, at least 4, at least 5, at least 6, at least 7, at least 8, at least 9 or at least 10 peptides and/or polynucleotides selected from those described above or below. At least one of the one or more peptides can be a heteropolymer or a homopolymer. Additionally, the composition can comprise a CTL and/or HTL epitope, which can be derived from a tumor-associated antigen. The additional epitope can also be a PanDR binding molecule, (e.g., a PADRE® universal helper T cell epitope).

Optional components include excipients, diluents, proteins such as peptides comprising a CTL epitope, and/or an HTL epitope such as a pan-DR binding peptide (e.g., a PADRE® universal helper T cell epitope), and/or a carrier, polynucleotides encoding such proteins, lipids, or liposomes, as well as other components described herein. There are numerous embodiments of compositions in accordance with the invention, such as a cocktail of one or more peptides and/or polynucleotides; one or more peptides and/or analogs and one or more CTL and/or HTL epitopes; and/or nucleic acids that encode such peptides, e.g., minigenes.

Compositions may comprise one or more peptides (and/or polynucleotides such as minigenes) of the invention, along with one or more other components as described above and herein. "One or more" refers to any whole unit integer from 1-150, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, or 150 peptides, polynucleotides, or other components.

Compositions of the invention may be, for example, polynucleotides or, polypeptides of the invention combined with or completed to cationic lipid formulations; lipopeptides (e.g., Vitiello, A. et al., *J. Clin. Invest.* 95:341, 1995), encapsulated e.g., in poly(DL-lactide-co-glycolide) ("PLG") microspheres (see, e.g., Eldridge, et al., *Molec. Immunol.* 28:287-294, 1991: Alonso et al., *Vaccine* 12:299-306, 1994; Jones et al., *Vaccine* 13:675-681, 1995); peptide compositions contained in immune stimulating complexes (ISCOMS) (see, e.g., Takahashi et al., *Nature* 344:873-875, 1990; Hu et al., *Clin Exp Immunol.* 113:235-243, 1998); multiple antigen peptide systems (MAPS) (see e.g., Tam, J. P., *Proc. Natl. Acad. Sci. U.S.A.* 85:5409-5413, 1988; Tam, J. P., *J. Immunol. Methods* 196:17-32, 1996); viral, bacterial, or, fungal delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990); particles of viral or synthetic origin (e.g., Kofler, N. et al., *J. Immunol. Methods.* 192:25, 1996; Eldridge, J. H. et al., *Sem. Hematol.* 30:16, 1993; Falo, L. D., Jr. et al., *Nature Med.* 7:649, 1995); adjuvants (e.g., incomplete Freund's adjuvant) (Warren, H. S., Vogel, F. R., and Chedid, L. A. *Annu. Rev. Immunol.* 4:369, 1986; Gupta, R. K. et al., *Vaccine* 11:293, 1993); liposomes (Reddy, R. et al., *J. Immunol.* 148:1585, 1992; Rock, K. L., *Immunol. Today* 17:131, 1996); or, particle-absorbed cDNA or other polynucleotides of the invention (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993), etc. Toxin-targeted delivery technologies, also known as receptor mediated targeting, such as those of Avant Immunotherapeutics, Inc. (Needham, Mass.) or attached to a stress protein, e.g., HSP 96 (Stressgen Biotechnologies Corp., Victoria, BC, Canada) can also be used.

Compositions of the invention comprise polynucleotide-mediated modalities. DNA or RNA encoding one or more of the peptides of the invention can be administered to a patient. This approach is described, for instance, in Wolff et. al., *Science* 247:1465 (1990) as well as U.S. Pat. Nos. 5,580,859; 5,589,466; 5,804,566; 5,739,118; 5,736,524; 5,679,647; and, WO 98/04720. Examples of DNA-based delivery technologies include "naked DNA" (see, e.g., U.S. Pat. No. 5,693, 622), facilitated DNA ((i.e., non-"naked DNA") facilitated e.g., by combination with bupivicaine, polymers (e.g., PVP, PINC, etc.), peptide-mediated) delivery, cationic lipid complexes, and particle-mediated ("gene gun") or pressure-mediated delivery (see, e.g., U.S. Pat. No. 5,922,687). Accordingly, peptides of the invention can be expressed by viral or bacterial vectors. Examples of expression vectors include attenuated viral hosts, such as Modified Vaccinia Ankara (MVA) (e.g., Bavarian Noridic), vaccinia or fowlpox. For example, vaccinia virus is used as a vector to express nucleotide sequences that encode the peptides of the invention. Upon introduction into an acutely or chronically infected host or into a non-infected host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 351:456-460 (1991). A wide variety of other vectors useful for therapeutic administration or immunization of the peptides of the invention, e.g. adeno and adeno-associated virus vectors, alpha virus vectors, retroviral vectors, Salmonella typhi vectors, detoxified anthrax toxin vectors, and the like, are apparent to those skilled in the art from the description herein.

In certain embodiments, components that induce T cell responses are combined with components that induce antibody responses to the target antigen of interest. A preferred embodiment of such a composition comprises class I and class II epitopes in accordance with the invention. Alternatively, a composition comprises a class I and/or class II epitope in accordance with the invention, along with a PADRE® molecule (Epimmune, San Diego, Calif.).

Compositions of the invention can comprise antigen presenting cells, such as dendritic cells. Antigen presenting cells, e.g., dendritic cells, may be transfected, e.g., with a polynucleotide such as a minigene construct in accordance with the invention, in order to elicit immune responses. The peptide can be bound to an HLA molecule on the antigen-resenting cell, whereby when an HLA-restricted cytotoxic T lymphocyte (CTL) is present, a receptor of the CTL binds to a complex of the HLA molecule and the peptide.

The compositions of the invention may also comprise antiviral drugs such as interferon-α, or immune adjuvants such as IL-12, GM-CSF, etc.

Compositions may comprise an HLA heavy chain, $\beta_2$-microglobulin, streptavidin, and/or biotin. The streptavidin may be fluorescently labeled. Compositions may comprise tetramers (see e.g., U.S. Pat. No. 5,635,363; Science 274:94-96 (1996)). A tetramer composition comprising an HLA heavy chain, $\beta_2$-microglobulin, streptavidin, and biotin. The streptavidin may be fluorescently labeled. Compositions may also comprise dimers. A dimer composition comprises as MHC molecule and an Ig molecule (see e.g., Proc. Natl. Acad. Sci., USA, 95:7568-73 (1998)).

In some embodiments it may be desirable to include in the compositions of the invention at least one component which primes cytotoxic T lymphocytes. Lipids have been identified as agents capable of priming CTL in vivo against viral antigens. For example, palmitic acid residues can be attached to the ε- and α-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. A preferred composition comprises palmitic acid attached to ε- and α-amino groups of Lys, which is attached via linkage, e.g., Ser-Ser, to the amino terminus of the peptide.

As another example of lipid priming of CTL responses, E. coli lipoproteins, such as tripalmitoyl-S-glycerylcysteinly-seryl-serine ($P_3CSS$) can be used to prime virus specific CTL when covalently attached to an appropriate peptide (see, e.g., Deres, et al., Nature 342:561, 1989). Peptides of the invention can be coupled to $P_3CSS$, for example, and the lipopeptide administered to an individual to specifically prime a CTL response to the target antigen. Moreover, because the induction of neutralizing antibodies can also be primed with $P_3CSS$-conjugated epitopes, two such compositions can be combined to more effectively elicit both humoral and cell-mediated responses.

Another preferred embodiment is a composition comprising one or more peptides of the invention emulsified in IFA.

A highly preferred embodiment of the invention comprises peptides comprising SEQ ID NOs:1-10 of the invention emulsified in IFA.

Compositions of the invention may also comprise CTL and/or HTL peptides. Such CTL and HTL peptides can be modified by the addition of amino acid residues to the termini of a peptide to provide for ease of linking peptides one to another, for coupling to a carrier support or larger peptide, for modifying the physical or chemical properties of the peptide or oligopeptide, or the like. Amino acid residues such as tyrosine, cysteine, lysine, glutamic or aspartic acid, or naturally or unnaturally occurring amino acid residues, can be introduced at the carboxyl- or amino-terminus of the peptide or oligopeptide, particularly class I peptides. However, it is to be noted that modification at the carboxyl terminus of a CTL epitope may, in some cases, alter binding characteristics of the peptide. In addition, the peptide or oligopeptide sequences can differ from the natural sequence by being modified by terminal-$NH_2$ acylation, e.g., by alkanoyl ($C_1$-$C_{20}$) or thioglycolyl acetylation, terminal-carboxyl amidation, e.g., ammonia, methylamine, etc. In some instances these modifications may provide sites for linking to a support or other molecule. CTL and HTL epitopes may comprise additional amino acid residues, such as those described above including spacers.

A further embodiment of a composition in accordance with the invention is an antigen presenting cell that comprises one or more peptides in accordance with the invention. The antigen presenting cell can be a "professional" antigen presenting cell, such as a dendritic cell. The antigen presenting cell can comprise the peptide of the invention by any means known or to be determined in the art. Such means include pulsing of dendritic cells with one or more individual peptides, by nucleic acid administration such as ballistic nucleic acid delivery or by other techniques in the art for administration of nucleic acids, including vector-based, e.g. viral vector, delivery of nucleic acids.

Compositions may comprise carriers. Carriers that can be used with compositions of the invention are well known in the art, and include, e.g., thyroglobulin, albumins such as human serum albumin, tetanus toxoid, polyamino acid residues such as poly L-lysine, poly L-glutamic acid, influenza virus proteins, hepatitis B virus core protein, and the like.

The compositions (e.g. pharmaceutical compositions) can contain a physiologically tolerable diluent such as water, or a saline solution, preferably phosphate buffered saline. Additionally, as disclosed herein, CTL responses can be primed by conjugating peptides of the invention to lipids, such as tri-palmitoyl-S-glyceryl-cysteinyl-seryl-serine ($P_3CSS$).

Compositions of the invention may be pharmaceutically acceptable compositions. Pharmaceutical compositions preferably contain an immunologically effective amount of one or more peptides and/or polynucleotides of the invention, and optionally one or more other components which are pharmaceutically acceptable. A preferred composition comprises one or more peptides of the invention and IFA. A more preferred composition of the invention comprises one or more peptides of the invention, one or more peptides, and IFA.

Upon immunization with a peptide and/or polynucleotide and/or composition in accordance with the invention, via injection (e.g., SC, ID, IM), aerosol, oral, transdermal, transmucosal, intrapleural, intrathecal, or other suitable routes, the immune system of the host responds to the vaccine by an immune response comprising the production of antibodies, CTLs and/or HTLs specific for the desired antigen(s). Consequently, the host becomes at least partially immune to subsequent exposure to the TAA(s), or at least partially resistant to further development of TAA-bearing cells and thereby derives a prophylactic or therapeutic benefit.

Furthermore, the peptides, primers, and epitopes of the invention can be used in any desired immunization or administration regimen; e.g., as part of periodic vaccinations such as annual vaccinations as in the veterinary arts or as in periodic vaccinations as in the human medical arts, or as in a prime-boost regime wherein an inventive vector or recombinant is administered either before or after the administration of the same or of a different epitope of interest or recombinant or vector expressing such as a same or different epitope of interest (including an inventive recombinant or vector expressing such as a same or different epitope of interest), see, e.g., U.S. Pat. Nos. 5,997,878; 6,130,066; 6,180,398; 6,267,965; and 6,348,450. An useful viral vector of the present invention is Modified Vaccinia Ankara (MVA) (e.g., Bavarian Noridic (MVA-BN)).

Recent studies have indicated that a prime boost protocol, whereby immunization with a poxvirus recombinant expressing a foreign gene product is followed by a boost using a purified subunit preparation form of that gene product, elicits an enhanced immune response relative to the response elicited with either product alone. Human volunteers immunized with a vaccinia recombinant expressing the HIV-1 envelope glycoprotein and boosted with purified HIV-1 envelope glycoprotein subunit preparation exhibit higher HIV-1 neutralizing antibody titers than individuals immunized with just the vaccinia recombinant or purified envelope glycoprotein alone (Graham et al., *J. Infect. Dis.*, 167:533-537 (1993); Cooney et al., *Proc. Natl. Acad. Sci. USA*, 90:1882-1886 (1993)). Humans immunized with two injections of an ALVAC-HIV-1 env recombinant (vCP125) failed to develop HIV specific antibodies. Boosting with purified rgp160 from a vaccinia virus recombinant resulted in detectable HIV-1 neutralizing antibodies. Furthermore, specific lymphocyte T cell proliferation to rgp160 was clearly increased by the boost with rgp160. Envelope specific cytotoxic lymphocyte activity was also detected with this vaccination regimen (Pialoux et al., *AIDS Res. and Hum. Retroviruses*, 11:272-381 (1995)). Macaques immunized with a vaccinia recombinant expressing the simian immunodeficiency virus (SW) envelope glycoprotein and boosted with SW envelope glycoprotein from a baculovirus recombinant are protected against SW challenge (Hu et al., *AID Res. and Hum. Retroviruses*, 3:615-620 (1991); Hu et al., *Science* 255:456-459 (1992)). In the same fashion, purified HCMVgB protein can be used in prime-boost protocols with NYVAC or ALVAC-gB recombinants.

In certain embodiments, the polynucleotides are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Feigner et al., *Proc. Natl. Acad. Sci. USA* 84:74137416 (1987), which is herein incorporated by reference); mRNA (Malone et al., *Proc. Natl. Acad. Sci. USA* 86:60776081 (1989), which is herein incorporated by reference); and purified transcription factors (Debs et al., *J. Biol. Chem.* 265:1018910192 (1990), which is herein incorporated by reference), in functional form.

Cationic liposomes are readily available. For example, N-[12,3-dioleyloxy)-propyl]-N,N,N-triethylammonium (DOTMA) liposomes are particularly useful and are available under the trademark Lipofectin®, from Invitrogen, Carlsbad, Calif. (See, also, Feigner et al., *Proc. Natl. Acad. Sci. USA* 84:74137416 (1987)). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 for a description of the synthesis of DOTAP (1,2-bis(oleoyloxy)-3-(trimethylammonio)propane) liposomes. Preparation of DOTMA liposomes is explained in the literature, see, e.g., P. Feigner et al., *Proc. Natl. Acad. Sci. USA* 84:74137417. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially available dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15° C. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome nucleic acid complexes are prepared using methods well known in the art. See, e.g., Straubinger et al., *Methods of Immunology* 101:512527 (1983). For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., *Biochim. Biophys. Acta* 394:483 (1975); Wilson et al., *Cell* 17:77 (1979)); ether injection (Deamer, D. and Bangham, A., *Biochim. Biophys. Acta* 443:629 (1976); Ostro et al., *Biochem. Biophys. Res. Commun.* 76:836 (1977); Fraley et al., *Proc. Natl. Acad. Sci. USA* 76:3348 (1979)); detergent dialysis (Enoch, H. and Strittmatter, P., *Proc. Natl. Acad. Sci. USA* 76:145 (1979)); and reversephase evaporation (REV) (Fraley et al., *J. Biol. Chem.* 255:10431 (1980); Szoka, F. and Papahadjopoulos, D., *Proc: Natl. Acad. Sci. USA* 75:145 (1978); SchaeferRidder et al., *Science* 215:166 (1982)).

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 reports on the injection of genetic material, complexed with cationic liposome carriers, into mice. U.S. Pat. Nos. 4,897,355, 4,946,787, 5,049,386, 5,459,127, 5,589,466; 5,693,622, 5,580,859, 5,703,055, and international publication no., WO 94/9469 provide cationic lipids for use in transfecting DNA into cells and mammals. U.S. Pat. Nos. 5,589,466, 5,693,622, 5,580,859, 5,703,055, and international publication no. WO 94/9469 provide methods for delivering DNA-cationic lipid complexes to mammals.

Binding Affinity of Epitopes and Analogs for HLA Molecules

As indicated herein, the large degree of HLA polymorphism is an important factor to be taken into account with the epitope-based approach to developing therapeutics and diagnostics. To address this factor, epitope selection encompassing identification of peptides capable of binding at high or intermediate affinity to multiple HLA molecules is preferably utilized, most preferably these epitopes bind at high or intermediate affinity to two or more allele-specific HLA molecules. However, in some embodiments, it is preferred that all epitopes in a given composition bind to the alleles of a single HLA supertype or a single HLA molecule.

Epitopes and analogs of the invention preferably include those that have an $IC_{50}$ or binding affinity value for a class I HLA molecule(s) of 500 nM or better (i.e., the value is ≤500 nM). In certain embodiments of the invention, peptides of interest have an $IC_{50}$ or binding affinity value for a class I HLA molecule(s) of 200 nM or better. In certain embodiments of the invention, peptides of interest, have an $IC_{50}$ or binding affinity value for a class I HLA molecule(s) of 100 nM or better. If HTL epitopes are included, they preferably are HTL epitopes that have an $IC_{50}$ or binding affinity value for class II HLA molecules of 1000 nM or better, (i.e., the value is ≤1,000 nM). For example, peptide binding is assessed by testing the capacity of a candidate peptide to bind to a purified HLA molecule in vitro. Peptides exhibiting high or intermediate affinity are then considered for further analysis. Selected peptides are generally tested on other members of the supertype family. In preferred embodiments, peptides that exhibit cross-reactive binding are then used in cellular screening analyses or vaccines.

The relationship between binding affinity for HLA class I molecules and immunogenicity of discrete peptide epitopes on bound antigens was determined for the first time by inventors at Epimmune. As disclosed in greater detail herein, higher HLA binding affinity is correlated with greater immunogenicity.

Greater immunogenicity can be manifested in several different ways. Immunogenicity corresponds to whether an immune response is elicited at all, and to the vigor of any particular response, as well as to the extent of a population in which a response is elicited. For example, a peptide might elicit an immune response in a diverse array of the population, yet in no instance produce a vigorous response. In accordance with these principles, close to 90% of high binding peptides have been found to elicit a response and thus be "immunogenic," as contrasted with about 50% of the peptides that bind with intermediate affinity. (See, e.g., Schaeffer et al. *Proc. Natl. Acad. Sci., USA* (1988)) High affinity-binding class I peptides generally have an affinity of less than or equal to 100 nM. Moreover, not only did peptides with higher binding affinity have an enhanced probability of generating an immune response, the generated response tended to be more vigorous than the response seen with weaker binding peptides. As a result, less peptide is required to elicit a similar biological effect if a high affinity binding peptide is used rather than a lower affinity one. Thus, in some preferred embodiments of the invention, high affinity binding epitopes are used.

The correlation between binding affinity and immunogenicity was analyzed by the present inventors by two different experimental approaches (see, e.g., Sette, et al., *J. Immunol.* 153:5586-5592 (1994)). In the first approach, the immunogenicity of potential epitopes ranging in HLA binding affinity over a 10,000-fold range was analyzed in HLA-A*0201 transgenic mice. In the second approach, the antigenicity of approximately 100 different hepatitis B virus (HBV)-derived potential epitopes, all carrying A*0201 binding motifs, was assessed by using PBL from acute hepatitis patients. Pursuant to these approaches, it was determined that an affinity threshold value of approximately 500 nM (preferably 50 nM or less) determines the capacity of a peptide epitope to elicit a CTL response. These data are true for class I binding affinity measurements for naturally processed peptides and for synthesized T cell epitopes. These data also indicate the important role of determinant selection in the shaping of T cell responses (see, e.g., Schaeffer et al. *Proc. Natl. Acad. Sci. USA* 86:4649-4653 (1989)).

An affinity threshold associated with immunogenicity in the context of HLA class II (i.e., HLA DR) molecules has also been delineated (see, e.g., Southwood et al. *J. Immunology* 160:3363-3373 (1998), and U.S. Pat. No. 6,413,527, issued Jul. 2, 2002). In order to define a biologically significant threshold of HLA class II binding affinity, a database of the binding affinities of 32 DR-restricted epitopes for their restricting element (i.e., the HLA molecule that binds the epitope) was compiled. In approximately half of the cases (15 of 32 epitopes), DR restriction was associated with high binding affinities, i.e. binding affinity values of 100 nM or less. In the other half of the cases (16 of 32), DR restriction was associated with intermediate affinity (binding affinity values in the 100-1000 nM range). In only one of 32 cases was DR restriction associated with an $IC_{50}$ of 1000 nM or greater. Thus, 1000 nM is defined as an affinity threshold associated with immunogenicity in the context of DR molecules.

Epitope Binding Motifs and Supermotifs

Through the study of single amino acid substituted antigen analogs and the sequencing of endogenously bound, naturally processed peptides, critical residues required for allele-specific binding to HLA molecules have been identified. The presence of these residues in a peptide correlates with both the probability of binding and with binding affinity for HLA molecules.

The identification of motifs and/or supermotifs that correlate with high and intermediate affinity binding is important when identifying immunogenic peptide epitopes for the inclusion in a vaccine. Kast et al. (*J. Immunol.* 152:3904-3912 (1994)) have shown that motif-bearing peptides account for 90% of the epitopes that bind to allele-specific HLA class I molecules. In the Kast study, all possible 9 amino acid long peptides, each overlapping by eight amino acid residues, which cover the entire sequence of the E6 and E7 proteins of human papillomavirus type 16 were generated, which produced 240 peptides. All 240 peptides were evaluated for binding to five allele-specific HLA molecules that are expressed at high frequency among different ethnic groups. This unbiased set of peptides allowed an evaluation of the predictive values of HLA class I motifs. From the set of 240 peptides, 22 peptides were identified that bound to an allele-specific HLA molecule with high or intermediate affinity. Of these 22 peptides, 20 (i.e. 91%) were motif-bearing. Thus, this study demonstrated the value of motifs for identification of peptide epitopes to be included in a vaccine.

Accordingly, the use of motif-based identification techniques identifies approximately 90% of all potential epitopes in a target protein sequence. Without the disclosed motif analysis, the ability to practically identify immunogenic peptide(s) for use in diagnostics or therapeutics is seriously impaired.

Peptides, pharmaceutical compositions and vaccines of the present invention may also comprise epitopes that bind to MHC class II DR molecules. A greater degree of heterogeneity in both size and binding frame position of the motif, relative to the N- and C-termini of the peptide, exists for class II peptide ligands. This increased heterogeneity of HLA class II peptide ligands is due to the structure of the binding groove of the HLA class II molecule which, unlike its class I counterpart, is less physically constricted at both ends. Crystallographic analysis of HLA class II DRB*0101-peptide complexes to identify the residues associated with major binding energy identified those residues complexed with complementary pockets on the DRBl*0101 molecules. An important anchor residue engages the deepest hydrophobic pocket (see, e.g., Madden, D. R. *Ann. Rev. Immunol.* 13:587 (1995)) and is referred to as position 1 (P1). P1 may represent the N-terminal residue of a class II binding peptide epitope, but more typically is flanked towards the N-terminus by one or more residues. Other studies have also pointed to an important role for the peptide residue in the sixth position towards the C-terminus, relative to P1, for binding to various DR molecules. See, e.g., U.S. Pat. No. 5,736,142, and co-pending applications entitled Alteration Of Immune Responses Using Pan DR Binding Peptides, U.S. Ser. No. 09/709,774, filed Nov. 8, 2000 and 09/707,738, filed Nov. 6, 2000.

HLA-A2 Supermotif

Primary anchor specificities for allele-specific HLA-A2.1 molecules (see, e.g., Falk et al., *Nature* 351:290-296 (1991); Hunt et al., *Science* 255:1261-1263 (1992); Parker et al., *J. Immunol.* 149:3580-3587 (1992); Ruppert et al., *Cell* 74:929-937 (1993)) and cross-reactive binding among HLA-A2 and -A28 molecules have been described. (See, e.g., Fruci et al., *Human Immunol.* 38:187-192 (1993); Tanigaki et al., *Human Immunol.* 39:155-162 (1994); del Guercio et al., *J. Immunol.* 154:685-693 (1995); Kast et al., *J. Immunol.* 152:3904-3912 (1994) for reviews of relevant data.) These primary anchor residues define the HLA-A2 supermotif; which when present in peptide ligands corresponds to the ability to bind several different HLA-A2 and -A28 molecules. The HLA-A2 supermotif comprises peptide ligands with L, I, V, M, A, T, or Q as a primary anchor residue at position 2 and L, I, V, M, A, or T as a primary anchor residue at the C-terminal position of the epitope.

The corresponding family of HLA molecules (i.e., the HLA-A2 supertype that binds these peptides) is comprised of at least: A*0201, A*0202, A*0203, A*0204, A*0205, A*0206, A*0207, A*0209, A*0214, A*6802, and A*6901. Other allele-specific HLA molecules predicted to be members of the A2 superfamily are shown in Tables 4D and 6. As explained in detail below, binding to each of the individual allele-specific HLA molecules can be modulated by substitutions at the primary anchor and/or secondary anchor positions, preferably choosing respective residues specified for the supermotif.

HLA-A*0201 Motif

An HLA-A2*0201 motif was determined to be characterized by the presence in peptide ligands of L or M as a primary anchor residue in position 2, and L or V as a primary anchor residue at the C-terminal position of a 9-residue peptide (see, e.g., Falk et al., *Nature* 351:290-296 (1991)) and was further found to comprise an I at position 2 and I or A at the C-terminal position of a nine amino acid peptide (see, e.g., Hunt et al., *Science* 255:1261-1263, Mar. 6, 1992; Parker et al., *J. Immunol.* 149:3580-3587 (1992)) and position 10 of a decamer peptide. The A*0201 allele-specific motif has also been defined by the present inventors to additionally comprise V, A, T, or Q as a primary anchor residue at position 2, and M or T as a primary anchor residue at the C-terminal position of the epitope (see, e.g., Kast et al., *J. Immunol.* 152:3904-3912, 1994).

Thus, the HLA-A*0201 motif comprises peptide ligands with L, I, V, M, A, T, or Q as primary anchor residues at position 2 and L, I, V, M, A, or T as a primary anchor residue at the C-terminal position of the epitope. For this motif-supermotif relationship the preferred and less preferred/tolerated residues that characterize the primary anchor positions of the HLA-A*0201 motif are identical to the residues describing the A2 supermotif. (For reviews of relevant data, see, e.g., del Guercio et al., *J. Immunol.* 154:685-693, 1995; Ruppert et al., *Cell* 74:929-937, 1993; Sidney et al., *Immunol. Today* 17:261-266, 1996; Sette and Sidney, *Curr. Opin. in Immunol.* 10:478-482, 1998). Secondary anchor residues that characterize the A*0201 motif have additionally been defined (see, e.g., Ruppert et al., *Cell* 74:929-937, 1993). These secondary anchors are shown in Tables 4A, 4B, and 4C. Peptide binding to HLA-A*0201 molecules can be modulated by substitutions at primary and/or secondary anchor positions, preferably choosing respective residues specified for the motif.

Motifs Indicative of Class II HTL Inducing Peptide Epitopes

The primary and secondary anchor residues of the HLA class II peptide epitope supermotifs and motifs are summarized in U.S. Pat. Nos. 5,736,142, 5,679,640 and 6,413,935; co-pending applications entitled Alteration Of Immune Responses Using Pan DR Binding Peptides, U.S. Ser. No. 09/709,774, filed Nov. 8, 2000 and 09/707,738, filed Nov. 6, 2000; and PCT publication Nos. WO 95/07707 and WO 97/26784.

Immune Response-Stimulating Peptide Analogs

In general, CTL and HTL responses are not directed against all possible epitopes. Rather, they are restricted to a few "immunodominant" determinants (Zinkemagel, et al., Adv. Immunol. 27:5159, 1979; Bennink, et al., *J. Exp. Med.* 168:19351939, 1988; Rawle, et al., *J. Immunol.* 146:3977-3984, 1991). It has been recognized that immunodominance (Benacerraf, et al., *Science* 175:273-279, 1972) could be explained by either the ability of a given epitope to selectively bind a particular HLA protein (determinant selection theory) (Vitiello, et al., *J. Immunol.* 131:1635, 1983); Rosenthal, et al., *Nature* 267:156-158, 1977), or to be selectively recognized by the existing TCR (T cell receptor) specificities (repertoire theory) (Klein, J., IMMUNOLOGY, THE SCIENCE OF SELF NON-SELF DISCRIMINATION, John Wiley & Sons, New York, pp. 270-310, 1982). It has been demonstrated that additional factors, mostly linked to processing events, can also play a key role in dictating, beyond strict immunogenicity, which of the many potential determinants will be presented as immunodominant (Sercarz, et al., *Annu. Rev. Immunol.* 11:729-766, 1993).

The concept of dominance and subdominance is relevant to immunotherapy of both infectious diseases and malignancies. For example, in the course of chronic viral disease, recruitment of subdominant epitopes can be important for successful clearance of the infection, especially if dominant CTL or HTL specificities have been inactivated by functional tolerance, suppression, mutation of viruses and other mechanisms (Franco, et al., *Curr. Opin. Immunol.* 7:524-531, 1995). In the case of cancer and tumor antigens, CTLs recognizing at least some of the highest binding affinity peptides might be functionally inactivated. Lower binding affinity peptides are preferentially recognized at these times, and may therefore be preferred in therapeutic or prophylactic anti-cancer vaccines.

In particular, it has been noted that a significant number of epitopes derived from known non-viral tumor associated antigens (TAA) bind HLA class I with intermediate affinity ($IC_{50}$ in the 50-500 nM range) rather than at high affinity ($IC_{50}$ of less than 50 nM).

For example, it has been found that 8 of 15 known TAA peptides recognized by tumor infiltrating lymphocytes (TEL) or CTL bound in the 50-500 nM range. (These data are in contrast with estimates that 90% of known viral antigens were bound by HLA class I molecules with $IC_{50}$ of 50 nM or less, while only approximately 10% bound in the 50-500 nM range (Sette, et al., *J. Immunol.*, 153:558-592, 1994). In the cancer setting this phenomenon is probably due to elimination or functional inhibition of the CTL recognizing several of the highest binding peptides, presumably because of T cell tolerization events.

Without intending to be bound by theory, it is believed that because T cells to dominant epitopes may have been clonally deleted, and selecting subdominant epitopes may allow existing T cells to be recruited, which will then lead to a therapeutic or prophylactic response. However, the binding of HLA molecules to subdominant epitopes is often less vigorous than to dominant ones.

Accordingly, there is a need to be able to modulate the binding affinity of particular immunogenic epitopes for one or more HLA molecules, to thereby modulate the immune response elicited by the peptide, for example to prepare analog peptides which elicit a more vigorous response. This ability to modulate both binding affinity and the resulting immune response in accordance with the present invention greatly enhances the usefulness of peptide epitope-based vaccines and therapeutic agents.

Although peptides with suitable cross-reactivity among all alleles of a superfamily are identified by the screening procedures described above, cross-reactivity is not always as complete as possible, and in certain cases procedures to increase cross-reactivity of peptides can be useful; moreover, such procedures can also be used to modify other properties of the peptides such as binding affinity or peptide stability. Having established the general rules that govern cross-reactivity of peptides for HLA alleles within a given motif or supermotif, modification (i.e., analoging) of the structure of peptides of particular interest in order to achieve broader (or otherwise modified) HLA binding capacity can be performed. More specifically, peptides that exhibit the broadest cross-reactivity patterns, can be produced in accordance with the teachings herein. The present concepts related to analog generation are set forth in greater detail in co-pending U.S. Ser. No. 09/226,775 filed 6 Jan. 1999.

In brief, the analoging strategy utilizes the motifs or supermotifs that correlate with binding to certain HLA molecules. Analog peptides can be created by substituting amino acid residues at primary anchor, secondary anchor, or at primary and secondary anchor positions. Generally, analogs are made for peptides that already bear a motif or supermotif. As noted herein, preferred primary and secondary anchor residues of supermotifs and motifs for HLA-A2 class I binding peptides are shown in Tables 4A, 4B, and 4C. For a number of the motifs or supermotifs in accordance with the invention, residues are defined which are deleterious to binding to allele-specific HLA molecules or members of HLA supertypes that bind the respective motif or supermotif (Table 4C). Accordingly, removal of such residues that are detrimental to binding can be performed in accordance with the present invention.

Thus, one strategy to improve the cross-reactivity of peptides within a given supermotif is simply to delete one or more of the deleterious residues present within a peptide and substitute a small "neutral" residue such as Ala (that may not influence T cell recognition of the peptide). An enhanced likelihood of cross-reactivity is expected if, together with elimination of detrimental residues within a peptide, "preferred" residues associated with high affinity binding to an allele-specific HLA molecule or to multiple HLA molecules within a superfamily are inserted.

To ensure that an analog peptide, when used as a vaccine, actually elicits a CTL response to the native epitope in vivo (or, in the case of class II epitopes, elicits helper T cells that cross-react with the wild type peptides), the analog peptide may be used to induce T cells in vitro from individuals of the appropriate HLA allele. Thereafter, the immunized cells' capacity to lyse wild type peptide sensitized target cells is evaluated. Alternatively, evaluation of the cells' activity can be evaluated by monitoring IFN release. Each of these cell monitoring strategies evaluate the recognition of the APC by the CTL. It will be desirable to use as antigen presenting cells, cells that have been either infected, or transfected with the appropriate genes, or, (generally only for class II epitopes, due to the different peptide processing pathway for HLA class II), cells that have been pulsed with whole protein antigens, to establish whether endogenously produced antigen is also recognized by the T cells induced by the analog peptide. It is to be noted that peptide/protein-pulsed dendritic cells can be used to present whole protein antigens for both HLA class I and class U.

Another embodiment of the invention is to create analogs of weak binding peptides, to thereby ensure adequate numbers of cellular binders. Class I binding peptides exhibiting binding affinities of 500-5000 nM, and carrying an acceptable but suboptimal primary anchor residue at one or both positions can be "fixed" by substituting preferred anchor residues in accordance with the respective supertype. The analog peptides can then be tested for binding and/or cross-binding capacity.

Another embodiment of the invention is to create analogs of peptides that are already cross-reactive binders and are vaccine candidates, but which bind weakly to one or more alleles of a supertype. If the cross-reactive binder carries a suboptimal residue (less preferred or deleterious) at a primary or secondary anchor position, the peptide can be analoged by substituting out a deleterious residue and replacing it with a preferred or less preferred one, or by substituting out a less preferred reside and replacing it with a preferred one. The analog peptide can then be tested for cross-binding capacity.

Another embodiment for generating effective peptide analogs involves the substitution of residues that have an adverse impact on peptide stability or solubility in, e.g., a liquid environment. This substitution may occur at any position of the peptide epitope. For example, a cysteine (C) can be substituted in favor of α-amino butyric acid. Due to its chemical nature, cysteine has the propensity to form disulfide bridges and sufficiently alter the peptide structurally so as to reduce binding capacity. Substituting α-amino butyric acid for C not only alleviates this problem, but actually improves binding and crossbinding capability in certain instances (see, e.g., the review by Sette et al., In: *Persistent Viral Infections*, Eds. R. Ahmed and I. Chen, John Wiley & *Sons, England*, 1999). Substitution of cysteine with α-amino butyric acid may occur at any residue of a peptide epitope, i.e. at either anchor or non-anchor positions.

Moreover, it has been shown that in sets of A*0201 motif-bearing peptides containing at least one preferred secondary anchor residue while avoiding the presence of any deleterious secondary anchor residues, 69% of the peptides will bind A*0201 with an $IC_{50}$ less than 500 nM (Ruppert, J. et al. *Cell* 74:929, 1993). The determination of what was a preferred or deleterious residue in Ruppert can be used to generate algorithms. Such algorithms are flexible in that cut-off scores may be adjusted to select sets of peptides with greater or lower predicted binding properties, as desired.

In accordance with the procedures described herein, tumor associated antigen peptide epitopes and analogs thereof that were found to bind HLA-A2 allele-specific molecules and to bind members of the HLA-A2 supertype have been identified.

Furthermore, additional amino acid residues can be added to the termini of a peptide to provide for ease of linking peptides one to another, for coupling to a carrier support or larger peptide, for modifying the physical or chemical properties of the peptide or oligopeptide, or the like. Amino acid residues such as tyrosine, cysteine, lysine, glutamic or aspartic acid, or any naturally occurring or any non-naturally occurring amino acid residues, can be introduced at the C- and/or N-terminus of the peptide or oligopeptide, particularly class I peptides. It is to be noted that modification at the carboxyl terminus of a CTL epitope may, in some cases, alter binding characteristics of the peptide. In addition, the peptide or oligopeptide sequences can differ from the natural sequence by being modified by terminal-$NH_2$ acylation, e.g., by alkanoyl ($C_1$-$C_{20}$) or thioglycolyl acetylation, terminal-carboxyl amidation, e.g., ammonia, methylamine etc. In some instances these modifications may provide sites for linking to a support or other molecule.

Assays to Detect T-Cell Responses

Once HLA binding peptides are identified, they can be tested for the ability to elicit a T-cell response. The preparation and evaluation of motif-bearing peptides are described, e.g., in PCT publications WO 94/20127 and WO 94/03205. Briefly, peptides comprising epitopes from a particular antigen are synthesized and tested for their ability to bind to relevant HLA proteins. These assays may involve evaluation of peptide binding to purified HLA class I molecules in relation to the binding of a radioiodinated reference peptide. Alternatively, cells expressing empty class I molecules (i.e. cell surface HLA molecules that lack any bound peptide) may be evaluated for peptide binding by immunofluorescent staining and flow microfluorimetry. Other assays that may be used to evaluate peptide binding include peptide-dependent class I assembly assays and/or the inhibition of CTL recognition by peptide competition. Those peptides that bind to an HLA class I molecule, typically with an affinity of 500 nM or less, are further evaluated for their ability to serve as targets for CTLs derived from infected or immunized individuals, as well as for their capacity to induce primary in vitro or in vivo CTL responses that can give rise to CTL populations capable of reacting with selected target cells associated with pathology.

Analogous assays are used for evaluation of HLA class II binding peptides. HLA class II motif-bearing peptides that are shown to bind, typically at an affinity of 1000 nM or less, are further evaluated for the ability to stimulate HTL responses.

Conventional assays utilized to detect T cell responses include proliferation assays, lymphokine secretion assays, direct cytotoxicity assays, and limiting dilution assays. For example, antigen-presenting cells that have been incubated with a peptide can be assayed for the ability to induce CTL responses in responder cell populations. Antigen-presenting cells can be normal cells such as peripheral blood mononuclear cells or dendritic cells. Alternatively, mutant, non-human mammalian cell lines that have been transfected with a human class I MHC gene, and that are deficient in their ability to load class I molecules with internally processed peptides, are used to evaluate the capacity of the peptide to induce in vitro primary CTL responses. Peripheral blood mononuclear cells (PBMCs) can be used as the source of CTL precursors. Antigen presenting cells are incubated with peptide, after which the peptide-loaded antigen-presenting cells are then incubated with the responder cell population under optimized culture conditions. Positive CTL activation can be determined by assaying the culture for the presence of CTLs that lyse radio-labeled target cells, either specific peptide-pulsed targets or target cells that express endogenously processed antigen from which the specific peptide was derived. Alternatively, the presence of epitope-specific CTLs can be determined by IFNγ in situ ELISA.

In an embodiment of the invention, directed to diagnostics, a method has been devised which allows direct quantification of antigen-specific T cells by staining with fluorescein-labelled HLA tetrameric complexes (Altman, J. D. et al., *Proc. Natl. Acad. Sci. USA* 90:10330, 1993; Altman, J. D. et al., *Science* 274:94, 1996). Other options include staining for intracellular lymphokines, and interferon release assays or ELISPOT assays. Tetramer staining, intracellular lymphokine staining and ELISPOT assays all appear to be at least 10-fold more sensitive than more conventional assays (Lalvani, A. et al., *J. Exp. Med.* 186:859, 1997; Dunbar, P. R. et *Curr. Biol.* 8:413, 1998; Murali-Krishna, K. et al., *Immunity* 8:177, 1998). Additionally, DimerX technology can be used as a means of quantitation (see, e.g., *Science* 274:94-99 (1996) and *Proc. Natl. Acad. Sci.* 95:7568-73 (1998)).

HTL activation may also be assessed using techniques known to those in the art, such as T cell proliferation or lymphokine secretion (see, e.g. Alexander et al., *Immunity* 1:751-761, 1994).

Alternatively, immunization of HLA transgenic mice can be used to determine immunogenicity of peptide epitopes. Several transgenic mouse strains, e.g., mice with human A2.1, A11 (which can additionally be used to analyze HLA- A3 epitopes), and B7 alleles have been characterized. Other transgenic mice strains (e.g., transgenic mice for HLA A1 and A24) are being developed. Moreover, HLA-DR1 and HLA-DR3 mouse models have been developed. In accordance with principles in the art, additional transgenic mouse models with other HLA alleles are generated as necessary.

Such mice can be immunized with peptides emulsified in Incomplete Freund's Adjuvant; thereafter any resulting T cells can be tested for their capacity to recognize target cells that have been peptide-pulsed or transfected with genes encoding the peptide of interest. CTL responses can be analyzed using cytotoxicity assays described above. Similarly, HTL responses can be analyzed using, e.g., T cell proliferation or lymphokine secretion assays.

Minigenes

A number of different approaches are available which allow simultaneous delivery of multiple epitopes. Nucleic acids encoding multiple epitopes are a useful embodiment of the invention; discrete peptide epitopes or polyepitopic peptides can be encoded. The epitopes to be included in a minigene are preferably selected according to the guidelines set forth in the previous section. Examples of amino acid sequences that can be included in a minigene include: HLA class I epitopes, HLA class II epitopes, a ubiquitination signal sequence, and/or a targeting sequence such as an endoplasmic reticulum (ER) signal sequence to facilitate movement of the resulting peptide into the endoplasmic reticulum.

The use of multi-epitope minigenes is also described in, e.g., co-pending applications U.S. Ser. No. 09/311,784, 09/894,018, 60/419,973, 60/415,463; Ishioka et al., *J. Immunol.* 162:3915-3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding nine dominant HLA-A*0201- and A11-restricted CTL epitopes derived from the polymerase, envelope, and core proteins of HBV and human immunodeficiency virus (HIV), a PADRE® universal helper T cell (HTL) epitope, and an endoplasmic reticulum-translocating signal sequence has been engineered. Immunization of HLA transgenic mice with this plasmid construct resulted in strong CTL induction responses against the nine CTL epitopes tested. This CTL response was similar to that observed with a lipopeptide of known immunogenicity in humans, and significantly greater than immunization using peptides in oil-based adjuvants. Moreover, the immunogenicity of DNA-encoded epitopes in vitro was also correlated with the in vitro responses of specific CTL lines against target cells transfected with the DNA plasmid. These data show that the minigene served: 1.) to generate a CTL response and 2.) to generate CTLs that recognized cells expressing the encoded epitopes. A similar approach can be used to develop minigenes encoding TAA epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous peptide sequence is created. However, to optimize expression and/or immunogenicity, additional elements can be incorporated into the minigene design such as spacer amino acid residues between epitopes. HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention. In one embodiment, spacer amino acid residues between one or more CTL and/or HTL epitopes are designed so as to minimize junctional epitopes that may result from the juxtaposition of 2 CTL and/or HTL epitopes.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope peptide, can then be cloned into a desired expression vector.

Standard regulatory sequences well known to those of skill in the art are preferably included in the vector to ensure expression in the target cells. Several vector elements are desirable: a promoter with a downstream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) CMV-IE promoter. See, e.g., U.S. Pat. Nos. 5,580,859 and 5,589,466 for other suitable promoter sequences.

Optimized peptide expression and immunogenicity can be achieved by certain modifications to a minigene construct. For example, in some cases introns facilitate efficient gene expression, thus one or more synthetic or naturally-occurring introns can be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate bacterial strain, and DNA is prepared using standard techniques. The orientation and DNA sequence of the minigene, as well as all other elements included in the vector, are confirmed using restriction mapping, PCR and/or DNA sequence analysis. Bacterial cells harboring the correct plasmid can be stored as cell banks.

In addition, immunostimulatory sequences (ISSs or CpGs) appear to play a role in the immunogenicity of DNA vaccines. These sequences may be included in the vector, outside the minigene coding sequence to enhance immunogenicity.

In some embodiments, a bi-cistronic expression vector which allows production of both the minigene-encoded epitopes and a second protein (e.g., one that modulates immunogenicity) can be used. Examples of proteins or polypeptides that, if co-expressed with epitopes, can enhance an immune response include cytokines (e.g., IL-2, IL-12, GM-CSF), cytokine-inducing molecules (e.g., LeIF), costimulatory molecules, or pan-DR binding proteins (PADRE®, Epimmune, San Diego, Calif.). Helper T cell (HTL) epitopes such as PADRE® molecules can be joined to intracellular targeting signals and expressed separately from expressed CTL epitopes. This can be done in order to direct HTL epitopes to a cell compartment different than that of the CTL epitopes, one that provides for more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and are grown to saturation in shaker flasks or a bioreactor according to well known techniques. Plasmid DNA is purified using standard bioseparation technologies such as solid phase anion-exchange resins available, e.g., from QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate buffer saline (PBS). This approach, known as "naked DNA," is currently being used for intramuscular (IM) administration in clinical trials. To maximize the immunotherapeutic effects of minigene vaccines, alternative methods of formulating purified plasmid DNA may be used. A variety of such methods have been described, and new techniques may become available. Cationic lipids, glycolipids, and fusogenic liposomes can also be used in the formulation (see, e.g., WO 93/24640; Mannino & Gould-Fogerite, *BioTechniques* 6(7): 682 (1988); U.S. Pat. No. 5,279,833; WO 91/06309; and Feigner, et al., *Proc. Nat'l Acad. Sci. USA* 84:7413 (1987). In addition, peptides and compounds referred to collectively as protective, interactive, non-condensing compounds (PINC) can also be complexed to purified plasmid DNA to influence variables such as stability, intramuscular dispersion, or trafficking to specific organs or cell types.

Known methods in the art can be used to enhance delivery and uptake of a polynucleotide in vivo. For example, the polynucleotide can be complexed to polyvinylpyrrolidone (PVP), to prolong the localized bioavailability of the polynucleotide, thereby enhancing uptake of the polynucleotide by the organisum (see e.g., U.S. Pat. No. 6,040,295; EP 0 465 529; WO 98/17814). PVP is a polyamide that is known to form complexes with a wide variety of substances, and is chemically and physiologically inert.

Target cell sensitization can be used as a functional assay of the expression and HLA class I presentation of minigene-encoded epitopes. For example, the plasmid DNA is introduced into a mammalian cell line that is a suitable target for standard CTL chromium release assays. The transfection method used will be dependent on the final formulation; electroporation can be used for "naked" DNA, whereas cationic lipids or DNA:PVP compositions allow direct in vitro transfection. A plasmid expressing green fluorescent protein (GFP) can be co-transfected to allow enrichment of transfected cells using fluorescence activated cell sorting (FACS). The transfected cells are then chromium-51 ($^{51}$Cr) labeled and used as targets for epitope-specific CTLs. Cytolysis of the target cells, detected by $^{51}$Cr release, indicates both the production and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (IP) for lipid-complexed DNA). Eleven to twenty-one days after immunization, splenocytes are harvested and restimulated for one week in the presence of peptides encoding each epitope being tested. Thereafter, for CTLs, standard assays are conducted to determine if there is cytolysis of peptide-loaded, $^{51}$Cr-labeled target cells. Once again, lysis of target cells that were exposed to epitopes corresponding to those in the minigene, demonstrates DNA vaccine function and induction of CTLs. Immunogenicity of HTL epitopes is evaluated in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment for ballistic delivery, DNA can be adhered to particles, such as gold particles.

Vaccine Compositions

Vaccines that contain an immunologically effective amount of one or more peptides or polynucleotides of the invention are a further embodiment of the invention. The peptides can be delivered by various means or formulations, all collectively referred to as "vaccine" compositions. Such vaccine compositions, and/or modes of administration, can include, for example, naked DNA, DNA formulated with PVP, DNA in cationic lipid formulations; lipopeptides (e.g., Vitiello, A. et al., *J. Clin. Invest.* 95:341, 1995), DNA or peptides, encapsulated e.g., in poly(DL-lactide-co-glycolide) ("PLG") microspheres (see, e.g., Eldridge, et al., *Molec. Inzmunol.* 28:287-294, 1991: Alonso et al., *Vaccine* 12:299-306, 1994; Jones et al., *Vaccine* 13:675-681, 1995); peptide compositions contained in immune stimulating complexes (ISCOMS) (see, e.g., Takahashi et al., *Nature* 344:873-875, 1990; Hu et al., *Clin Exp Immunol.* 113:235-243, 1998); multiple antigen peptide systems (MAPS) (see e.g., Tarn, J. P., *Proc. Natl. Acad. Sci. U.S.A.* 85:5409-5413, 1988; Tam, J. P *J. Immunol. Methods* 196:17-32, 1996); viral, bacterial, or, fungal delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990); particles of viral or synthetic origin (e.g., Kofler, N. et al, *J. Immunol. Methods.* 192:25, 1996; Eldridge, J. H. et al., *Sem. Henzatol.* 30:16, 1993; Falo, L. D., Jr. et al., *Nature Med.* 7:649, 1995); adjuvants (e.g., incomplete freund's adjuvant) (Warren, H. S., Vogel, F. R., and Chedid, L. A. *Annu. Rev. Immunol.* 4:369, 1986; Gupta, R. K. et al., *Vaccine* 11:293, 1993); liposomes (Reddy, R. et al., *J. Immunol.* 148:1585, 1992; Rock, K. L., *Immunol Today* 17:131, 1996); or, particle-absorbed DNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993), etc. Toxin-targeted delivery technologies, also known as receptor mediated targeting, such as those of Avant Immunotherapeutics, Inc. (Needham, Mass.) or attached to a stress protein, e.g., HSP 96 (Stressgen Biotechnologies Corp., Victoria, BC, Canada) can also be used.

Vaccines of the invention comprise nucleic acid mediated modalities. DNA or RNA encoding one or more of the peptides of the invention can be administered to a patient. This approach is described, for instance, in Wolff et. al., *Science* 247:1465 (1990) as well as U.S. Pat. Nos. 5,580,859; 5,589, 466; 5,804,566; 5,739,118; 5,736,524; 5,679,647; and, WO 98/04720. Examples of DNA-based delivery technologies include "naked DNA", facilitated ((i.e., non-"naked DNA") e.g., facilitated by combination with bupivicaine, polymers (e.g., PVP), peptide-mediated) delivery, cationic lipid complexes, and particle-mediated ("gene gun") or pressure-mediated delivery (see, e.g., U.S. Pat. No. 5,922,687). Accordingly, peptide vaccines of the invention can be expressed by viral or bacterial vectors. Examples of expression vectors include attenuated viral hosts, such as vaccinia or fowlpox. For example, vaccinia virus is used as a vector to express nucleotide sequences that encode the peptides of the invention (e.g., MVA). Upon introduction into an acutely or chronically infected host or into a non-infected host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., *Nature* 351:456-460 (1991). A wide variety of other vectors useful for therapeutic administration or immunization of the peptides of the invention, e.g. adeno and adeno-associated virus vectors, alpha virus vectors, retroviral vectors, *Salmonella typhi* vectors, detoxified anthrax toxin vectors, and the like, are apparent to those skilled in the art from the description herein.

Furthermore, vaccines in accordance with the invention can comprise one or more peptides of the invention. Accordingly, a peptide can be present in a vaccine individually; alternatively, the peptide can exist as a homopolymer comprising multiple copies of the same peptide, or as a heteropolymer of various peptides. Polymers have the advantage of increased probability for immunological reaction and, where different peptide epitopes are used to make up the polymer, the ability to induce antibodies and/or T cells that react with different antigenic determinants of the antigen targeted for an immune response. The composition may be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acid residues such as poly L-lysine, poly L-glutamic acid, influenza virus proteins, hepatitis B virus core protein, and the like The vaccines can contain a physiologically tolerable diluent such as water, or a saline solution, preferably phosphate buffered saline. Generally, the vaccines also include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glyceryl-cysteinyl-seryl-serine ($P_3CSS$).

Upon immunization with a peptide composition in accordance with the invention, via injection (e.g., SC, ID, IM), aerosol, oral, transdermal, transmucosal, intrapleural, intrathecal, or other suitable routes, the immune system of the host responds to the vaccine by producing antibodies, CTLs and/or HTLs specific for the desired antigen. Consequently, the host becomes at least partially immune to subsequent exposure to the TAA, or at least partially resistant to further development of TAA-bearing cells and thereby derives a prophylactic or therapeutic benefit.

In certain embodiments, components that induce T cell responses are combined with components that induce antibody responses to the target antigen of interest. A preferred embodiment of such a composition comprises class I and class II epitopes in accordance with the invention. Alternatively, a composition comprises a class I and/or class II epitope in accordance with the invention, along with a PADRE® molecule (Epimmune, San Diego, Calif.).

Vaccines of the invention can comprise antigen presenting cells, such as dendritic cells, as a vehicle to present peptides of the invention. For example, dendritic cells are transfected, e.g., with a minigene construct in accordance with the invention, in order to elicit immune responses. Minigenes are discussed in greater detail in a following section. Vaccine compositions can be created in vitro, following dendritic cell mobilization and harvesting, whereby loading of dendritic cells occurs in vitro.

The vaccine compositions of the invention may also be used in combination with antiviral drugs such as interferon-$\alpha$, or immune adjuvants such as IL-12, GM-CSF, etc.

Preferably, the following principles are utilized when selecting epitope(s) and/or analogs for inclusion in a vaccine, either peptide based or nucleic acid-based formulations. Exemplary epitopes and analogs that may be utilized in a vaccine to treat or prevent TAA-associated disease are set out in Table 3. Each of the following principles can be balanced in order to make the selection. When multiple epitopes are to be used in a vaccine, the epitopes may be, but need not be, contiguous in sequence in the native antigen from which the epitopes are derived. Such multiple epitotes can refer to the order of epitopes within a peptide, or to the selection of epitopes that come from the same region, for use in either individual peptides or in a multi-epitopic peptide.

1.) Epitopes and/or analogs are selected which, upon administration, mimic immune responses that have been observed to be correlated with prevention or clearance of TAA-expressing tumors. For HLA Class I, this generally includes 34 epitopes and/or analogs from at least one TAA.

2.) Epitopes and/or analogs are selected that have the requisite binding affinity established to be correlated with immunogenicity: for HLA Class I an $IC_{50}$ of 500 nM or less, or for Class II an $IC_{50}$ of 1000 nM or less. For HLA Class I it is presently preferred to select a peptide having an $IC_{50}$ of 200 nM or less, as this is believed to better correlate not only to induction of an immune response, but to in vitro tumor cell killing as well. For HLA A1 and A24, it is especially preferred to select a peptide having an $IC_{50}$ of 100 nM or less.

3.) Supermotif bearing-epitopes and/or analogs, or a sufficient array of allele-specific motif-bearing epitopes and/or analogs, are selected to give broad population coverage. In general, it is preferable to have at least 80% population coverage. A Monte Carlo analysis, a statistical evaluation known in the art, can be employed to assess the breadth of population coverage.

4.) For cancer-related antigens, it can be preferable to select analogs instead of or in addition to epitopes, because the patient may have developed tolerance to the native epitope.

5.) Of particular relevance are "nested epitopes." Nested epitopes occur where at least two epitopes overlap in a given peptide sequence. For example, a nested epitope can be a fragment of an antigen from a region that contains multiple epitopes that are overleapping, or one epitope that is completely encompassed by another, e.g., A2 peptides MAGE3.159 and MAGE3.160 are nested. A peptide comprising "transcendent nested epitopes" is a peptide that has both HLA class I and HLA class II epitopes in it. When providing nested epitopes, it is preferable to provide a sequence that has the greatest number of epitopes per provided sequence. Preferably, one avoids providing a peptide that is any longer than the amino terminus of the amino terminal epitope and the carboxyl terminus of the carboxyl terminal epitope in the peptide. When providing a sequence comprising nested epitopes, it is important to evaluate the sequence in order to insure that it does not have pathological or other deleterious biological properties; this is particularly relevant for vaccines directed to infectious organisms.

6.) If a protein with multiple epitopes or a polynucleotide (e.g., minigene) is created, an objective is to generate the smallest peptide that encompasses the epitopes of interest. This principle is similar, if not the same as that employed when selecting a peptide comprising nested epitopes. However, with an artificial peptide comprising multiple epitopes, the size minimization objective is balanced against the need to integrate any spacer sequences between epitopes in the polyepitopic protein. Spacer amino acid residues can be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

The principles are the same, except junctional epitopes applies to the sequences surrounding the epitope. One must also take care with other sequences in construct to avoid immune response.

T Cell Priming Materials

In some embodiments it may be desirable to include in the pharmaceutical compositions of the invention at least one component which primes cytotoxic T lymphocytes. Lipids have been identified as agents capable of facilitating the priming in vitro-CTL response against viral antigens. For example, palmitic acid residues can be attached to the ε- and α-amino groups of a lysine residue and then linked to an immunogenic peptide. One or more linking moieties can be used such as Gly, Gly-Gly-, Ser, Ser-Ser, or the like. The lipidated peptide can then be administered directly in a micelle or particle, incorporated into a liposome, or emulsified in an adjuvant, e.g., incomplete Freund's adjuvant. A preferred immunogenic composition comprises palmitic acid attached to ε- and α-amino groups of Lys via a linking moiety, e.g., Ser-Ser, added to the amino terminus of an immunogenic peptide.

In another embodiment of lipid-facilitated priming of CTL responses, E. coli lipoproteins, such as tripalmitoyl-S-glyceryl-cysteinyl-seryl-serine ($P_3CSS$) can be used to prime CTL when covalently attached to an appropriate peptide. (See, e.g., Deres, et al., Nature 342:561, 1989). Thus, peptides of the invention can be coupled $P_3CSS$, and the lipopeptide administered to an individual to specifically prime a CTL response to the target antigen. Moreover, because the induction of neutralizing antibodies can also be primed with $P_3CSS$-conjugated epitopes, two such compositions can be combined to elicit both humoral and cell-mediated responses.

Dendritic Cells Pulsed with CTL and/or HTL Peptides

An embodiment of a vaccine composition in accordance with the invention comprises ex vivo administrations of a cocktail of epitope-bearing peptides to PBMC, or isolated DC therefrom, from the patient's blood. A pharmaceutical to facilitate harvesting of DC can be used, such as Progenipoietin™ (Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes in HLA molecules on their surfaces.

The DC can be pulsed ex vivo with a cocktail of peptides, some of which stimulate CTL responses to one or more antigens of interest, e.g., tumor associated antigens (TAA) such as HER2/neu, p53, MAGE 2, MAGE3, and/or carcinoembryonic antigen (CEA). Collectively, these TAA are associated with breast, colon and lung cancers. Optionally, a helper T cell (HTL) peptide such as PADRE®, can be included to facilitate the CTL response. Thus, a vaccine in accordance with the invention comprising epitopes from HER2/neu, p53, MAGE 2, MAGE3, and carcinoembryonic antigen (CEA) is used to treat minimal or residual disease in patients with malignancies such as breast, colon, lung or ovarian cancer; any malignancies that bear any of these TAAs can also be treated with the vaccine. A TAA vaccine can be used following debulking procedures such as surgery, radiation therapy or chemotherapy, whereupon the vaccine provides the benefit of increasing disease free survival and overall survival in the recipients.

Thus, in preferred embodiments, a vaccine of the invention is a product that treats a majority of patients across a number of different tumor types. A vaccine comprising a plurality of epitopes, preferably supermotif-bearing epitopes, offers such an advantage.

Diagnostic and Prognostic Uses

In one embodiment of the invention, HLA class I and class II binding peptides can be used as reagents to evaluate an immune response. Preferably, the following principles are utilized when selecting an epitope(s) and/or analog(s) for diagnostic, prognostic and similar uses. Potential principles include having the binding affinities described earlier, and/or matching the HLA-motif/supermotif of a peptide with the HLA-type of a patient.

The evaluated immune response can be induced by any immunogen. For example, the immunogen may result in the production of antigen-specific CTLs or HTLs that recognize the peptide epitope(s) employed as the reagent. Thus, a peptide of the invention may or may not be used as the immunogen. Assay systems that can be used for such analyses include tetramer-based protocols (e.g., DimerX technology (see, e.g., Science 274:94-99 (1996) and Proc. Natl. Acad. Sci. 95:7568-73 (1998)), staining for intracellular lymphokines, interferon release assays, or ELISPOT assays.

For example, following exposure to a putative immunogen, a peptide of the invention can be used in a tetramer staining assay to assess peripheral blood mononuclear cells for the presence of any antigen-specific CTLs. The HLA-tetrameric complex is used to directly visualize antigen-specific CTLs and thereby determine the frequency of such antigen-specific CTLs in a sample of peripheral blood mononuclear cells (see, e.g., Ogg et al., Science 279:2103-2106, 1998; and Altman et al., Science 174:94-96, 1996).

A tetramer reagent comprising a peptide of the invention is generated as follows: A peptide that binds to an HLA molecule is refolded in the presence of the corresponding HLA heavy chain and $\beta_2$-microglobulin to generate a trimolecular complex. The complex is biotinylated at the carboxyl terminal end of the HLA heavy chain, at a site that was previously engineered into the protein. Tetramer formation is then induced by adding streptavidin. When fluorescently labeled streptavidin is used, the tetrameric complex is used to stain antigen-specific cells. The labeled cells are then readily identified, e.g., by flow cytometry. Such procedures are used for diagnostic or prognostic purposes; the cells identified by the procedure can be used for therapeutic purposes.

Peptides of the invention are also used as reagents to evaluate immune recall responses. (see, e.g., Bertoni et al., J. Clin. Invest. 100:503-513, 1997 and Penna et al., J. Exp. Med. 174:1565-1570, 1991.) For example, a PBMC sample from an individual expressing a disease-associated antigen (e.g. a tumor-associated antigen such as CEA, p53, MAGE2/3, HER2neu, or an organism associated with neoplasia such as HPV or HSV) can be analyzed for the presence of antigen-specific CTLs or HTLs using specific peptides. A blood sample containing mononuclear cells may be evaluated by cultivating the PBMCs and stimulating the cells with a peptide of the invention. After an appropriate cultivation period, the expanded cell population may be analyzed, for example, for CTL or for HTL activity.

Thus, the peptides can be used to evaluate the efficacy of a vaccine. PBMCs obtained from a patient vaccinated with an immunogen may be analyzed by methods such as those described herein. The patient is HLA typed, and peptide epitopes that are bound by the HLA molecule(s) present in that patient are selected for analysis. The immunogenicity of the vaccine is indicated by the presence of CTLs and/or HTLs directed to epitopes present in the vaccine.

The peptides of the invention may also be used to make antibodies, using techniques well known in the art (see, e.g. CURRENT PROTOCOLS IN IMMUNOLOGY, Wiley/Greene, NY; and *Antibodies A Laboratory Manual Harlow*, Harlow and Lane, Cold Spring Harbor Laboratory Press, 1989). Such antibodies are useful as reagents to determine the presence of disease-associated antigens. Antibodies in this category include those that recognize a peptide when bound by an HLA molecule, i.e., antibodies that bind to a peptide-MHC complex.

Administration for Therapeutic or Prophylactic Purposes

The peptides and polynucleotides of the present invention, including compositions thereof, are useful for administration to mammals, particularly humans, to treat and/or prevent disease. In one embodiment, peptides, polynucleotides, or vaccine compositions (peptide or nucleic acid) of the invention are administered to a patient who has a malignancy associated with expression of one or more TAAs, or to an individual susceptible to, or otherwise at risk for developing TAA-related disease. Upon administration an immune response is elicited against the TAAs, thereby enhancing the patient's own immune response capabilities. In therapeutic applications, peptide and/or nucleic acid compositions are administered to a patient in an amount sufficient to elicit an effective immune response to the TAA-expressing cells and to thereby cure, arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

In certain embodiments, a method of treating cancer is provided. In some cases, the treatment of cancer may include the treatment of solid tumors or the treatment of metastasis. Metastasis is the form of cancer wherein the transformed or malignant cells are traveling and spreading the cancer from one site to another. The cancer can be of the colon, non-small cell lung cancer ("NSCLC"), the breast, the ovary, the kidney, the rectum, head and neck (including but not limited to the nasal and oral cavities), the prostate, the pancreas, small cell lung cancer, the uterus, the bladder, the thyroid, the skin (including, but not limited to, malignant melanoma, basal cell carcinoma, squamous cell carcinoma, Karposi's sarcoma, moles dysplastic nevi, lipoma, angioma, dermatofibroma, keloids, psoriasis, and metastatic melanoma), breast, brain, cervical carcinomas, testicular carcinomas, etc. More particularly, cancers may include, but are not limited to the following organs or systems: cardiac, lung, gastrointestinal, genitourinary tract, liver, bone, nervous system, gynecological, hematologic, skin, and adrenal glands. More particularly, the methods herein can be used for treating gliomas (Schwannoma, glioblastoma, astrocytoma), neuroblastoma, pheochromocytoma, paraganlioma, meningioma, adrenalcortical carcinoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia.

In preferred embodiments, the cancer to be treated by the present invention is colorectal cancer, non-small cell lung cancer ("NSCLC"), breast cancer, ovarian cancer, renal cancer, prostate cancer, cervical cancer, head and/or neck cancer, endometrial cancer, pancreatic cancer, and/or esophageal cancer.

In preferred embodiments, the cancer to be treated by the present invention is colorectal cancer, non-small cell lung cancer ("NSCLC"), breast cancer, and/or ovarian cancer. In certain other preferred embodiments, the cancer is a cancer of the head and/or neck. The term "cancerous cell" as provided herein, includes a cell afflicted by any one of the cancerous conditions provided herein, or any cancer.

In certain embodiments, the present invention may also be used to treat diseases associated with increased cell survival, or the inhibition of apoptosis, including cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection.

In certain embodiments, the invention is used to treat additional diseases or conditions associated with increased cell survival including, but not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angio sarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

The vaccine compositions of the invention can be used purely as prophylactic agents. Generally the dosage for an initial prophylactic immunization generally occurs in a unit dosage range where the lower value is about 1, 5, 50, 500, or 1000 µg of peptide and the higher value is about 10,000; 20,000; 30,000; or 50,000 µg of peptide. Dosage values for a human typically range from about 500 µg to about 50,000 µg of peptide per 70 kilogram patient. This is followed by boosting dosages of between about 1.0 µg to about 50,000 µg of peptide, administered at defined intervals from about four weeks to six months after the initial administration of vaccine. The immunogenicity of the vaccine may be assessed by measuring the specific activity of CTL and HTL obtained from a sample of the patient's blood.

As noted above, peptides comprising CTL and/or HTL epitopes of the invention induce immune responses when presented by HLA molecules and contacted with a CTL or HTL specific for an epitope comprised by the peptide. The manner in which the peptide is contacted with the CTL or HTL is not critical to the invention. For instance, the peptide can be contacted with the CTL or HTL either in vitro or in vivo. If the contacting occurs in vivo, peptide can be administered directly, or in other forms/vehicles, e.g., DNA vectors encoding one or more peptides, viral vectors encoding the peptide(s), liposomes, antigen presenting cells such as dendritic cells, and the like.

Accordingly, for pharmaceutical compositions of the invention in the form of peptides or polypeptides, the peptides or polypeptides can be administered directly. Alternatively, the peptide/polypeptides can be administered indirectly presented on APCs, or as DNA encoding them. Furthermore, the peptides or DNA encoding them can be administered individually or as fusions of one or more peptide sequences.

For therapeutic use, administration should generally begin at the first diagnosis of TAA-related disease. This is followed by boosting doses at least until symptoms are substantially abated and for a period thereafter. In chronic disease states, loading doses followed by boosting doses may be required.

The dosage for an initial therapeutic immunization generally occurs in a unit dosage range where the lower value is about 1, 5, 50, 500, or 1,000 µg of peptide and the higher value is about 10,000; 20,000; 30,000; or 50,000 µg of peptide. Dosage values for a human typically range from about 500 µg to about 50,000 µg of peptide per 70 kilogram patient. Boosting dosages of between about 1.0 µg to about 50,000 µg of peptide, administered pursuant to a boosting regimen over weeks to months, can be administered depending upon the patient's response and condition. Patient response can be determined by measuring the specific activity of CTL and HTL obtained from the patient's blood.

In certain embodiments, peptides and compositions of the present invention are used in serious disease states. In such cases, as a result of the minimal amounts of extraneous substances and the relative nontoxic nature of the peptides, it is possible and may be desirable to administer substantial excesses of these peptide compositions relative to these stated dosage amounts.

For treatment of chronic disease, a representative dose is in the range disclosed above, namely where the lower value is about 1, 5, 50, 500, or 1,000 µg of peptide and the higher value is about 10,000; 20,000; 30,000; or 50,000 µg of peptide, preferably from about 500 µg to about 50,000 µg of peptide per 70 kilogram patient. Initial doses followed by boosting doses at established intervals, e.g., from four weeks to six months, may be required, possibly for a prolonged period of time to effectively immunize an individual. In the case of chronic disease, administration should continue until at least clinical symptoms or laboratory tests indicate that the disease has been eliminated or substantially abated, and for a follow-up period thereafter. The dosages, routes of administration, and dose schedules are adjusted in accordance with methodologies known in the art.

The pharmaceutical compositions for therapeutic treatment are intended for parenteral, topical, oral, intrathecal, or local administration. Preferably, the pharmaceutical compositions are administered parentally, e.g., intravenously, subcutaneously, intradermally, or intramuscularly.

Thus, in a preferred embodiment the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances or pharmaceutical excipients as may be required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of the peptide composition is typically included in a pharmaceutical composition that also comprises a human unit dose of an acceptable carrier, preferably an aqueous carrier, and is administered in a volume of fluid that is known by those of skill in the art to be used for administration of such compositions to humans (see, e.g., *Remington's Pharmaceutical Sciences*, $17^{th}$ Edition, A. Gennaro, Editor, Mack Publishing Co., Easton, Pa., 1985).

The peptides of the invention can also be administered via liposomes, which serve to target the peptides to a particular tissue, such as lymphoid tissue, or to target selectively to infected cells, as well as to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells (such as monoclonal antibodies which bind to the CD45 antigen) or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting compositions of the invention to cells of the immune system, a ligand can be incorporated into the liposome, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, often at a concentration of 25%-75%.

For aerosol administration, the immunogenic peptides are preferably supplied in finely divided form, along with a surfactant and propellant. Typical percentages of peptides are 0.01%-20% by weight, often 1%-10%. The surfactant must, of course, be pharmaceutically acceptable, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant, although an atomizer may be used in which no propellant is necessary and other percentages are adjusted accordingly. A carrier can also be included, e.g., lecithin for intranasal delivery.

Antigenic peptides of the invention have been used to elicit a CTL and/or HTL response ex vivo, as well. The resulting CTLs or HTLs can be used to treat chronic infections, or tumors in patients that do not respond to other conventional forms of therapy, or who do not respond to a therapeutic peptide or nucleic acid vaccine in accordance with the invention. Ex vivo CTL or HTL responses to a particular antigen (infectious or tumor-associated) are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (an infected cell or a tumor cell).

Kits

The peptide and nucleic acid compositions of this invention can be provided in kit form together with instructions for vaccine administration. Typically the kit would include desired composition(s) of the invention in a container, preferably in unit dosage form and instructions for administration. For example, a kit would include an APC, such as a dendritic cell, previously exposed to and now presenting peptides of the invention in a container, preferably in unit dosage form together with instructions for administration. An alternative kit would include a minigene construct with desired nucleic acids of the invention in a container, preferably in unit dosage form together with instructions for administration. Lymphokines such as IL-2 or IL-12 may also be included in the kit. Other kit components that may also be desirable include, for example, a sterile syringe, booster dosages, and other desired excipients.

The invention will be described in greater detail by way of specific examples. The following examples are offered for illustrative purposes, and are not intended to limit the invention in any manner. Those of skill in the art will readily recognize a variety of non-critical parameters that can be changed or modified to yield alternative embodiments in accordance with the invention.

EXAMPLES

Example 1

Selection of Tumor Associated Antigens

Because the A2 supertype is broadly expressed in the population (39-49%), peptides which bind to this family of molecules provide a reasonable basis for peptide-based vaccines. While the A2 vaccine targets patients that express HLA-A2 molecules, the approach can be readily extended to include peptide(s) that bind to additional alleles or supertype groups thereof (see, e.g., U.S. Provisional Application No. 60/432, 017, filed 10 Dec. 2002; which is herein incorporated by reference in its entirety).

Whole proteins often induce an immune response limited to specific epitopes that may be ineffective in mediating effective anti-tumor immune responses (Disis et al., *J. Immunology* 156:3151-3158 (1996); Manca et al., *J. Immunology* 146: 1964-1971 (1991)). An epitope-based vaccine circumvents this limitation through the identification of peptide epitopes embedded in TAAs. Exemplary TAAs are set forth in Table 3.

Peptides were evaluated based upon MHC binding motifs, on the capacity to bind MHC molecules, and the ability to activate tumor-reactive CTL in vitro using lymphocyte cultures from normal individuals. This approach has several advantages. First, it does not require the isolation of patient-derived cells such as CTL or tumor cells. Secondly, the identification of epitopes that stimulate CTL in normal individuals permits the identification of a broad range of epitopes, including subdominant as well as dominant epitopes.

Four tumor-associated antigens, CEA, p53, MAGE 2/3 and HER2/neu, are expressed in various tumor types (Kawashima et al., *Human Immunology* 59:1-14 (1998); Tomlinson, et al., *Advanced Drug Delivery Reviews*, Vol. 32(3) (6 Jul. 1998)). In a preferred embodiment, a vaccine comprises epitopes (as one or more peptides or as nucleic acids encoding them) from among these four, or any other, TAAs. Accordingly, this vaccine induces CTL responses against several major cancer types.

Carcinoembryonic antigen is a 180 kD mw cell surface and secreted glycoprotein overexpressed on most human adenocarcinomas. These include colon, rectal, pancreatic and gastric (Muraro, 1985) as well as 50% of breast (Steward, 1974) and 70% of non-small cell lung carcinomas (Vincent, 1978). This antigen is also expressed on normal epithelium and in some fetal tissue (Thompson, 1991).

The HER2/neu antigen (185 kDa) is a transmembrane glycoprotein with tyrosine kinase activity whose structure is similar to the epidermal growth factor receptor (Coussens, 1985; Bargmann, 1986; Yamamoto, 1986). Amplification of the HER2/neu gene and/or overexpression of the associated protein have been reported in many human adenocarcinomas of the breast (Slamon, 1987 and 1989; Borg, 1990), ovary (Slamon, 1989), uterus (Berchuck, 1991; Lukes, 1994), prostate (Kuhn, 1993; Sadasivan, 1993), stomach (Yonemura, 1991; Kameda, 1990; Houldsworth, 1990), esophagus (Houldsworth, 1990), pancreas (Yamanaka, 1993), kidney (Weidner, 1990) and lung (Kern, 1990; Rachwal, 1995).

The MAGE, melanoma antigen genes, are a family of related proteins that were first described in 1991. Van der Bruggen and co-workers were able to identify the MAGE gene after isolating CTLs from a patient who demonstrated spontaneous tumor regression. These CTLs recognized melanoma cell lines as well as tumor lines from other patients all expressing the same HLA-A1 restricted gene (van der Bruggen, 1991; De Plaen, 1994). The MAGE genes are expressed in metastatic melanomas (Brasseur, 1995), non-small lung (Weynants, 1994), gastric (Inoue, 1995), hepatocellular (Chen, 1999), renal (Yamanaka, 1998) colorectal (Mori, 1996), and esophageal (Quillien, 1997) carcinomas as wells as tumors of the head and neck (Lee, 1996), ovaries (Gillespie, 1998; Yamada, 1995), bladder (Chaux, 1998) and bone (Sudo, 1997). They are also expressed on normal tissue, specifically placenta and male germ cells (De Plaen, 1994). However, these normal cells do not express MHC Class I molecules and therefore do not present MAGE peptides on their surface.

In this study and previous work to identify A2 superfamily epitopes (Kawashima, 1998), MAGE-2 and MAGE-3 were considered a single TAA, based on the expression patterns and predicted primary amino acid sequences of the two genes. These two members of the MAGE family appear to be coordinately regulated (Zakut, 1993), resulting in a distribution in cancers that appears to be very similar, if not identical. Therefore, immune responses directed at either antigen should provide coverage for treatment of the cancers expected to express these TAA. The MAGE-2 and MAGE-3 proteins are 84% identical at the primary amino acid level. As a result, some epitopes are identical in the two antigens, while others are unique to one or the other. It should be noted that two subtypes of MAGE-2, designated "a" and b", have been reported (Zakut, 1993). The gene referred to herein as MAGE-2 corresponds to the MAGE-2a subtype (C. Dahlberg personal communication, NB 1056, p. 16; Van der Bruggen, 1991; Zakut, 1993).

The fourth TAA selected for use in the vaccine is p53. In normal cells the p53 gene induces a cell cycle arrest which allows DNA to be checked for irregularities and maintains DNA integrity (Kuerbitz, 1992). Mutations in the gene abolish its suppressor function and allow escape of transformed cells from the restriction of controlled growth. At the same time, these mutations lead to overexpression of both wildtype and mutated p53 (Levine, 1991) making it more likely that epitopes within the protein may be recognized by the immune system. The most common mutations are at positions 175, 248, 273 and 282 and have been observed in colon (Rodrigues, 1990), lung (Fujino, 1995), prostate (Eastham, 1995), bladder (Vet, 1995) and bone cancers (Abudu, 1999; Hung, 1997).

Table 5 below delineates the tumor antigen expression in breast, colon and lung. By targeting four TAA, the likelihood of the mutation of tumor cells (tumor escape) into cells which do not express any of the tumor antigens is decreased. Preferably, the inclusion of two or more epitopes from each TAA serves to increase the likelihood that individuals of different ethnicity will respond to the vaccine and provides broadened population coverage.

This rational approach to vaccine compositions can be focused on a particular HLA allele, or extended to various HLA molecules or supertypes to further extend population coverage.

Table 6 shows the incidence, 5-year survival rates, and the estimated number of deaths per year for these tumors in the U.S. for each type of cancer in Table 5. In terms of estimated new cases, estimated deaths and 5 year survival rates each of these tumor types has a large unmet need. Globally, the incidence of these tumors is significantly greater.

Example 2

A Padre® Molecule as a Helper Epitope for Enhancement of CTL Induction

There is increasing evidence that HTL activity is critical for the induction of long lasting CTL responses (Livingston et al. *J. Immunol.* 162:3088-3095 (1999); Walter et al., *New Engl. J. Med.* 333:1038-1044 (1995); Hu et al., *J. Exp. Med.* 177:1681-1690 (1993)). Therefore, one or more peptides that bind to HLA class II molecules and stimulate HTLs can be used in accordance with the invention. Accordingly, a preferred embodiment of a vaccine includes a molecule from the PADRE® family of universal T helper cell epitopes (HTL) that target most DR molecules in a manner designed to stimulate helper T cells. For instance, a pan-DR-binding epitope peptide having the formula: aKXVAAZTLKAAa, where "X" is either cyclohexylalanine, phenylalanine, or tyrosine; "Z" is either tryptophan, tyrosine, histidine or asparagine; and "a" is either D-alanine or L-alanine (SEQ ID NO:29), has been found to bind to most HLA-DR alleles, and to stimulate the response of T helper lymphocytes from most individuals, regardless of their HLA type.

A particularly preferred PADRE® molecule is a synthetic peptide, aKXVAAWTLKAAa (a=D-alanine, X=cyclohexylalanine), containing non-natural amino acid residues, specifically engineered to maximize both HLA-DR binding capacity and induction of T cell immune responses.

Alternative preferred PADRE® molecules are the peptide's, aKFVAAWTLKAAa, aKYVAAWTLKAAa, aKFVAAYTLKAAa, aKXVAAYTLKAAa, aKYVAAYTLKAAa, aKFVAAHTLKAAa, aKXVAAHTLKAAa, aKYVAAHTLKAAa, aKFVAANTLKAAa, aKXVAANTLKAAa, aKYVAANTLKAAa, AKXVAAWTLKAAA (SEQ ID NO:30), AKFVAAWTLKAAA (SEQ ID NO:31), AKYVAAWTLKAAA (SEQ ID NO:32), AKFVAAYTLKAAA (SEQ ID NO:33), AKYVAAYTLKAAA (SEQ ID NO:34), AKYVAAYTLKAAA (SEQ ID NO:35), AKFVAAHTLKAAA (SEQ ID NO:36), AKXVAAHTLKAAA (SEQ ID NO:37), AKYVAAHTLKAAA (SEQ ID NO:38), AKFVAANTLKAAA (SEQ ID NO:39), AKXVAANTLKAAA (SEQ ID NO:40), AKYVAANTLKAAA (SEQ ID NO:41) (a=D-alanine, X=cyclohexylalanine).

In a presently preferred embodiment, the PADRE® peptide is amidated. For example, a particularly preferred amidated embodiment of a PADRE® molecule is conventionally written aKXVAAWTLKAAa-NH$_2$.

Competitive inhibition assays with purified HLA-DR molecules demonstrated that the PADRE® molecule aKXVAAWTLKAAa-NH$_2$ binds with high or intermediate affinity (IC$_{50}$≦1,000 nM) to 15 out of 16 of the most prevalent HLA-DR molecules ((Kawashima et al., *Human Immunology* 59:1-14 (1998); Alexander et al., *Immunity* 1:751-761 (1994)). A comparison of the DR binding capacity of PADRE® and tetanus toxoid (TT) peptide 830-843, a "universal" epitope has been published (Panina-Bordignon et al.,

*Eur. J. Immunology* 19:2237-2242 (1989)). The TT 830-843 peptide bound to only seven of 16 DR molecules tested, while PADRE® bound 15 of 16. At least 1 of the 15 DR molecules that bind PADRE® is predicted to be present in >95% of all humans. Therefore, this PADRE® molecule is anticipated to induce an HTL response in virtually all patients, despite the extensive polymorphism of HLA-DR molecules in the human population.

Early data from a phase I/II investigator-sponsored trial, conducted at the University of Leiden (C. J. M. Melief), support the principle that the PADRE® molecule aKX-VAAWTLKAAa, possibly the amidated aKXVAAWTL-KAAa-NH$_2$, is highly immunogenic in humans (Ressing et al., *J. Immunother.* 23(2):255-66 (2000)). In this trial, a PADRE® molecule was co-emulsified with various human papilloma virus (HPV)-derived CTL epitopes and was injected into patients with recurrent or residual cervical carcinoma. However, because of the late stage of carcinoma with the study patients, it was expected that these patients were immunocompromised. The patients' immunocompromised status was demonstrated by their low frequency of influenza virus-specific CTL, reduced levels of CD3 expression, and low incidence of proliferative recall responses after in vitro stimulation with conventional antigens. Thus, no efficacy was anticipated in the University of Leiden trial, rather the goal of that trial was essentially to evaluate safety. Safety was, in fact, demonstrated.

Thus, the PADRE® peptide component(s) of the vaccine bind with broad specificity to multiple allelic forms of HLA-DR molecules. Moreover, PADRE® peptide component(s) bind with high affinity (IC$_{50}$≦1000 nM), i.e., at a level of affinity correlated with being immunogenic for HLA Class II restricted T cells. The in vivo administration of PADRE® peptide(s) stimulates the proliferation of HTL in normal humans as well as patient populations.

One or more PADRE® peptide(s) may be included in a composition, e.g., a vaccine, comprising one or more peptides, either as an individual peptide(s), fused to one or more CTL peptides (epitope and/or analog), or both.

Example 3

Functional Competence of ProGP-Derived DC

One embodiment of a vaccine in accordance with the invention comprises epitope-bearing peptides of the invention delivered via dendritic cells (DC). Accordingly, DC were evaluated in both in vitro and in vivo immune function assays. These assays include the stimulation of CTL hybridomas and CTL cell lines, and the in vivo activation of CTL.

DC Purification

ProGP-mobilized DC were purified from peripheral blood (PB) and spleens of ProGP-treated C57B1/6 mice to evaluate their ability to present antigen and to elicit cellular immune responses. Briefly, DC were purified from total WBC and spleen using a positive selection strategy employing magnetic beads coated with a CD11c specific antibody (Miltenyi Bibtec, Auburn Calif.). For comparison, ex vivo expanded DC were generated by culturing bone marrow cells from untreated C57B1/6 mice with the standard cocktail of GM-CSF and IL-4 (R&D Systems, Minneapolis, Minn.) for a period of 7-8 days (Mayordomo et al., *Nature Med.* 1:1297-1302 (1995)). Recent studies have revealed that this ex vivo expanded DC population contains effective antigen presenting cells, with the capacity to stimulate anti-tumor immune responses (Celluzzi et al., *J. Exp. Med.* 83:283-287 (1996)).

The purities of ProGP-derived DC (100 µg/day, 10 days, SC) and GM-CSF/IL-4 ex vivo expanded DC were determined by flow cytometry. DC populations were defined as cells expressing both CD11c and MHC Class II molecules. Following purification of DC from magnetic CD11c microbeads, the percentage of double positive PB-derived DC, isolated from ProGP-treated mice, was enriched from approximately 4% to a range from 48-57% (average yield=4.5×10$^6$ DC/animal) The percentage of purified splenic DC isolated from ProGP treated mice was enriched from a range of 12-17% to a range of 67-77%. The purity of GM-CSF/IL-4 ex vivo expanded DC ranged from 31-41% (Wong et al., *J. Immunother.*, 21:32040 (1998)).

In Vitro Stimulation of CTL Hybridomas and CTL Cell Lines: Presentation of Specific CTL Epitopes The ability of ProGP generated DC to stimulate a CTL cell line was demonstrated in vitro using a viral-derived epitope and a corresponding epitope responsive CTL cell line. Transgenic mice expressing human HLA-A2.1 were treated with ProGP. Splenic DC isolated from these mice were pulsed with a peptide epitope derived from hepatitis B virus (HBV Pol 455) and then incubated with a CTL cell line that responds to the HBV Pol 455 epitope/HLA-A2.1 complex by producing IFNγ. The capacity of ProGP-derived splenic DC to present the HBV Pol 455 epitope was greater than that of two positive control populations: GM-CSF and IL-4 expanded DC cultures, or purified splenic B cells (FIG. 3B). The left shift in the response curve for ProGP-derived spleen cells versus the other antigen presenting cells reveal that these ProGP-derived cells require less epitope to stimulate maximal IFNγ release by the responder cell line.

Example 4

Peptide-Pulsed ProGP-Derived Dc Promote In Vivo CTL Responses

The ability of ex vivo peptide-pulsed DC to stimulate CTL responses in vivo was also evaluated using the HLA-A2.1 transgenic mouse model. DC derived from ProGP-treated animals or control DC derived from bone marrow cells after expansion with GM-CSF and IL-4 were pulsed ex vivo with the HBV Pol 455 CTL epitope, washed and injected (IV) into such mice. At seven days post immunization, spleens were removed and splenocytes containing DC and CTL were restimulated twice in vitro in the presence of the HBV Pol 455 peptide. The CTL activity of three independent cultures of restimulated spleen cell cultures was assessed by measuring the ability of the CTL to lyse $^{51}$Cr-labeled target cells pulsed with or without peptide. Vigorous CTL responses were generated in animals immunized with the epitope-pulsed ProGP derived DC as well as epitope-pulsed GM-CSF/IL-4 DC (FIG. 4). In contrast, animals that were immunized with mock-pulsed ProGP-generated DC (no peptide) exhibited no evidence of CTL induction. These data confirm that DC derived from ProGP treated mice can be pulsed ex vivo with epitope and used to induce specific CTL responses in vivo. Thus, these data support the principle that ProGP-derived DC promote CTL responses in a model that manifests human MHC Class I molecules.

In vivo pharmacology studies in mice have demonstrated no apparent toxicity of reinfusion of pulsed autologous DC into animals.

Example 5

Dendritic Cell Isolation, Pulsing, Testing and Administration

A presently preferred procedure for vaccination is set forth herein. In brief, patients are treated with ProGP to expand and mobilize DC into the circulation. On the day of peak DC mobilization, determined in accordance with procedures known in the art, patients undergo leukapheresis (approximately 15 L process, possibly repeated once if required to collect sufficient mononuclear cells). The mononuclear cell product is admixed with peptides of the invention by injection through micropore filters (this admixing protocol is not needed if sterile peptides are used). After incubation and washing to remove residual unbound peptides, the cell product vaccine embodiment is resuspended in cryopreservative solution (final 10% DMSO) and, for those protocols involving multiple vaccination boosts, divided into aliquots. The pulsed mononuclear cell product(s) are frozen and stored according to accepted procedures for hematopoietic stem cells.

Vaccination is performed by injection or intravenous infusion of thawed cell product after the hematologic effects of ProGP in the patient have dissipated (i.e., the hemogram has returned to baseline). FIG. 5 provides a flow chart of ex vivo pulsing of DC with peptides, washing of DC, DC testing, and cryopreservation. A more detailed description of the process is provided in the following Examples.

Example 6

Administration of ProGP and Collection of Mononuclear Cells by Leukapheresis Patients are treated with ProGP daily by subcutaneous injection (dose and schedule determined in accordance with standard medical procedures). On the evening before leukapheresis, patients are assessed by an apheresis physician or nurse/technologist for adequacy of intravenous access for large-bore apheresis catheters. If peripheral venous access is deemed inadequate to maintain rapid blood flow for apheresis, then central venous catheters (inguinal, subclavian or internal jugular sites) can be inserted by appropriate medical/surgical personnel. On the day of predicted peak DC mobilization, leukapheresis (approximately 3 blood volumes or 15 L) is performed, for example, on a Cobe Spectra or Fenwal CS3000 (flow rate$\geqq$35 mL/min) to obtain mononuclear cells. The number of DC in the leukapheresis product is estimated by flow cytometric counting of mononuclear cells possessing the immunophenotypes lin-/HLA-DR+/CD11c+ and lin-/HLA-DR+/CD123+ in a 1 mL sample aseptically withdrawn from the apheresis product. The numbers of granulocytes and lymphocytes in the leukapheresis product are counted by automated cytometry (CBC/differential). CBC/differential is performed immediately after the leukapheresis procedure and every other day for ten days to monitor resolution of the hematologic effects of the hematopoietin treatment and apheresis.

Example 7

A Procedure for Dendritic Cell Pulsing

Plasma is removed from the leukapheresis product by centrifugation and expression of supernatant. The cells from the centrifugation pellet are resuspended in OptiMEM medium with 1% Human Serum Albumin (HSA) at a cell density of $10^7$ DC/ml in up to 100 ml.

The peptide(s) of the invention, preferably as individual sterile A2 peptide formulations, are administered directly into the DC culture bag through an injection port, using aseptic technique. After mixing, e.g., by repeated squeezing and inversion, the cell suspension is incubated for four hours at ambient temperature. Cryopreservative solution is prepared by dissolving 50 mL pharmaceutical grade dimethylsulfoxide (DMSO) in 200 mL Plasmalyte®. After the pulsing period, the cell suspension is washed by centrifugation and resuspension in an equal volume of phosphate buffered saline solution. The washing procedure is repeated a defined number of times, e.g., until studies validate that peptides have been removed. Samples of one milliliter each are removed for viability testing and microbiological testing. The cells are then prepared for freezing by centrifugation and resuspension in an equal volume of cryopreservative solution (final 10% DMSO). The cell suspension in cryopreservative is then divided into six equal aliquots, transferred to 50 ml freezing bags (Fenwal) and frozen at controlled rate of PC/min for storage in liquid nitrogen until needed for vaccination procedure.

Assay to Evaluate the Pulsing Procedure

Antigen presenting cells, long-term stimulated T cells corresponding to peptides of the invention, or T cell hybridomas, are used to determine the optimal procedure for incubating the peptide reagents of a vaccine with human cells. Pulsing studies are done using one or more of the following cell sources: purified DC from ProGP treated HLA-A2.1 transgenic mice; human tumor cell lines that express HLA-A2; peripheral blood mononuclear cells from normal human volunteers; peripheral blood mononuclear cells from ProGP treated patients; and/or DC obtained from normal human HLA-A2 Volunteers following the ex vivo culture of their peripheral blood mononuclear cells with GM-CSF and IL-4.

Evaluated conditions include, e.g.:
Cellular isolation procedure and cell number
Concentration of vaccine peptides
Washing conditions to remove ancillary reagents
Post-pulsing manipulations (resuspension, freezing)

Accordingly, these studies demonstrate the ability of the procedure to produce functional HLA-A2/peptide complexes on the surface of the human cells. The validation of the pulsing procedure is established using HLA-A2.1-specific T cell lines after which the Phase I clinical trial occurs.

Example 8

Validation of Peptide Removal from the DC Product

Following pulsing with the peptide reagents, DC from the patient are washed several times to remove excess peptides prior to infusing the cells back into the patient. In this embodiment of a vaccine of the invention, the washing procedure removes unbound peptides. Accordingly, there is no, or negligible, systemic, exposure of the patient to the peptides. Alternative vaccines of the invention involve direct administration of peptides of the invention to a patient, administration of a multiepitopic polypeptide comprising one or more peptides of the invention, administration of the peptides in a form of nucleic acids which encode them, e.g., by use of minigene constructs, or by viral vectors.

Assay for Vaccine Peptides in the Dendritic Cell Wash Buffer

After the DC are incubated with the peptides, the cells are washed with multiple volumes of wash buffer. An aliquot of the last wash is placed onto a nonpolar solid-phase extraction cartridge and washed to reduce the salt content of the sample. Any peptides contained in the buffer will be eluted from the extraction cartridge and evaporated to dryness. The sample is then reconstituted in High Performance Liquid Chromatography (HPLC) mobile phase, injected onto a polymer based reverse-phase HPLC column, and eluted using reverse-phase gradient elution chromatography. Residual peptides are detected using a mass spectrometer set-up to monitor the protonated molecular ions of each peptide as they elute from the HPLC column. The peptides are quantified by comparing the area response ratio of analyte and internal standard to that obtained for standards in a calibration curve.

Example 9

Validation of Trifluoroacetic Acid Removal from the DC Product

In a particular embodiment, peptide reagents may be formulated using 0.1% trifluoroacetic acid (TFA). The washing procedure developed to remove residual peptide also removes residual TFA.

Example 10

Dendritic Cell Release Testing

Identity

The number of DC in the leukapheresis product is estimated by flow cytometric counting of mononuclear cells possessing the immunophenotypes $lin^-/HLA-DR^+/CD11c^+$ and $lin^-/HLA-DR^+/CD123^+$ in a 1 ml sample aseptically withdrawn from the apheresis product. $Lin^-$ cells excludes monocytes, T-lymphocytes, B-lymphocytes, and granulocytes, by using a cocktail of antibodies to lineage markers CD3, CD14, DC16, CD19, CD20, CD56.

Cell Viability

Viability of mononuclear cells is assessed after pulsing and washing, prior to suspension in cryopreservative, by trypan blue dye exclusion. In general, if the cell product contains more than 50% trypan blue-positive cells, the product is not administered to a patient.

Microbiological Testing

The cell suspension in cryopreservative is examined for microbial contamination by gram stain and routine clinical bacterial and fungal culture/sensitivity. If tests are positive for bacterial or fungal contamination, implicit evidence of significant contamination, the product is not infused. If, e.g., a gram stain is negative, the product may be infused for the first vaccination while awaiting results of culture/sensitivity. Antibiotic therapy based on culture results is instituted at the discretion of the treating physician if the patient shows appropriate signs of infection that could be clinically attributable to the infused contaminant.

Example 11

Patient Vaccination

In a preferred embodiment, an aliquot of frozen pulsed dendritic cell product is removed from a liquid nitrogen freezer and kept frozen in an insulated vessel containing liquid nitrogen during transport to the infusion site. The product is thawed by immersion with gentle agitation in a water bath at 37° C. Immediately on thawing, the cell suspension is infused through intravenous line by gravity or by syringe pump. Alternatively, the vaccine is administered by injection, e.g., subcutaneously, intradermally, or intramuscularly. The patient's vital signs are monitored before infusion/injection and at 5 minute intervals during an infusion, then at 15 minute intervals for 1 hour after infusion/injection.

Infusion protocols in accordance with knowledge in the art are carried out for alternative vaccine embodiments of the invention, such as direct peptide infusion or nucleic acid administration.

Example 12

Identification of A2 Supermotif/Motif-Bearing Peptides

Nine CTL epitopes derived from well-characterized tumor antigens (MAGE-2/3, HER-2/neu, p53, and CEA) were selected for the current vaccine using a 3-step process: 1) computer motif analysis of the primary protein sequence to identify motif-containing peptides that will thus have a high likelihood of binding HLA-A2 supertype molecules; 2) direct measurement of MHC binding affinity of the motif-containing peptides to A2 supertype alleles; and 3) immunogenicity testing of high-affinity MHC binding peptides for CTL induction. In addition to identifying native-sequence epitopes, modified epitope analogs were designed to provide enhanced immunogenicity. Analogs were generated by substituting key amino acid residues that enhance either MHC binding affinity or T Cell Receptor (TCR) interaction.

The final vaccine product, EP-2101, is a pool of the nine tumor-associated CTL epitopes (natural and analog sequences) and a PADRE® universal epitope, administered to cancer patients as an emulsion in Montanide® ISA 51 adjuvant. The vaccine is similar to synthetic peptide vaccines (containing one or more peptides) that have been tested by other investigators in cancer patients where CTL induction, positive clinical responses, and vaccine safety have been described (Cormier, J. N., et al., *Cancer J. Sci. Am.* 3:37-44 (1997); Salgaller, M. L., et al., *Cancer Res.* 56:4749-4757 (1996); Wang, F., et al., *Clin. Cancer Res.* 5:2756-2765 (1999); Muderspach, L., et al., *Clin. Cancer Res.* 6:3406-3416 (2000); Ressing, M. E., et al., *J Immunother.* 23:255-266 (2000)). All of the EP-2101 epitopes are immunogenic, using peripheral blood mononuclear cells (PBMC) from HLA-A2.1 positive subjects and an in vitro primary induction assay, in inducing CTLs that respond to the peptide and to tumor cell lines that express the TAA and present the wild-type epitope (Keogh, E., et al., *J. Immunol.* 167:787-796 (2001); Kawashima, I., et al., *Hum. Immunol.* 59:1-14 (1998)). The epitopes were also shown to be immunogenic when tested in an HLA-A2.1/$K^b$ transgenic mouse model used to determine the immunogenicity of HLA-A2.1-restricted human epitopes (Wentworth, P. A., et al., *Eur. J. Immunol.* 26:97-101 (1996); Vitiello, A., et al., *J Exp. Med.* 173:1007-1015 (1991); Lustgarten, J., et al., *Hum. Immunol.* 52:109-118 (1997)).

Native Epitope Sequences

A computer-based motif and algorithm search was performed on the primary amino acid sequences of CEA, MAGE-2/3, HER-2/neu, and p53 to predict peptides most likely to bind the MHC molecules of the five alleles of the HLA-A2 supertype family (Tables 4D and 6) (Sette, A. and J. Sidney, *Immunogenetics* 50:201-212 (1999)). Motif and algorithm-positive peptides were then synthesized and tested for binding to purified HLA-A2.1, the molecule most frequently expressed in humans as well as other MHC molecules of the HLA-A2 supertype family.

In the final step of the epitope screening process, peptides with high cross-reactive MHC binding to the HLA-A2 supertype family receptors were tested for immunogenicity. The assay is an in vitro primary CTL induction system where $CD8^+$ PBMC from normal subjects are stimulated in vitro, initially with peptide-loaded dendritic cells (DCs) (adherent PBMC expanded in GM-CSF and IL-4), followed by two weekly cycles of restimulation with peptide (Keogh, E., et al., *J. Immunol.* 167:787-796 (2001); Kawashima, I., et al., *Hum. Immunol.* 59:1-14 (1998)). Following expansion of naïve precursor cells, CTL activity is determined in the presence of HLA-A2.1 positive target cells and wild-type peptide, using cytotoxicity ($^{51}$Cr-release assay) or interferon-gamma (IFN-γ) production (ELISA) as the read-out. Immunogenic peptides that induced CTL were further tested for responses against the naturally processed epitope expressed on tumor cell lines. Epitopes that induced tumor-reactive CTL were considered as vaccine candidates.

Fixed Anchor Analogs

To break tolerance and improve CTL induction against weakly immunogenic epitopes, tumor-associated peptides with low MHC binding activity were modified to enhance their binding by substituting suboptimal MHC-interacting anchor residues with optimal, motif-associated residues (Kawashima, I., et al., *Hum. Immunol.* 59:1-14 (1998); Parkhurst, M. R., et al., *J Immunol.* 157:2539-2548 (1996)). This strategy of "fixing" anchor residues has been described for a number of tumor and infectious disease epitopes and these analogs have demonstrated enhanced in vivo immunogenicity compared to the wild-type epitope (Kawashima, I., et al., *Hum. Immunol.* 0.59:1-14 (1998); Vierboom, M. P., et al., *J. Immunother.* 21:399-408 (1998)), a finding that is correlated with increased MEC binding (Parkhurst, M. R, et *J. Immunol.* 157:2539-2548 (1996)). The disease relevance of fixed-anchor analogs has been demonstrated by their capacity to induce not only stronger CTL responses, but also CTL that cross-react against the native wild-type epitope expressed on tumor cells (Kawashima, I., et al., *Hum. Immunol.* 59:1-14 (1998); Vierboom, M. P., et al., *J Immunother.* 21:399-408 (1998); Sarobe, P., et al., *J. Clin. Invest* 102:1239-1248 (1998)). More importantly, significant tumor regression has been observed in melanoma patients immunized with a fixed-anchor epitope in conjunction with IL-2 therapy (Rosenberg, S. A., et al., *Nat. Med.* 4:321-327 (1998)).

Heteroclitic Analogs

A second strategy was also used to generate analogs with improved potency for CTL induction. Amino acid substitutions that affect TCR contact residue(s) were introduced into known CTL epitopes, since these analogs have been shown to induce stronger responses than the wild-type epitope (Zaremba, S., et al., *Cancer Res.* 57:4570-4577 (1997); Zugel, U., R. et al., *J. Immunol.* 161:1705-1709 (1998); Rivoltini, L., P., et al., *Cancer Res.* 59:301-306 (1999); Slansky, J. E., et al., *Immunity.* 13:529-538 (2000)). The T cell response stimulated by heteroclitic analogs compared to the wild-type epitope is manifested both as an increase in the response magnitude as well as an enhancement in TCR avidity (Zugel, U., R. et al., *J Immunol.* 161:1705-1709 (1998); Rivoltini, L., P., et al., *Cancer Res.* 59:301-306 (1999); Slansky, J. E., et al., *Immunity.* 13:529-538 (2000); Tangri, S., et al., *J. Exp. Med.* 194:833-846 (2001)), with the latter thought to be a potential mechanism for heteroclicity (Slansky, J. E., et al., *Immunity.* 13:529-538 (2000)).

Heteroclitic analogs are potentially important in cancer vaccines not only for their ability to induce strong T cell responses, but also for their ability to break T cell tolerance. These properties have been demonstrated in animal as well as human trials (Zugel, U., R. et al., *J. Immunol.* 161:17054709 (1998); Slansky, J. E., et al., *Immunity.* 13:529-538 (2000); Fong, L., et al., *Proc. Natl. Acad. Sci. U.S.A* 98:8809-8814 (2001)). In humans, significant anti-tumor responses were recently reported in a trial examining treatment of colon cancer and NSCLC patients with DCs loaded with a heteroclitic analog of a CEA epitope, referred to as CAP1-6D (designated herein as CEA.605D6, peptide 1350.01), that was initially described by Zaremba et al. (Zaremba, S., et al., *Cancer Res.* 57:4570-4577 (1997)). In this clinical study (Fong, L., et al., *Proc. Natl. Acad. Sci. U.S.A* 98:8809-8814 (2001)), five clinical responders were observed out of 12 patients who received the DC vaccine, and a correlation was observed between clinical response and an increase in the percentage of analog-specific CD8$^+$ T cells following vaccination as detected by tetramer staining. During our preclinical studies, heteroclitic analogs were identified which led to the generation of six new analogs modified from three known tumor epitopes, MAGE-3.112, MAGE-2.157, and CEA.691 (Tangri, S., et al., *J. Exp. Med.* 194:833-846 (2001)). All of these analogs induce strong primary human CTL responses in vitro that cross-react against the native epitope expressed by tumor cells (Tangri, S., et al., *J Exp. Med.* 194:833-846 (2001)).

Using the epitope selection process described above, nine epitopes were selected for the vaccine product. These epitopes, shown in Tables 3 and 7, were chosen on the basis of demonstrating 1) broad tumor antigen coverage with a mix of CTL native sequence epitopes, fixed-anchor analogs and heteroblitic analogs; 2) high cross-reactive binding affinity for HLA-A2 supertype alleles; 3) immunogenicity in the in vitro human primary CTL induction assay, particularly in generating CTL that respond to wild-type, epitope-expressing tumor cells; and, 4) wherever available, published reports in the literature showing primary or post-vaccination CTL responses in normal subjects or cancer patients.

Pursuant to our clinical objective of inducing a broad multi-epitope, multi-antigen response in cancer patients, two epitopes are represented from each of three TAAs (HER-2/neu, p53, and MAGE-2/3) and three epitopes from CEA, a more widely expressed TAA on lung- and colon-associated tumors. The extent of cross-reactive binding against multiple HLA-A2 supertype alleles should enable the vaccine to cover a broad and non-ethnically biased population among individuals expressing HLA-A2 supertype alleles.

Four of the epitopes selected are fixed-anchor analogs that were modified for improved MHC binding. One fixed-anchor analog was derived from the well-characterized HER-2/neu.369 epitope, which has been shown to induce strong recall and post-vaccination CTL responses in cancer patients (Zaks, T. Z. and Rosenberg, S. A., *Cancer Res.* 58:4902-4908 (1998); Knutson, K. L., et al., *J. Clin. Invest* 107:477-484 (2001)). By increasing supertype binding through substitution of both MHC anchor residues, the V2V9 analog of HER-2/neu.369 is expected to demonstrate even broader immunogenicity in HLA-A2 supertype individuals. The remaining fixed-anchor analogs (CEA.24V9, p53.139L2B3, and p53.149M2) were designed from epitopes identified in the selection process and they have not been tested previously in the clinic. The p53.139L2B3 analog contains an additional α-aminoisobutyric acid substitution at. 3 (a non-anchor position) to circumvent potential stability issues with the cysteine residue found in the wild-type epitope. As with the epitopes derived from wild-type sequences, all of the fixed-anchor analogs induce CTL that cross-react with the wild-type epitope presented by tumor cell lines (Table 7) (Keogh, E., et al., *J Immunol.* 167:787-796 (2001)).

Another class of analogs represented in the current vaccine are those with heteroclitic activity resulting from substitution of TCR contact residues (Zaremba, S., et al., *Cancer Res.* 57:4570-4577 (1997); Zugei, U., R. et al., *J. Immunol.* 161: 1705-1709 (1998); Rivoltini, L., P., et al., *Cancer Res.*

59:301-306 (1999); Slansky, J. E., et al., *Immunity*. 13:529-538 (2000)). Of the three heteroclitic analogs included, two analogs (MAGE-3.11215 and CEA.691H5) induce strong CTL activity which exceeds that of the wild-type peptide (Tangri, S., et al., *J. Exp. Med.* 194:833-846 (2001)). The third heteroclitic analog, CEA.605D6 (CAP1-6D) (Zaremba, S., et al., *Cancer Res.* 57:4570-4577 (1997)), is included in the current vaccine to provide additional epitope breadth and anti-tumor CTL induction, particularly in light of recent clinical data reporting significant CTL and clinical responses in colon and lung cancer patients vaccinated with DC loaded with this heteroclitic CEA analog (Fong, L., et al., *Proc. Natl. Acad. Sci. U.S.A* 98:8809-8814 (2001)).

The immunogenicity of the vaccine epitopes has been corroborated, particularly in human systems, by additional reports. For example, the HER-2/neu.369 and p53.149 epitopes (wild-type versions of analogs used in EP-2101), and HER-2/neu.689 have induced specific CTL responses using PBMC obtained from healthy donors through primary in vitro induction (zum Buschenfelde, C. M., et al., *J. Immunol.* 165:4133-4140 (2000); Chikamatsu, K., et al., *Clin. Cancer Res.* 5:1281-1288 (1999)) as well as recall responses using PBMC from cancer patients (Knutson, K. L., et al., *J. Clin. Invest* 107:477-484 (2001); Rongcun, Y., et al., *J. Immunol.* 163:1037-1044 (1999)). In addition, the p53.139L2, p53.149M2, HER-2/neu.369, and MAGE-2.157 epitopes were shown by others to induce peptide and tumor cell-reactive CTL in vivo in HLA-A2.1 transgenic mice (Lustgarten, J., et al., *Hum. Immunol.* 0.52:109-118 (1997); Visseren, M. J., et al., *Int J Cancer* 73:125-130 (1997); Petersen, T. R., et al., *Scand. J. Immunol.* 53:357-364 (2001); Theobald, M., et al., *Proc. Natl. Acad. Sci. U.S.A* 92:11993-11997 (1995)).

The final epitope included in the vaccine is a universal PADRE® epitope (Alexander, J., et al., *Immunity.* 1:751-761 (1994)). The PADRE® epitope was designed to bind in a cross-reactive manner to the majority of the DR supertype alleles (Alexander, J., et al., *Immunity.* 1:751-761 (1994)) such that >90% of the general population is predicted to respond against this epitope. In the current vaccine, the PADRE® epitope is included to enhance CTL induction by the pool of CTL epitopes. A number of published studies have demonstrated the ability of HTL responses to augment and support the maintenance of CTL responses in vivo (Knutson, K. L., et al., *J. Clin. Invest* 107:477-484 (2001); Kalams, S. A. and Walker, B. D., *J Exp. Med.* 188:2199-2204 (1998); Weber, J. S, and Mule, J. J., *J. Clin. Invest* 107:553-554 (2001); Toes, R. E., et al., *J Exp. Med.* 189:753-756 (1999)). Indeed, the PADRE® epitope (Muderspach, L., et al., *Clin. Cancer Res.* 6:3406-3416 (2000); Ressing, M. E., et al., *J. Immunother.* 23:255-266 (2000); Weber, J. S., et al., *J. Immunother.* 22:431-440 (1999)), as well as other HTL-inducing antigens and epitopes (Vitiello, A., et al., *J. Clin. Invest* 95:341-349 (1995); Dhodapkar, M. V., et al., *J. Clin. Invest* 104:173-180 (1999)), have been an integral component of several clinical trial vaccines.

In summary, nine CTL epitopes representing a combination of fixed anchor native sequences and heteroclitic analogs, and one PADRE® universal HTL epitope, have been selected for inclusion of EP-2101. This set of epitopes constitutes a unique combination of vaccine constituents intended to provide broad antigen and population coverage among HLA-A2 individuals. The CTL epitopes selected for the current vaccine are capable of inducing CTL from naïve precursors in PBMC from normal subjects and in cancer patients. This observation strongly suggests the absence of complete tolerance against these tumor-associated epitopes and supports their utility for inducing beneficial CTL responses in cancer patients.

Example 13

Immunogenicity of the Vaccine Epitopes and Vaccine Product

As described above, during the epitope screening process to identify vaccine candidates, individual epitopes from TAA were tested for their capacity to induce CTL in vitro from human PBMC obtained from HLA-A2.1 individuals. All of the epitopes selected for the current vaccine were shown to generate CTL in vitro and the CTL generated were capable of recognizing wild-type epitope expressed on tumor cell lines (Keogh, E., et al., *J Immunol.* 167:787-796 (2001); Kawashima, I., et al., *Hum. Immunol.* 59:1-14 (1998); Zaremba, S., et al., *Cancer Res.* 57:4570-4577 (1997)). These observations support the potential immunogenicity of the vaccine epitopes when administered to humans and provide further evidence for the existence of precursor CTL that can be primed with tumor-associated epitopes in cancer patients. The results are further supported by data generated from other laboratories demonstrating recall or post-vaccination CTL responses against most of the nine vaccine epitopes (including the wild-type versions of analogs in the current vaccine) (Lustgarten, J., et al., *Hum. Immunol.* 52:109-118 (1997); Knutson, K. L., et al., *J. Clin. Invest* 107:477-484 (2001); zum Buschenfelde, C. M., et al., *J. Immunol.* 165:4133-4140 (2000); Chikamatsu, K., et al., *Clin. Cancer Res.* 5:1281-1288 (1999); Rongcun, Y., et al., *J Immunol.* 163:1037-1044 (1999); Visseren, M. J., et al., *Int J Cancer* 73:125-130 (1997); Petersen, T. R., et al., *Scand. J. Immunol.* 53:357-364 (2001); Theobald, M., et al., *Proc. Natl. Acad. Sci. U.S.A* 92:11993-11997 (1995)).

The immunogenicity of EP-2101 was also analyzed using HLA-A2.1/$K^b$ transgenic mice which express the human HLA-A2.1 molecule (see also Examples 15-17). These mice have been used to assess the immunogenicity of HLA-A2.1-restricted epitopes following in vivo immunization (Wentworth, P. A., et al., *Eur. J. Immunol.* 26:97-101 (1996); Vitiello, A., et al., *J. Exp. Med.* 173:1007-1015 (1991)) and while useful for in vivo evaluation, they have several limitations. Our studies, using a variety of CTL epitopes, indicate that HLA transgenic mice will respond to approximately 80% of the HLA-A2.1-restricted epitopes to which humans respond Wentworth, P. A., et al., *Eur. J Immunol.* 26:97-101 (1996); Wentworth, P. A., et al., *Int Immunol.* 8:651-659 (1996)). Also, the magnitude of the response detected for a given epitope can vary widely from experiment-to-experiment, especially for responses that are lower in magnitude. Finally, the relative magnitude of the response detected in HLA transgenic mice will not necessarily indicate the relative magnitude that will be induced in humans.

For the in vivo immunogenicity studies in HLA-A2.1/$K^b$ transgenic mice, EP-2101 (prepared by an emulsification protocol (see Example 17) similar to that proposed for drug manufacture) was injected into mice and CTL responses against all of the epitopes in the vaccine were measured and compared to CTL responses induced by co-immunizing mice with each CTL epitope alone plus the PADRE® epitope, in Montanide® ISA 51 adjuvant. CTL responses were determined by measuring IFN-γ production by CTLs using an in situ ELISA (McKinney, D. M., et al., *J. Immunol. Methods* 237:105-117 (2000)), following in vitro stimulation of splenocytes from immunized animals with peptide. As shown in FIG. 6, based on data gathered thus far from 6-10 independent experiments, the EP-2101 vaccine appears to demonstrate immunogenicity for a majority of CTL epitopes. For half of the CTL epitopes in EP-2101, strong CTL responses were observed that exceeded 50 secretory units (SU) of IFN-γ production (CEA.24V9, CEA.691H5, HER-2/neu.369V2V9, MAGE-2.157, and MAGE-3.11215). The remaining epitopes demonstrated moderate to weak CTL responses (<10-50 SU), and these responses were generally associated with larger experimental variations as indicated by the larger standard deviation bars. As discussed above, these variations reflect the limitations of the transgenic mouse assay. However, despite the inherent variability of the assay, the multi-epitope CTL responses induced by the pool of CTL epitopes in EP-2101 appeared comparable to CTL responses induced in mice by each CTL epitope alone, when co-immunized with the PADRE® epitope in Montanide® ISA 51 adjuvant. Thus, overall, these experiments indicate that EP-2101 is immunogenic in HLA-A2.1/$K^b$ transgenic mice. Additional experiments also indicate that EP-2101 can induce HTL responses against the PADRE® epitope in HLA-A2.1/$K^b$ transgenic mice, which are restricted by the mouse H-2 I-$A^b$ allele (Alexander, J., et al., *Immunity.* 1:751-761 (1994)).

Example 14

Immunopharmacology Study in HLA-A2.1/$K^b$ Mice

EP-2101 is an immunotherapeutic vaccine designed to induce CTL responses against nine peptide epitopes derived from four TAAs which are widely expressed on colon and lung cancer cells (CEA, p53, HER-2/neu, and MAGE-2/3). Because TAAs represent self-proteins which are over-expressed in tumor cells, induction of a therapeutic response by EP-2101 may require the breaking of CTL tolerance against self-epitopes and induction of a limited but effective CTL response, one that specifically eliminates tumor cells without eliciting severe immunopathology against any normal tissue that may express low levels of the same TAAs. Pre-clinical characterization of EP-2101 indicated that the vaccine is indeed immunogenic since a broad CTL response of significant magnitude was induced in HLA-A2.1/$K^b$ transgenic mice against several wild-type and analog TAA epitopes in the vaccine (see Example 13).

The immunogenicity of the EP-2101 vaccine against multiple epitopes and multiple self tumor proteins raised the possibility that immunopathological responses directed against normal tissue expressing low levels of TAAs may be induced in cancer patients after vaccination, although studies in murine models (Mizobata, S., K., et al., *Cancer Immunol. Immunother.* 49:285-295 (2000); Morgan, D. J., et al., *J. Immunol.* 160:643-651 (1998)) and previous clinical trials (Cormier, J. N., et al., *Cancer J. Sci. Am.* 3:37-44 (1997); Salgaller, M. L., et al., *Cancer Res.* 56:4749-4757 (1996); Wang, F., et al., *Clin. Cancer Res.* 5:2756-2765 (1999); Muderspach, L., et al., *Clin. Cancer Res.* 6:3406-3416 (2000); Weber, J. S., et al., *J Immunother.* 22:431-440 (1999); Lee, P., et al., *J. Clin. Oncol.* 19:3836-3847 (2001)) have reported the absence of autoimmune toxicities associated with induction of an anti-TAA CTL response. To address this important concern, a pre-clinical immunopharmacology study was undertaken in HLA-A2.1/$K^b$ transgenic mice to determine whether autoimmune pathological responses occur following in vivo immunization with EP-2101. Although not a validated animal model for toxicological testing, this transgenic mouse system offered the opportunity to assess this important safety issue in a pre-clinical setting since the HLA-A2.1/$K^b$ transgene allowed for induction of murine CTL responses against the human CTL epitopes in the vaccine (Wentworth, P. A., et al., *Eur. J Immunol.* 26:97-101 (1996); Vitiello, A., et al., *J Exp. Med.* 173:1007-1015 (1991)).

In this 18 week study, HLA-A2.1/$K^b$ transgenic mice received a total of six treatments with EP-2101 or a placebo emulsion control at three week intervals. Mice were injected at the tail base with EP-2101 at a 150-fold excess dose on a mg/kg basis compared to the dose planned for cancer patients in the clinical trial. Histopathology was performed on injected animals at three time points; at week two following a single treatment, at week 9 after three treatments, and at week 18 after six treatments, on tissue from seven major organs (heart, lung, kidney, stomach, intestine, brain and liver) from each animal, as well as on skin isolated from the injection site. In addition to histopathology, animals were monitored at regular intervals for adverse events and body weight. Concurrent to histopathology analysis at the 3 time points and adverse event monitoring, the CTL responses in the spleen of vaccinated and placebo-treated mice were also measured to correlate any immunopathology with presence of CTL responses against epitopes in the vaccine.

Results from this immunopharmacology study indicated that treatment with EP-2101 or an emulsion control did not result in autoimmune immunopathology in major organs of HLA-A2.1/$K^b$ transgenic mice at all of the time points examined, even though strong CTL responses were detected in animals. Histology sections of seven major organs from animals treated with EP-2101 or emulsion control appeared normal at all of the time points studied. The only pathology observed in this study attributable to treatment was the appearance of granulomatous inflammation and granuloma formation at the injection site skin, which appeared in both the vaccine and the emulsion control treatment groups. This observation is a common side-effect of treatment with the Montanide® ISA 51 adjuvant used in this study (Wang, F., et al., *Clin. Cancer Res.* 5:2756-2765 (1999); Lee, P., et al., *J. Clin. Oncol.* 19:3836-3847 (2001); Leenaars, M., et al., *Vet Imnzunol Immunopathol.* 61:291-304 (1998); Yamanaka, M., et al., *J. Vet. Med. Sci.* 54:685-692 (1992)).

Adverse event monitoring of treated mice throughout the 18 week study indicated an overall absence of symptomologies associated with illness or toxicity, in both the vaccine and emulsion control-treated groups (e.g. lethargy, diarrhea, cachexia, paralysis, abnormal posture). The only observation of note was the appearance of a palpable lump at the tail base of all animals, consistent with granuloma formation, which appeared transiently over a 2V2 week period between the 4th and 5th treatment periods, in both the vaccine and emulsion control-treated groups. This transitory adverse event was not associated with necrosis or bleeding at the injection site skin, and such injuries were not observed in any animal throughout the duration of the entire study. Finally, the absence of serious adverse events and immunopathology in test animals was confirmed by their body weight measurements which appeared normal and increased steadily over the course of the study.

In summary, the absence of autoimmune inflammatory pathology in the HLA-A2.1/$K^b$) mouse model system observed in this current study is reminiscent of the absence of similar pathologies reported in previous human clinical trials where peptide vaccines formulated in Montanide® ISA 51 adjuvant were administered to cancer patients (Cormier, J. N., et al., *Cancer J Sci. Am.* 3:37-44 (1997); Salgaller, M. L., et al., *Cancer Res.* 56:4749-4757 (1996); Wang, F., et al., *Clin. Cancer Res.* 5:2756-2765 (1999); Muderspach, L., et al., Clin. Cancer Res. 6:3406-3416 (2000); Weber, J. S., et al., *J. Immunother.* 22:431-440 (1999); Lee, P., et al, *J. Clin. Oncol.* 19:3836-3847 (2001)). For the EP-2101 vaccine, the absence of autoimmune immunopathology in HLA-A2.1/$K^b$ transgenic mice in the face of a broadly specific CTL response directed at multiple epitopes of self tumor antigens supports the general safety of administering this vaccine to colon and lung cancer patients in the proposed clinical trials.

Example 15

Clinical Trial

EP-2101 is a therapeutic, peptide vaccine for use as an adjuvant therapy in patients with cancer. The vaccine is designed for administration to patients for the induction of cytotoxic T lymphocytes (CTL) directed against carcinoembryonic antigen (CEA), p53, human epidermal receptor-2/neurological (HER-2/neu) and melanoma antigen 2 and 3 (MAGE-2/3), tumor associated antigens (TAAs) that are frequently over-expressed in colon and non-small cell lung cancer (NSCLC). The clinical objective for inducing CTL responses against these four well-characterized TAAs is to delay or prevent the recurrence of cancer following surgery, chemotherapy or radiation.

Cancer of the lung continues to be a major health problem with a very high mortality rate. Approximately 170,000 new lung cancer cases were predicted in the United States in 2001 and an estimated 160,000 patients expected to die from the disease. About 80% of lung cancers are NSCLC, and a majority of these patients present with later stage disease. The "standard of care" for NSCLC remains surgery, radiation therapy, or chemotherapy. In addition, some patients receive adjunctive therapy after surgery in the form of chemotherapy following the removal of detectable tumor, although clinical studies are only now ongoing to assess the benefit of such treatment. Despite these treatments, the 2 year survival rate is 30% for stage IIIa, 45% for IIb, 60% for IIa and Ib and 80% for Ia. Mountain, C. *Lung Cancer; A Handbook For Staging, Imaging and Lymph Node Classification* (1999). Therefore, effective adjuvant therapies are critically needed.

The continued improvement in detection of colon cancers has enhanced the ability to treat patients early in the course of disease. According to the American Cancer Society, the five-year survival rate for local disease is 91% while the survival rate for disseminated disease is only 7% (American Cancer Society, Cancer Facts and Figures 2001). Projected deaths in the United States from colon cancer are approximately 50,000 in 2001. The "standard of care" for stage D1 colon cancer is surgery followed by chemotherapy utilizing 5-fluorouracil and leucovorin. Recently there has been increased use of irinotecan with 5-fluorouricl and leucovorin in the adjuvant setting. Despite these available regimens, additional safe and effective adjuvant treatments are needed.

EP-2101 is composed of ten synthetic peptides, each composed of 9-13 amino acid residues, formulated as a stable water-in-oil emulsion in Montanide® ISA 51 adjuvant. Nine of the peptides represent Cat epitopes. Each CTL epitope is restricted by HLA-A2.1 and at least one other member of the HLA-A2 superfamily of MHC class I molecules, providing coverage of approximately 45% of the general population. The CTL epitopes included represent a combination of wild-type, fixed-anchor analog and heteroclitic analog epitopes. The tenth synthetic peptide is a pan-DR epitope (PADRE®), a rationally-designed helper T lymphocyte (HTL) epitope included to augment the magnitude and duration of CTL responses.

The concept of inducing a CTL response to delay or prevent the recurrence of cancer is supported by significant animal model data, studies correlating tumor infiltration with a favorable clinical outcome and reports of tumor regression following spontaneous or vaccine-induced anti-tumor T cell responses (Yu, Z. and Restifo, N. P., *J. Clin. Invest* 110:289-294 (2002)). Peptide epitopes have been utilized for the induction of CTL responses in cancer patients in numerous clinical studies with some encouraging results (Rosenberg, S. A., et al., *Nat. Med.* 4:321-327 (1998); Fong, L., et al., *Proc. Natl. Acad. Sci. USA* 98:8809-8814 (2001)). To improve the clinical outcome in the proposed studies, the EP-2101 peptide vaccine was designed to incorporate the insights and promising concepts learned from previous studies. Specifically, EP-2101 incorporates:

1. defined, optimal-length CTL epitopes derived from multiple, well-characterized TAAs;
2. epitopes with high HLA binding affinity and demonstrated ability to induce CTL that recognize tumor cell lines;
3. epitopes that are a mixture of wild-type sequences and two types of analogs, fixed-anchor and heteroclitic, that were shown to induce responses in humans that correlated with clinical responses;
4. a rationally-designed, non-self, helper T cell PADRE® epitope, that has been shown to induce helper responses in humans;
5. Montanide® ISA 51, a mineral oil adjuvant similar to Incomplete Freund's Adjuvant that is a well-characterized adjuvant for human use that has exhibited acceptable safety and potency in numerous clinical studies (Weber, J. S., et al, *J Immunother.* 22:431-440 (1999); Lee, P., et al., *J. Clin. Oncol.* 19:3836-3847 (2001); Cormier, J. N., et al., *Cancer J. Sci. Am.* 3:37-44 (1997); Wang, F., et al., *Clin. Cancer Res.* 5:2756-2765 (1999); Muderspach, L., et al., *Clin Cancer Res.* 6:3406-3416 (2000); Ressing, M. E., et al., *J. Immunother.* 23:255-266 (2000); Yamshchikov, G. V., et al., *Int J Cancer* 92:703-711 (2001); Rosenberg, S. A., et al., *J Immunol.* 163:1690-1695 (1999)).

The unique combination of wild-type and analog epitopes derived from well-studied TAAs and delivered in an adjuvant that has produced encouraging clinical data should provide an opportunity to improve on the results obtained to date using peptide-based cancer vaccines.

Rationale for Dose Selection

EP-2101 is an immunotherapeutic vaccine consisting of nine peptide epitopes derived from four TAAs which stimulate CTL responses and the PADRE® universal helper T cell epitope. The 10 peptides are formulated in an emulsion with Montanide® ISA 51 adjuvant which will be administered to NSCLC and colon cancer patients to assess safety and immunogenicity of the vaccine. Guidance as to the appropriate vaccine dosage for treating patients was provided by reports of previous clinical trials where CTL and clinical responses as well as vaccine safety were reported following administration of a peptide/Montanide® ISA 51 vaccine (Weber, J. S., et al., *J Immunother.* 22:431-440 (1999); Lee, P., et al., *J. Clin. Oncol.* 19:3836-3847 (2001); Cormier, J. N., et al., *Cancer J. Sci. Am.* 3:37-44 (1997); Wang, F., et al., *Clin. Cancer Res.* 5:2756-2765 (1999); Muderspach, L., et al., *Clin. Cancer Res.* 6:3406-3416 (2000); Ressing, M. E., et al., *J. Immunother.* 23:255-266 (2000); Yamshchikov, G. V., et al., *Int J Cancer* 92:703-711 (2001); Rosenberg, S. A., et al., *J Immunol.* 163:1690-1695 (1999)).

Several peptide vaccines formulated in Montanide® ISA 51 have been tested in cancer patients and these vaccines have generally been deemed safe and well-tolerated with no severe dose-related systemic toxicities being reported (Weber, J. S., et al., *J. Immunother.* 22:431-440 (1999); Cormier, J. N., et al., *Cancer J. Sci. Am.* 3:37-44 (1997); Wang, F., et al., *Clin. Cancer Res.* 5:2756-2765 (1999); Muderspach, L., et al., *Clin. Cancer Res.* 6:3406-3416 (2000); Ressing, M. E., et al., *J. Immunother.* 23:255-266 (2000)). The dose of peptide administered to patients in these trials has been as high as 10 mg of total peptide per treatment, with most being in the range of 1-2 mg total peptide, and the treatment schedule was similar to that being proposed for the EP-2101 clinical trial (i.e. 4-6 subcutaneous injections at 3-4 week intervals). The most common toxicities reported were local injection site reactions (pain, tenderness, and granuloma formation) that were almost always scored grade 1 or 2 in severity (Wang, F., et al., *Clin. Cancer Res.* 5:2756-2765 (1999); Muderspach, L., et al., *Clin. Cancer Res.* 6:3406-3416 (2000); Ressing, M. E., et al., *J. Immunother.* 23:255-266 (2000)). Other transient grade 1/2 toxicities that were occasionally observed included nausea, headaches, fever, and fatigue. Studies testing vaccines with more than a single peptide formulated in Montanide® ISA 51 adjuvant include the clinical trials reported by Yamshchikov et al. (Yamshchikov, G. V., et al., *Int J Cancer* 92:703-711 (2001)) and Ressing et al. (Ressing, M. E., et al., *J. Immunother.* 23:255-266 (2000)). In each study, melanoma or cervical carcinoma patients were treated with a mixture of four or five peptides, respectively, injected at doses up to 3 mg total peptide. As observed in other studies, both vaccines showed only limited grade 1/2 toxicities. Thus, collectively, data from these clinical trials indicate that vaccines consisting of one or several peptide epitopes formulated in Montanide® ISA 51 at total peptide doses up to 10 mg are generally well-tolerated.

With respect to induction of CTLs and clinical responses by peptide/Montanide® ISA 51 vaccines, clinical trials examining escalating doses of peptide, ranging from 0.1 to 10 mg of peptide per injection dose, have shown that CTL responses and clinical responses are induced in this dose range, particularly at doses approaching 1 mg per peptide Weber, J. S., et al., *J Immunother.* 22:431-440 (1999); Cormier, J. N., et al., *Cancer J. Sci. Am.* 3:37-44 (1997); Wang, F., et al., *Clin. Cancer Res.* 5:2756-2765 (1999); Muderspach, L., et al., *Clin. Cancer Res.* 6:3406-3416 (2000))[1-4]. For example, in a noteworthy study described by Rosenberg et al. 7; 8 (Rosenberg, S. A., et al., *Nat. Med.* 4:321-327 (1998); Rosenberg, S. A., et *J. Immunol.* 163:1690-1695 (1999)), where significant post-vaccination clinical responses were reported, a 1 mg dose of a single fixed-anchor analog peptide, gp100.209(210M), was delivered in Montanide® ISA 51. In this trial, a 40% clinical response rate was observed in melanoma patients following peptide vaccination in conjunction with IL-2 therapy, compared to a historical response rate of 15% with IL-2 therapy alone (Rosenberg, S. A., et al., *Nat. Med.* 4:321-327 (1998)). Similarly, in another trial where a HPV-16 E7 peptide vaccine was tested in patients with high-grade cervical intraepithelial neoplasia, CTL responses and clinical responses were reported at doses of 0.3 mg and 1 mg (Muderspach, L., et al., *Clin. Cancer Res.* 6:3406-3416 (2000)). With regard to correlating CTL induction with peptide dose, Wang et al. (Wang, F., et al., *Clin. Cancer Res.* 5:2756-2765 (1999)) observed that a high dose of the Melan-A/MART-1.27 peptide in Montanide® ISA 51 adjuvant (2 mg peptide/dose) appeared to result in a greater magnitude of CTL responses, as measured by interferon-gamma (IFN-γ) release using the enzyme-linked immunospot (ELISPOT) assay, when compared to patients receiving a lower dose (0.1 mg/dose). Although the number of patients in this trial was limited, this finding is consistent with other studies in humans immunized with a lipidated HBV CTL peptide construct (Vitiello, A., et al., *J Clin. Invest* 95:341-349 (1995)) or a tumor specific bcl-abl breakpoint peptide delivered in QS-21 adjuvant (Pinilla-Ibarz, J., et al., *Blood* 95:1781-1787 (2000))[10] where higher doses of peptide were shown to be more consistent at inducing T cell responses than lower doses.

A stable emulsion was generated at a 5 mg/ml total peptide dose (0.5 mg/ml per peptide epitope). Thus, cancer patients in the EP-2101 clinical trial will receive a dosage corresponding to 5 mg of total peptide (0.5 mg per epitope) in an injection volume of 1 ml. Patients will receive six total subcutaneous injections at three week intervals in an injection volume of 1 ml.

Potential risks of vaccine administration are known to the clinician of ordinary skill in the art and include discomfort at the site of injection, general symptoms associated with administration of a vaccine (chills, fever, rash, aches and pain, nausea, headache and fatigue); reproductive toxicity, anaphylactic reaction, effects on pregnancy and fetal development, and autoimmune reactions, including those of the retina.

Structural Formula

The amino acid sequence of each peptide is given in Tables 3 and 7.

Formulation of Dosage Form

EP-2101 is a sterile, preservative-free emulsion of 10 peptide epitopes at a concentration of 0.5 mg/ml each, formulated in Montanide® ISA 51 adjuvant at a ratio of 1:1 (w:w) and filled into rubber-stoppered glass vials. The peptides are synthesized using standard Boc or Fmoc chemistry for solid phase peptide synthesis starting with the appropriate resin, and purified by standard methods. The adjuvant is a mineral oil adjuvant, similar to Incomplete Freund's Adjuvant, manufactured and supplied by Seppic, Inc., Fairfield, N.J. EP-2101 is manufactured under aseptic conditions. Peptides are dissolved in three different solvents, sterile filtered, pooled and then emulsified in adjuvant via homogenization under controlled conditions.

Route of Administration

EP-2101 is designed for subcutaneous injection. The vaccine will be administered as a 1 ml injection every three weeks for a total of six injections. The total peptide dose for each injection will be 5.0 mg (0.5 mg of each peptide).

Manufacture of Drug Substance

Peptides are prepared using solid phase synthesis methodology. Briefly, fluorenylmethoxycarbonyl (Fmoc) and/or tert-butyloxycarbonyl (Boc) groups are used as the protecting groups for the amino acid residues in the synthesis. The peptide is built upon the appropriate resin.

Amino acid derivatives are added to the resin-based amino acid using three equivalents each of DIC and HOBt as the coupling reagents. The Fmoc or Boc protecting group is removed from the terminal amino acid of the resin-based peptide using 20% piperidine in DMF or 65% TFA in dichloromethane, respectively.

The remaining Fmoc-N- or Boc-N-protected amino acid residues are added to the resin-based peptide in sequential coupling cycles using DIC and HOBt as the coupling reagents and 20% piperidine in DMF or 65% TFA in dichloromethane to remove Fmoc and Boc protecting groups, respectively.

Some side-chain protecting groups are removed using appropriate organic mixtures prior to peptide cleavage from the resin. Both removal of additional protecting groups and cleavage from the resin are achieved by treatment of the peptide-resin with a mixture of hydrogen fluoride/methoxybenzene or TFA/water. The peptide is extracted from the resin with acetic acid and, in some cases, extraction with trifluoroacetic acid. The resin is washed with ether. The peptide is isolated by lyophilization from the HOAc/TFA solution.

The peptide is purified by preparative Reverse Phase High Performance Liquid Chromatography (RP-HPLC) on a C18 derivatized silica stationary phase. The column is eluted and the fractions containing pure peptide are pooled and the peptide is isolated by Lyophilization. In some cases RP-HPLC is followed by ion exchange purification/desalting using HOAc-buffered solvents. The resulting fractions are isolated by lyophilization.

Solubility of Individual Peptides

Solubility studies have been performed on the peptides, with solubility defined as a clear solution with no visible particulates (Table 8). Only 6 out of 10 peptides (1013.08, 1243.08, 1295.03, 1323.06, 1350.01 and 1352.03) were soluble at physiological pH. Therefore, the peptides were tested at 2-5 mg/ml in various aqueous acidic solutions and aqueous basic solutions, in addition to dimethylsulfoxide (DMSO).

Specifications and Analytical Methods for the Drug Substance

Table 9 describes the specifications for the Drug Substance.

Components and Quantitative Composition

The components and quantitative composition of EP-2101 are described in Table 10.

Component Specifications

The components used in the manufacture of the drug product are listed in Table 11.

Method of Manufacture of the Bulk Drug Product and Drug Product

The bulk drug product is prepared as shown in FIG. 5. The bulk drug product is formulated into three solutions (see Tables 8 and 12) based on the solubility of individual peptides in each of the three solvents and the solubility of the peptides when pooled. Briefly, to allow for aseptic processing, the 10 peptides are dissolved into either an acidic solution (0.1875 M acetic acid), a basic solution (0.1 M sodium hydroxide) or the organic solvent DMSO. These three peptide-containing pools are sterilized by filtration. Under aseptic conditions, these three peptide pools are combined, buffered, pH adjusted and then homogenized with Montanide® ISA 51 adjuvant under temperature-controlled conditions to form the drug product. The drug product, a stable 1:1 (w:w) emulsion, is then filled into 2 ml glass vials and stored at 2-8° C.

Drug Product Specifications and Analytical Methods

Tables 13 and 14 describe the specifications for EP-2101 bulk drug product and drug product, respectively.

Peptide Concentration (Each Peptide)

Concentration of all peptide components in the EP-2101 Drug Product is assayed by RP-HPLC (conditions illustrated in Table 15). A specified quantity of the emulsion is mixed with a solution of 0.1% TFA in DMSO to form a two-layered mixture. Attempts to produce a clear, homogeneous solution for HPLC analysis by using solvents other than DMSO were unsuccessful. Sampling of the aforementioned two-phase mixture takes place by inserting a syringe or pipette through the top mineral oil layer and into the bottom, DMSO layer. The only sample taken for HPLC analysis is taken from the DMSO layer, in which all peptides are soluble. HPLC chromatography affords a distinct chromatographic peak for each peptide, which upon integration and comparison to a calibration curve yields the individual peptide concentration in the EP-2101 Drug Product. The biphasic nature of the sample introduces variability in the estimation of the full sample volume as well as the transfer of the sample. Subsequently, because of the complexity of sample preparation and handling, unusually large errors in determining the peptide concentration (as high as 30%) were observed. The large variability was not accompanied by major degradation product formation or other unusual physical changes of the sample, and is inferred to be a result of sample preparation and handling. For this reason the specification of ±50% of the intended concentration was set as a release and stability criterion. Attempts to improve the sample handling and, simplify the biphasic mineral oil-DMSO mixture are currently underway with a primary aim of narrowing the release and stability specifications.

Potency

EP-2101 is composed of synthetic CTL and HTL peptide epitopes. Peptide content and integrity can be determined accurately by physical/chemical characterization using the analytical methods described above (e.g. HPLC, viscosity, and particle size analysis). In addition, a method for evaluating the overall potency of the drug product has been developed.

Development of a relevant potency assay is challenging because the EP-2101 vaccine is designed to specifically stimulate HLA-A2.1-restricted CTL responses in humans and not other species. One way to address this challenge is to measure the in vivo potency of EP-2101 using mice that express the HLA-A2.1 molecule as a transgene (i.e. HLA-A2.1/$K^b$ transgenic mice). The proposed EP-2101 potency assay is similar to the preclinical assay used to measure the immunogenicity of EP-2101 CTL epitopes in HLA-A2.1/$K^b$ transgenic mice (see Example 13). It should be pointed out that the HLA-A2.1/$K^b$ transgenic mouse assay has limitations in quantifying CTL responses, specifically: 1) only about 80% of the HLA-A2.1-restricted epitopes that are immunogenic in humans also induce CTL responses in transgenic mice (Wentworth, P. A., et al., *Eur. J. Immunol.* 26:97-101 (1996)), therefore, CTL responses against some epitopes cannot be quantified using this system, and; 2) using a number of approaches, we have found that in vivo CTL responses generated in HLA transgenic mice, whether induced by vaccination or natural infection, are variable from experiment-to-experiment due to individual animal differences and to the in vitro manipulation of primed T cells required for this assay method (e.g. see FIG. 7). Although the potency assay has limitations common to in vivo bioassays, it provides a measurement of overall potency of EP-2101. Accordingly, it serves as an appropriate complement to the highly sensitive and quantitative analytical assays described above.

In the EP-2101 potency assay, HLA-A2.1/$K^b$ transgenic mice are injected with EP-2101 and 14 days later splenocytes from immunized animals are stimulated in vitro with representative EP-2101 CTL epitopes, CEA.691H5 (1352.02) and HER-2/neu.369V2V9 (1334.10), to expand in vivo-primed CTL. Following in vitro expansion, in vivo-primed CTL responses (also referred to as effector cells) will be quantitated by measuring, with an ELISA, their capacity to produce IFN-γ when stimulated again in vitro with the CEA.691H5 or HER-2/neu.369V2V9 peptides. CTL activity measured by ELISA is expressed as secretory units (SU), which represent the number of effector cells needed to secrete 100 pg of IFN-γ in response to peptide (McKinney, D. M., et al., *J. Immunol. Methods* 237:105-117 (2000)). Thus, the SU value is a reflection of the level of CTL induced by EP-2101 in HLA-A2.1/$K^b$ transgenic mice and is a measurement of vaccine potency.

Example 16

Detailed Description of the Potency Assay

To assess the drug potency, an assay has been developed to measure the ability of the vaccine to induce a CTL response in transgenic mice that express a chimeric MHC class I molecule in which the heavy chain is composed of the first and second domains of the HLA-A2.1 molecule and the third domain, transmembrane domain, and cytoplasmic domain of the mouse H-2$K^b$ molecule. Previously, it was demonstrated that when HLA-A2.1/$K^b$ transgenic mice are immunized with HLA-A2.1-restricted epitopes known to be immunogenic in humans, approximately 80% of the epitopes induce CTL responses (Wentworth, P. A., et al., Eur. J. Immunol. 26:97-101 (1996)). These data confirm the validity of using these mice to quantitate CTL responses induced upon immunization with a vaccine composed of HLA-A2.1 restricted epitopes.

The selection of two CTL epitopes for measuring EP-2101 potency and the establishment of a potency assay specification is described below. Specific protocols are described in Example 17.

Briefly, analysis of the immunogenicity of EP-2101 in several experiments indicated that the different epitopes in the vaccine induced varying responses ranging from a mean of ~10 SU to >100 SU and these responses were associated with high intra- and inter-experimental variability, particularly for weakly immunogenic epitopes. Both of these factors made it unfeasible to measure potency of the vaccine based on CTL responses against all nine epitopes in the vaccine. Instead, an assay was developed using the immunogenicity measurements of two representative, immunogenic epitopes in EP-2101 as an indicator of overall vaccine potency.

Selection of the two epitopes was based on a retrospective analysis of CTL immunogenicity data generated from experiments where mice were injected with EP-2101 at varying emulsion doses. CTL responses from 6-10 independent experiments in which mice were immunized with a 10 mg/ml emulsion dose were evaluated and the two top immunogenic epitopes in EP-2101 were CEA.691H5 (geometric mean response, 164×/÷1.8 SU) and HER-2/neu.369V2V9 (geometric mean response, 152×/÷2.4 SU), with a third epitope, MAGE-3.11215 (geometric mean response, 92×/÷2.1 SU) serving as a potential back-up epitope. In addition to the high response magnitude, the overall variability associated with these responses was within ranges normally observed for immunogenic epitopes tested in HLA-A2.1/$K^b$ transgenic mice (SD between ×/÷ 1.8-2.4). Although this extensive database was generated with EP-2101 at a 10 mg/ml emulsion dose, further experiments indicate that the EP-2101 emulsions at a 2.5 mg/ml and 5 mg/ml total peptide dose induce a comparable level of CTL response as the 10 mg/ml emulsion dose against the highly immunogenic CEA.691H5, HER-2/neu.369V2V9, and MAGE-3.11215 epitopes.

Further support for epitope selection was provided by data from responses-measured in the ELISPOT assay which tests for CTL effector cell activity without in vitro expansion by peptide stimulation. Consistent CTL responses could be detected by the ELISPOT assay against the HER-2/neu.369V2V9 and CEA.691H5 epitopes and these results confirm the strong immunogenicity of the two candidate potency assay epitopes compared to others in the vaccine when tested with this assay.

In addition to responses measured in immunized mice, the baseline CTL responses observed in naïve mice or in mice injected with a placebo Montanide® ISA 51 emulsion were also considered. For the three top epitope candidates, CTL responses in negative control mice in three independent experiments were low (<10 SU), such that the difference in the magnitude between the baseline and vaccine-induced CTL responses was sufficiently large to assure detection of a drop in vaccine potency should it occur after manufacture.

A final consideration in epitope selection for the potency assay was variability of CTL induction associated with individual mice. Since the protocol for the EP-2101 potency assay specifies measurement of CTL responses in a pooled splenocyte population derived from 6 immunized mice, a potential source of variability in the assay could be the frequency of CTL induction in individual animals. This consideration is not trivial since sporadic CTL responses behaving in an all-or-none fashion have been observed in individual mice injected with different types of highly immunogenic vaccine constructs (e.g. lipopeptide, DNA) (unpublished results). In light of this important parameter, a study was initiated to determine the variability of CTL induction against the top three potency epitope candidates in 15 individual HLA-A2.1/$K^b$ transgenic mice immunized with the EP-2101 vaccine. CTL responses against all three epitopes could be demonstrated in 100% of the immunized animals. As expected, the hierarchy of CTL responses against each of the three epitopes was similar to that measured with a pool of splenocytes from primed mice and the degree of variability of the responses between individual animals was within an acceptable range for an in vivo assay. Thus, CEA.691H5 and HER-2/neu.369V2V9 induced the most robust and reproducible CTL response in all animals, followed by the MAGE-3.11215 epitope (geometric mean SU response in 15 mice against the CEA, HER-2/neu, and MAGE-3 epitopes was 252×/÷1.4, 169×/÷1.7, and 48×/÷1.7, respectively and these responses were within the range observed with pooled splenocytes from EP-2101-immunized animals).

In summary, the CEA.691H5 and HER-2/neu.369V2V9 epitopes were selected as the potency assay epitopes, and the MAGE-3.11215 epitope was designated as a back-up based on 1) the strength of CTL responses measured in EP-2101 immunized animals using the in situ ELISA and ex vivo ELISPOT assays, 2) the equivalent magnitude of CTL responses generated against the epitopes with EP-2101 vaccine formulated at varying peptide emulsion doses, 3) the inter- and intra-experiment variability of these CTL responses, 4) the baseline responses in negative control animals, and 5) the consistency of CTL induction in individual animals.

A potency assay specification was established to determine the upper and lower limits of CTL responses against the two potency epitopes induced by EP-2101. To establish the lower specification limit, the data-base generated in naïve or emulsion control (placebo) mice over six experiments (18 data-points) was analyzed and the SU values of all cultures from negative control mice were compiled. The lower limit specification was established by first calculating the geometric mean SU response and SD from all of the negative control cultures and then calculating a 3 SD cutoff value. This value for the CEA.691H5 epitope was calculated to be 22 SU (geometric mean×3 SD=1.53×14.01; with rounding to the next highest integer) and 8 SU for the HER-2/neu.369V2V9 epitope (geometric mean×3 SD=0.49×14.58). For a given test sample of EP-2101 to pass potency, the geometric mean SU value of CTL activity from EP-2101-primed splenocytes for both epitopes must equal or exceed its respective lower limit specification.

To establish the upper limit of the assay, SU values from 11 experiments (32 data-points) generated from EP-2101-injected mice were compiled and the geometric mean SU value from the three highest experiments for each epitope was calculated. For the CEA.691H5 epitope, this calculation resulted in a value of 289.5 SU based on the responses of individual cultures from three experiments. For HER-2/neu.369V2V9, the geometric mean SU of the three highest responding experiments was 330.9 SU. Since in vivo biological responses in vaccine-immunized subjects tend to generate significant differences at log intervals of dosage (Vitiello, A., et al., *J. Clin. Invest.* 95:341-349 (1995); Pinilla-Ibarz, J., et al., *Blood* 95:1781-1787 (2000)), a log greater CTL response value from the mean of the highest responses observed in EP-2101-immunized animals was established as the upper limit specification. Thus, the upper limit specification for the two epitopes was determined by multiplying the geometric mean SU value of the three highest experiments by 10 then rounding this value. For CEA.691H5 this value was calculated to be 2,895 SU or 2,900 SU and for the HER-2/neu epitope the same calculation yielded a value of 3,309 SU or 3,300 SU. A given test sample of EP-2101 which exceeds the upper limit specification of 2,900 SU and 3,300 SU for the CEA.691H5 and HER-2/neu.369V2V9 epitopes respectively, fails the potency assay due to concerns regarding super-optimal CTL inducing activity and potential toxicity.

Each potency experiment will also include system suitability controls which will determine the validity of the EP-2101 potency measurements, obtained in the experiment. As a positive control, mice will be co-immunized with each CTL epitope alone and the PADRE® epitope in a Montanide® ISA 51 emulsion and CM responses in this group will be monitored using the same specifications established for the EP-2101 vaccine product. As a negative control, splenocytes from naïve (non-vaccinated) mice will be stimulated in vitro with each CTL epitope under identical conditions as splenocytes harvested from EP-2101-immunized mice and as a criteria for a valid potency assay, CTL responses in this control group should not exceed the lower specification limit for each epitope.

Example 17

Detailed Protocols

Mice

HLA-A2.1/$K^b$ transgenic mice were generated as described previously (Vitiello A., et al., J. Exp. Med. 173: 1007-15 (1991)) as an F1 generation of a cross between an HLA-A2.1/$K^b$ transgenic strain generated on the C57/BL6 background and BALB/c mice.

Cell Culture Medium

All cells were grown in RPMI-1640 medium with HEPES (Life Technologies, Grand Island, N.Y.) supplemented with 10% FBS, 4 mM L-glutamine, $5\times10^{-5}$ M 2-ME, 0.5 mM sodium pyruvate, 1× non-essential amino acid residues, 100 µg/ml streptomycin and 100 U/ml penicillin (hereafter designated RPMI-10 medium).

Preparation of Montanide ISA 51 Peptide Emulsions

For emulsion preparations, the individual peptides in the EP-2101 vaccine were solubilized from a lyophilized powder in the appropriate aqueous or DMSO solution and at the appropriate concentrations to yield 10, 5, or 2.5 mg/ml total peptide in the final adjuvant emulsion. The different solutions, the respective peptides formulated in them, and the method of formulation are described below.

Solution 1 (Acidic Pool): Peptides CEA.691H5, p53.149M2, MAGE3.11215, and PADRE were solubilized in 0.1875M acetic acid. The CEA.691H5 peptide was solubilized first by 2 minutes of vortexing at high speed, followed by 5-10 minutes of sonication (35-40° C.). The other peptides were added one at a time and solubilized by vortexing for 1-2 minutes.

Solution 2 (Basic Pool): Peptides CEA.24V9, CEA.605D6, HER2.689, MAGE2.157, and p53.139L2B3 were solubilized in 0.1M NaOH. Peptides were readily solubilized with brief vortexing (1-2 minutes).

Solution 3 (DMSO): Peptide HER2.369V2V9 was solubilized in DMSO with vortexing (2 minutes) and heating (35-40° C.).

All Solutions were stored at 4° C. until they were combined to generate Pool 4 which contains a mixture of all 10 peptides.

Pool 4 (Combination of Solutions 1, 2, and 3): Solutions 1, 2 and 3 were combined in a 4:5:1 ratio (v:v, e.g. 0.8:1:0.2 ml respectively), or in a 3.2:4:1 ratio (v:v, e.g. 0.8:1:0.25 ml respectively), which resulted in precipitation of some peptides. The combined pool was buffered with 0.2 ml of 62.5 mM sodium phosphate (pH 7) and pH-adjusted to pH 7 with 0.5 M NaOH (approximately 178 µl per 2.5 ml of final pool 4 after buffering and water addition), then brought to volume (2.5 ml) with water-for-injection (WFI).

The final Pool 4 solution was then combined 1:1 v:v with Montanide® ISA 51 (Seppic Inc.) and emulsified by homogenization using a Silverson L4RT homogenizer fitted with a ⅜ inch mini-micro tubular probe. Typically, a 10 mg/ml research emulsion was prepared in a total volume of 1.5~5 ml, with the tube kept cool on ice during preparation. Initially, the probe was carefully inserted into the oil layer near the water/oil interface and the oil layer was mixed at a low speed before the probe was transferred to the bottom of the tube and the speed adjusted to 8,000 rpm. Homogenization was performed for a total of 30 minutes and an even emulsion was produced by repeatedly raising and lowering the tube during this interval. The final EP-2101 emulsified product was kept at 4° C., prior to injection of animals.

Emulsions at a 2.5 mg/ml and 5 mg/ml total peptide dose were prepared at a scale of approximately 25 ml, 500 ml, or 1 liter using probes and mixing screens of appropriate diameter and pore size.

Placebo emulsion (emulsion control) was prepared as described above, except Solutions 1, 2, and 3 did not contain peptides.

Immunization of Mice and In Vitro Expansion of In Vivo-Primed CTLs

HLA-A2.1/$K^b$ transgenic mice were immunized with EP-2101 or placebo emulsion subcutaneously at the tail base in an injection volume of 50-100 µl/animal. Eleven to fourteen days after immunization, animals from each experimental group were sacrificed and a single cell suspension was prepared from a pool of mouse spleens. Individual cultures of splenocytes ($20\text{-}25\times10^6$ cells per culture) were then stimulated in vitro in upright 25 cm² flasks with individual CTL epitopes represented in EP-2101 (1 µg/ml final peptide concentration in 10 ml of RPMI-10 medium; duplicate or triplicate cultures established per epitope). As APCs, $1\text{-}1.25\times10^7$ irradiated (4000 rad) LPS-activated blasts were added to each culture. LPS blasts were prepared by stimulating spleen cells from untreated HLA-A2.1/$K^b$ mice in vitro with 6.25 µg/ml LPS (Sigma Chemical Co., St. Louis, Mo.) and 7 µg/ml dextran sulfate (500,000 M. W., 17% sulfur, Pharmacia Bioprocess Technology, Uppsala, Sweden) for 3 days at 37° C.

Splenocyte cultures stimulated with EP-2101 peptide were incubated for 6 days at 37° C. in 5% $CO_2$ before each culture was measured for CTL activity using the IFN-γ in situ ELISA, as described below.

Measurement of CTL Activity

Six days after initiation of culture, CTL activity from individual cultures was measured by the IFN-γ in situ ELISA as previously described (McKinney, D. M, et al., *J Immunol Methods* 237:105 (2000)). Briefly, CTL effector cells ($4\times10^5$)

cells were added to 4 or 6 wells in a 96-well plate (flat-bottom, precoated with a capture anti-IFN-γ monoclonal antibody). Cells were then serially diluted 4-fold in RPMI-10 medium until a final concentration of 391 cells/well was achieved. Jurkat-A2.1/K$^b$ tumor cells (10$^5$/well) were then added to each well. Half of the wells in each replicate (cells were plated in replicates of 6 or 4 wells) received 10 μg/ml of CTL peptide and the remaining wells received medium. After overnight incubation, wells were washed and developed to determine IFN-γ content by sequential treatment with a secondary biotinylated anti-IFN-γ monoclonal antibody, streptavidin peroxidase, and finally substrate. The pg of IFN-γ released per well by CTLs in the presence or absence of peptide was calculated by measuring absorbance with an automated ELISA reader and extrapolating the IFN-γ concentration from a standard curve. The data is expressed in secretory units (SU) as calculated by the method described by McKinney et al. (McKinney, D. M, et al., *J Immunol Methods* 237:105 (2000)). One secretory unit is defined as the release of 100 pg/well of IFN-γ by 10$^6$ effector cells.

Measurement of CTL and HTL Induction by the ELISPOT Assay

ELISPOT assays to measure CTL or HTL responses induced by EP-2101 were performed according to previously published protocols (Lewis J J, et al., *Int J Cancer* 87:391 (1998)). Briefly, flat bottom 96-well nitrocellulose plates (IP, Millipore) were coated with IFN-γ mAb (10 μg/ml, clone R4-6A2, PharMingen) and incubated overnight at 4° C. After washing with PBS, plates were blocked with RPMI-10 medium for 1 h at 37° C. Four×10$^5$ CD8$^+$ cells or CD4$^+$ cells (isolated with Miltenyi isolation system from EP-2101-immunized splenocytes) and 5×10$^4$ Jurkat-A2.1/K$^b$ cells (for CD8$^+$ cells) or 10$^5$ γ-irradiated naïve spleen cells (for CD4$^+$ cells, treated with erythrocyte lysis buffer) were added to each well. Wells also received 10 μg/ml of CTL or HTL peptide to test for induction of responses against EP-2101 epitopes or an identical concentration of an irrelevant peptide. The irrelevant peptide for the CD8 ELISPOT assay was the HCV core.132 peptide (DLMGYIPLV (SEQ ID NO: )) and the HCV NS3.1253 peptide (GYKVLVLNPSVAATL (SEQ ID NO: )) for the CD4 ELISPOT assay. After incubation, the plates were washed thoroughly with PBS/0.05% Tween 20 and biotinylated IFN-γ mAb (2 μg/ml, clone XMG1.2, PharMingen) was added to each well and incubated for 2-4 h at 37° C. After washing 4 times with PBS/0.05% Tween 20, Vectastain ABC peroxidase (Vectastain Elite kit; Vector laboratories, Inc., Burlingame, Calif., USA) was added to the wells and plates were incubated for 1 h at room temperature. The plates were washed again 3 times with PBS/0.05% Tween 20 followed by 3 washes with PBS. One hundred μl of AEC solution (Sigma Chemical Co) was added to develop the spots. The reaction was stopped after 4-6 minutes under running tap water. The spots were counted by computer-assisted image analysis (Zeiss KS ELISPOT Reader, Jena, Germany). The net number of spots/10$^6$ CD8$^+$ cells or CD4$^+$ cells was calculated as (number of spots against relevant peptide)−(number of spots with irrelevant control peptide)×2.5.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications and sequence listings cited herein are hereby incorporated by reference in their entirety for all purposes.

TABLE 1

Sequence of Peptides in Drug Substance

| Peptide Identification | Sequence | Epitope | Type |
| --- | --- | --- | --- |
| 965.10 | aKXVAAWTLKAAa (SEQ ID NO: 1) | pADRE® | Universal Helper T Cell Epitope |
| 1013.08 | RLLQETELV (SEQ ID NO: 2) | HER-2/neu.689 | Wild-type |
| 1090.01 | YLQLVFGIEV (SEQ ID NO: 3) | MAGE2.157 | Wild-type |
| 1243.08 | LLTFWNPPV (SEQ ID NO: 4) | CEA.24V9 | Fixed-Anchor Analog |
| 1295.03 | SMPPPGTRV (SEQ ID NO: 5) | p53.149M2 | Fixed-Anchor Analog |
| 1323.06 | KLBPVQLWV (SEQ ID NO: 6) | p53.139L2B3 | Fixed-Anchor Analog |
| 1334.10 | KVFGSLAFV (SEQ ID NO: 7) | HER-2/neu.369V2V9 | Fixed-Anchor Analog |
| 1350.01 | YLSGADLNL (SEQ ID NO: 8) | CEA.605D6 | Heterocltic Analog |
| 1352.02 | IMIGHLVGV (SEQ ID NO: 9) | CBA.691H5 | Heterocltic Analog |
| 1352.03 | KVAEIVHFL (SEQ ID NO: 10) | MAGE-3.112I5 | Heteroclitic Analog | a = d-alanine, B = α-aminoisobutyric acid, X = cyclohexylalanine

TABLE 2

Overview of current cancer vaccine approaches.

| APPROACH | DESCRIPTION | ISSUES | STRENGTHS |
|---|---|---|---|
| Whole Cell Vaccines | Involve the administration of whole cancer cells with adjuvants which serve to potentiate the immune response | Often difficult to obtain tumor cells Patient variability Single patient product Has relatively low concentration of relevant TAA epitopes | Likely to have novel TAA |
| Cell Lysate Vaccines | Consist of lysed allogeneic cancer cell membrane particles that are ingested by macrophages and presented as tumor antigens to effector cells | Often difficult to obtain tumor cells Patient variability Single patient product Has relatively low concentration of relevant TAA epitopes | Likely to have novel TAA |
| Idiotypic Vaccines | Contain proteins derived from individual patient tumors or from specific tumor types | Often difficult to obtain tumor cells Patient variability Single patient product Has relatively low concentration of relevant TAA epitopes | Specific TAA |
| Whole Antigen Vaccines | | Limited disease coverage Difficult to break tolerance | Complex "natural" immune responses may be elicited Relatively easy single compound manufacture |
| Viral oncolysate vaccines | Consist of vaccinia virus infected cancer cell, lysed to form membrane segments expressing both vaccinia and cancer cell antigens | Often difficult to obtain tumor cells Not always possible to infect cancer cells Patient specific treatment Has relatively low concentration of relevant TAA epitopes | |
| Shed antigen vaccines | Similar to whole cell and lysate vaccines but are partially purified | Difficult to purify antigens Patient specific treatment Has relatively low concentration of relevant TAA epitopes | Likely to have novel TAA |
| Genetically modified tumor cell vaccines | A number of avenues are being explored including the transduction of cells with GM-CSF | Very difficult to obtain tumor tissues and grow to allow stable transduction Patient specific treatment | Cells contain novel TAA and adjuvants |
| Peptide Vaccines | Synthetic peptides are produced that correspond to tumor associated antigens. Designed to stimulate a cytotoxic T-Cell response (CTL) | Need to choose correct peptides to elicit an effective immune response Restriction to HLA subtype or HLA supertypes | Single preparation used for multiple patients and possibly multiple diseases Possible to combine various antigens/ targets Reproducible antigen production Able to break tolerance Able to elicit |

TABLE 2-continued

Overview of current cancer vaccine approaches.

| APPROACH | DESCRIPTION | ISSUES | STRENGTHS |
|---|---|---|---|
| | | | responses to subdominant epitopes Can be directed to supertypes for broad population coverage |
| Carbohydrate vaccines | Synthetically produced tumor associated carbohydrates, designed to stimulate an antibody response against the carbohydrate antigens | May need CTL response as well as humoral response Carbohydrate antigens are HTL dependent | Single preparation used for multiple patients and possibly multiple diseases |

TABLE 3

| | POSITION 2 (Primary Anchor) | POSITION 3 (Primary Anchor) | POSITION C Terminus (Primary Anchor) |
|---|---|---|---|
| SUPERMOTIFS | | | |
| A1 | T, I, *L, V, M, S* | | F, W, Y |
| A2 | L, I, V, M, *A, T, Q* | | I, V, *M, A, T, L* |
| A3 | V, S, M, A, *T, L, I* | | R, K |
| A24 | Y, F, *W, I, V, L, M, T* | | F, I, *Y, W, L, M* |
| B7 | P | | V, I, L, F, *M, W, Y, A* |
| B27 | R, H, K | | F, Y, L, *W, M, I, V, A* |
| B44 | E, *D* | | F, W, L, I, M, V, A |
| B58 | A, T, S | | F, W, Y, *L, I, V, M, A* |
| B62 | Q, L, I, V, M, *P* | | F, W, Y, *M, I, V, L, A* |
| MOTIFS | | | |
| A1 | T, S, M | | Y |
| A1 | | D, E, *A, S* | Y |
| A2.1 | L, M, *V, Q, I, A, T* | | V, *L, I, M, A, T* |
| A3 | L, M, V, I, S, A, T, F, *C, G, D* | | K, Y, R, *H, F, A* |
| A11 | V, T, M, L, I, S, A, *G, N, C, D, F* | | K, *R, Y, H* |
| A24 | Y, F, W, *M* | | F, L, I, W |
| A*3101 | M, V, T, *A, LP, I, S* | | R, *K* |
| A*3301 | M, V, A, L, F, *I, S, T* | | R, K |
| A*6801 | A, V, T, *M, S, L, I* | | R, K |
| B*0702 | P | | L, M, F, *W, Y, A, I, V* |
| B*3501 | P | | L, M, F, W, Y, *I, V, A* |
| B51 | P | | L, I, V, F, *W, Y, A, M* |
| B*5301 | P | | I, M, F, W, Y, *A, L, V* |
| B*5401 | P | | A, T, I, V, *L, M, F, W, Y* |

Bolded residues are preferred, italicized residues are less preferred: A peptide is considered motif-bearing if it has primary anchors at each primary anchor position for a motif or supermotif as specified in the above table.

TABLE 3a

| | POSITION 2 (Primary Anchor) | POSITION 3 (Primary Anchor) | POSITION C Terminus (Primary Anchor) |
|---|---|---|---|
| SUPERMOTIFS | | | |
| A1 | T, I, *L, V, M, S* | | F, W, Y |
| A2 | V, *Q, A, T* | | I, V, *L, M, A, T* |
| A3 | V, S, M, A, *T, L, I* | | R, K |
| A24 | Y, F, *W, I, V, L, M, T* | | F, I, *Y, W, L, M* |
| B7 | P | | V, I, L, F, *M, W, Y, A* |
| B27 | R, H, K | | F, Y, L, *W, M, I, V, A* |

TABLE 3a-continued

|  | POSITION 2 (Primary Anchor) | POSITION 3 (Primary Anchor) | POSITION C Terminus (Primary Anchor) |
|---|---|---|---|
| B58 | A, T, S |  | F, W, Y, *L, I, V, M, A* |
| B62 | Q, L, *I, V, M, P* |  | F, W, Y, *M, I, V, L, A* |
| MOTIFS |  |  |  |
| A1 | T, S, M |  | Y |
| A1 |  | D, E, *A, S* | Y |
| A2.1 | *V, Q, A, T*\* |  | V, *L, I, M, A, T* |
| A3.2 | L, M, V, I, S, A, T, F, *C, G, D* |  | K, Y, R, *H, F, A* |
| A11 | V, T, M, L, I, S, A, *G, N, C, D, F* |  | K, *R, H, Y* |
| A24 | Y, F, W |  | F, L, I, W |

*If 2 is V, or Q, the C-term is not L

Bolded residues are preferred, italicized residues are less preferred: A peptide is considered motif-bearing if it has primary anchors at each primary anchor position for a motif or supermotif as specified in the above table.

TABLE 4

SUPER MOTIFS

| | | 1 | 2 | 3 | POSITION 4 | 5 | 6 | 7 | 8 | C-terminus |
|---|---|---|---|---|---|---|---|---|---|---|
| A1 | | | 1°Anchor T, I, L, V, M, S | | | | | | | 1°Anchor F, W, Y |
| A2 | | | 1°Anchor L, I, V, M, A, T, Q | | | | | | | 1°Anchor L, I, V, M, A, T |
| A3 | preferred | | 1°Anchor V, S, M, A, T, L, I | Y, F, W, (4/5) | | | | | | 1°Anchor R, K |
| | deleterious | D, E (3/5); P, (5/5) | | D, E, (4/5) | | | | | | |
| A24 | preferred | | 1°Anchor Y, F, W, I, V, L, M, T | | | | | | | 1°Anchor F, I, Y, W, L, M |
| B7 | preferred | F, W, Y (5/5) | 1°Anchor P | F, W, Y (4/5) | | | | | | 1°Anchor V, I, L, F, M, W, Y, A |
| | deleterious | L, I, V, M, (3/5) D, E (3/5); P (5/5); G (4/5); A (3/5); Q, N, (3/5) | | | | D, E, (3/5) | Y, F, W, (3/5) | Y, F, W, (4/5) | F, W, Y, (3/5) | |
| B27 | | | 1°Anchor R, H, K | | | | | | | 1°Anchor F, Y, L, W, M, V, A |
| B44 | | | 1°Anchor E, D | | | | | G, (4/5) | Q, N, (4/5) | 1°Anchor F, W, Y, L, I, M, V, A |
| B58 | | | 1°Anchor | | | | | | D, E, (4/5) | 1°Anchor |
| B62 | | | 1°Anchor Q, L, I, V, M, P | | | | | | | |

MOTIFS

| | | 1 | 2 | 3 | POSITION 4 | 5 | 6 | 7 | 8 | 9 or C-terminus | C-terminus |
|---|---|---|---|---|---|---|---|---|---|---|---|
| A1 9-mer | preferred | G, F, Y, W, | A, T, S | D, E, A, | Y, F, W, | | P, | D, E, Q, N, | Y, F, W, | F, W, Y, L, I, V, M, A | |
| | deleterious | D, E, | 1°Anchor S, T, M, | R, H, K, L, I, V, M, P, | A, | G, | A, | | | 1°Anchor F, W, Y, M, I, V, L, A | |
| A1 9-mer | preferred | G, R, H, K | A, S, T, C, L, I V, M, | 1°Anchor D, E, A, S | G, S, T, C, | | A, S, T, C, | L, I, V, M, | D, E, | 1°Anchor Y | |
| | deleterious | A | R, H, K, D, E, P, Y, F, W, | | D, E, | P, Q, N, | R, H, K, | P, G, | G, P, | 1°Anchor Y | |
| A1 10-mer | preferred | Y, F, W, | 1°Anchor S, T, M | D, E, A, Q, N, | A, | Y, F, W, Q, N, | R, H, K, | P, A, S, T, C, | G, D, E, | P, | 1°Anchor Y |

TABLE 4-continued

| | | | | | | | | | | |
|---|---|---|---|---|---|---|---|---|---|---|
| A1 10-mer | deleterious | G, P, | | R, H, K, G, L, I | D, E, | R, H, K, | Q, N, A | R, H, K, Y, F, W, | R, H, K, | A, | |
| | preferred | Y, F, W, | S, T, C, L, I, V, M, | R, H, K, Y, M, | A, | Y, F, W, | | P, G, | | Y, F, W, | 1°Anchor Y |
| A2.1 9-mer | deleterious | R, H, K, | R, H, K, D, E, P, Y, F, W, | 1°Anchor D, E, A, S | | P, | | | | Q, N, | |
| | preferred | Y, F, W, | 1°Anchor L, M, I, V, Q, A, T | Y, F, W, | S, T, C, | Y, F, W, | G, | A, | P, | 1°Anchor V, L, I, M, A, T | |
| A2.1 10-mer | deleterious | D, E, P, | | D, E, R, K, H | | | | | | | |
| | preferred | A, Y, F, W, | 1°Anchor L, M, I, V, Q, A, T | D, E, R, K, H L, V, I, M | G, | | R, K, H G, | D, E, R, K, H | F, Y, W, L, V, I, M | | 1°Anchor V, L, I, M, A, T |
| A3 | deleterious | D, E, P, | | D, E, | R, K, H, A | P, | | R, K, H, | D, E, R, K, | | |
| | preferred | R, H, K, | 1°Anchor L, M, V, I, S, A, T, F, C, G D | Y, F, W, | P, R, H, K, Y, F, W, | A, | Y, F, W, | | | H, P, | 1°Anchor K, Y, R, H, F, A |
| A11 | deleterious | D, E, P, | | D, E | Y, F, W, | A, | Y, F, W, | Y, F, W, | | | |
| | preferred | A, | 1°Anchor V, T, L, M, I, S, A, G, N, C, D, F | Y, F, W, | | | | | P, | | 1°Anchor K, R Y, H |
| A24 9-mer | deleterious | D, E, P, | | | S, T, C | | | | A, Y, F, W, | G, Y, F, W, | |
| | preferred | Y, F, W, R, H, K, | 1°Anchor Y, F, W, M | D, E, | | | | | | | 1°Anchor F, L, I, W |
| A24 10-mer | deleterious | D, E, G, | | | G, P, | Q, N, P, Y, F, W, P, | D, E, R, H, K, | G, P, | A, Q, N, | | |
| | preferred | G, P, | 1°Anchor Y, F, W, M | | Q, N P, | R, H, K | | | A Y, F, W, | | |
| A3101 | deleterious | R, H, K, | | G, D, E, | | | D, E | D, E, Y, F, W, | A, Y, F, W, | Q, N, A, P, | D, E, A, |
| | preferred | | 1°Anchor M, V, T, A, L, I, S | Y, F, W, | | | | | | | 1°Anchor R, K |
| A3301 | deleterious | D, E, P, | | D, E, | | A, D, E, | D, E, | D, E, A, Y, F, W | D, E, | | |
| | preferred | | 1°Anchor M, V, A, L, F, I, S, T | Y, F, W | | | | | | | 1°Anchor R, K |
| A6801 | deleterious | G, P | | D, E | | Y, F, W, L, I, V, M | | Y, F, W, | P, | | |
| | preferred | Y, F, W, S, T, C, | 1°Anchor A, V, T, M, S L, I | | | | | | | | 1°Anchor R, K |
| B0702 | deleterious | G, P, | | D, E, G, R, H, K, | | R, H, K, R, H, K, | R, H, K, | R, H, K, | A, P, A, | | |
| | preferred | R, H, K, F, W, Y, | 1°Anchor P | | | | | | | | 1°Anchor L, M, F, W, Y, A, I, V |
| B3501 | deleterious | D, E, Q, N, P, | | D, E, P, F, W, Y, | D, E, | D, E, | G, D, E, | Q, N, F, W, Y, | D, E, | | |
| | preferred | F, W, Y, L, I, V, M, | 1°Anchor P | | | | | | | | 1°Anchor L, M, F, W, Y, I V, A |
| B51 | deleterious | A, G, P, | | F, W, Y, | S, T, C | G, F, W, Y, | G, | G, | F, W, Y, | | |
| | preferred | L, I, V, M, F, W, Y, | 1°Anchor P | | | | | | | | 1°Anchor L, I, V, F, W Y, A, M |

TABLE 4-continued

| | | | | | | | | | |
|---|---|---|---|---|---|---|---|---|---|
| B5301 | deleterious | A, G, P, D, E, R, H, K, S, T, C, | | | D, E, | | D, E, Q, N, | G, D, E, | |
| | preferred | L, I, V, M, F, W, Y, | 1°Anchor P | S, T, C, | F, W, Y, | G, | L, I, V, M, F, W, Y, | F, W, Y, | 1°Anchor I, M, F, W, Y, *A, L, V* |
| B5401 | deleterious | A, G, P, Q, N, | | | | | R, H, K, Q, N, | D, E, | |
| | preferred | F, W, Y, | 1°Anchor P | F, W, Y, L, I, V, M, | L, I, V, M, | G, | A, L, I, V, M, | F, W, Y, A, P, | 1°Anchor A, T, I, V, *L, M, F, W, Y* |
| | deleterious | G, P, Q, N, D, E, | | G, D, E, S, T, C, | R, H, K, D, E, | | Q, N, D, G, E, | D, E, | |

Italicized residues indicate less preferred or "tolerated" residues.

The information in Table II is specific for 9-mers unless otherwise specified.

Secondary anchor specificities are designated for each position independently.

TABLE 5

Expression of Tumor Associated Antigen (TAA)

| TAA | % of Tumors Expressing the TAA | | |
|---|---|---|---|
| | Colon Cancer | Breast Cancer | Lung Cancer |
| CEA | 95 | 50 | 70 |
| P53 | 50 | 50 | 40-60 |
| MAGE 2/3 | 20-30 | 20-30 | 35 |
| HER2/neu | 28-50 | 30-50 | 20-30 |
| Total | 99 | 86-91 | 91-95 |

TABLE 6

| HLA-supertype | Allelle-specific HLA-supertype members | |
|---|---|---|
| | Verified[a] | Predicted[b] |
| A1 | A*0101, A*2501, A*2601, A*2602, A*3201, A*2902 | A*0102, A*2604, A*3601, A*4301, A*8001 |
| A2 | A*0201, A*0202, A*0203, A*0204, A*0205, A*0206, A*0207, A*0209, A*0214, A*6802, A*6901 | A*0208, A*0210, A*0211, A*0212, A*0213 |
| A3 | A*0301, A*1101, A*3101, A*3301, A*6801 | A*0302, A*1102, A*2603, A*3302, A*3303, A*3401, A*3402, A*6601, A*6602, A*7401 |
| A24 | A*2301, A*2402, A*3001 | A*2403, A*2404, A*3002, A*3003 |
| B7 | B*0702, B*0703, B*0704, B*0705, B*1508, B*3501, B*3502, B*3503, B*3503, B*3504, B*3505, B*3506, B*3507, B*3508, B*5101, B*5102, B*5103, B*5104, B*5105, B*5301, B*5401, B*5501, B*5502, B*5601, B*5602, B*6701, B*7801 | B*1511, B*4201, B*5901 |
| B27 | B*1401, B*1402, B*1509, B*2702, B*2703, B*2704, B*2705, B*2706, B*3801, B*3901, B*3902, B*7301 | B*2701, B*2707, B*2708, B*3802, B*3903, B*3904, B*3905, B*4801, B*4802, B*1510, B*1518, B*1503 |
| B44 | B*1801, B*1802, B*3701, B*4402, B*4403, B*4404, B*4001, B*4002, B*4006 | B*4101, B*4501, B*4701, B*4901, B*5001 |
| B58 | B*5701, B*5702, B*5801, B*5802, B*1516, B*1517 | |
| B62 | B*1501, B*1502, B*1513, B*5201 | B*1301, B*1302, B*1504, B*1505, B*1506, B*1507, B*1515, B*1520, B*1521, B*1512, B*1514, B*1510 |

TABLE 7

Expression of Tumor Associated Antigen (TAA)

| TAA | % of Tumors Expressing the TAA | | |
|---|---|---|---|
| | Colon Cancer | Breast Cancer | Lung Cancer |
| CEA | 95 | 50 | 70 |
| P53 | 50 | 50 | 40-60 |
| MAGE 2/3 | 20-30 | 20-30 | 35 |
| HER2/neu | 28-50 | 30-50 | 20-30 |
| Total | 99 | 86-91 | 91-95 |

TABLE 8

Incidence and survival rate of patients with breast, colon, or lung cancer in the United States

| | Estimated New Cases | Estimate | 5-Year relative survival rates | | |
|---|---|---|---|---|---|
| | 1998 | Deaths 1998 | 1974-76 | 1980-82 | 1986-1993 |
| Breast | 180,300 | 43,900 | 75% | 77% | 80% |
| Colon | 95,600 | 47,700 | 50% | 56% | 63% |
| Lung | 171,500 | 160,100 | 12% | 14% | 14% |

Source: Cancer Statistics 1998. January/February 1998, Vol. 48, No. 1

[a]Verified alleles include alleles whose specificity has been determined by pool sequencing analysis, peptide binding assays, or by analysis of the sequences of CTL epitopes.

[b]Predicted alleles are alleles whose specificity is predicted on the basis of B and F pocket structure to overlap with the supertype specificity.

TABLE 9

Population coverage by HLA class I supertype epitopes.

| | | Minimal Alleic Frequency | | | | | |
|---|---|---|---|---|---|---|---|
| Supertype | Representative HLA Molecules* | Caucasian | Black | Japanese | Chinese | Hispanic | Average |
| A2 | 2.1, 2.2, 2.3, 2.5, 2.6, 2.7, 68.02 | 45.8 | 39.0 | 42.4 | 45.9 | 43.0 | 43.2 |
| A3 | 3, 11, 31, 33, 68.01 | 37.5 | 42.1 | 45.8 | 52.7 | 43.1 | 44.2 |
| B7 | 7, 51, 53, 35, 54 | 43.2 | 55.1 | 57.1 | 43.0 | 49.3 | 49.5 |
| | Total Population Coverage | 84.3 | 86.8 | 89.5 | 89.8 | 86.8 | 87.4 |

TABLE 10

Tumor Associated Antigens and Genes (TAA)

| ANTIGEN | REFERENCE |
|---|---|
| MAGE 1 | (Traversari C., Boon T, J. Ex. Med 176: 1453, 1992) |
| MAGE 2 | (De Smet C., Boon T, Immunogenetics, 39(2)121-9, 1994) |
| MAGE 3 | (Gaugler B., Boon T, J. Ex. Med 179: 921, 1994) |
| MAGE-11 | (Jurk M., Winnacker L, Int. J. Cancer 75, 762-766, 1998) |
| MAGE-A10 | (Huang L., Van Pel A, J.Immunology, 162: 6849-6854) |
| BAGE | (Boel P., Bruggen V, Immunity 2: 167, 1995) |
| GAGE | (Eynde V., Boon T, J. Exp. Med 182: 689, 1995) |
| RAGE | (Gaugler B., Eynde V, Immunogenetics, 44: 325, 1996) |
| MAGE-C1 | (Lucas S., Boon T, Cancer Research, 58, 743-752, 1998) |
| LAGE-1 | (Lethel B., Boon T, Int J cancer, 10; 76(6) 903-908 |
| CAG-3 | (Wang R--Rosenberg S, J.Immunology, 161: 3591-3596, 1998) |
| DAM | (Fleischhauer K., Traversari C, Cancer Research, 58, 14, 2969, 1998) |
| MUC1 | (Karanikas V., McKenzie IF, J.clnical investigation, 100: 11, 1-10, 1997) |
| MUC2 | (Bohm C., Hanski, Int.J.Cancer 75, 688-693, 1998) |
| MUC18 | (Putz E., Pantel K, Cancer Res 59(1): 241-248, 1999) |
| NY-ES0-1 | (Chen Y., Old LJ PNAS, 94, 1914-18, 1997) |
| MUM-1 | (Coulie P., Boon T, PNAS 92: 7976, 1995) |
| CDK4 | (Wolfel T., Beach D, Science 269: 1281, 1995) |
| BRCA2 | (Wooster R---Stratton M, Nature, 378, 789-791, 1995) |
| NY-LU-1 | (Gure A., Chen, Cancer Research, 58, 1034-41, 1998) |
| NY-LU-7 | (Gure A., Chen, Cancer Research, 58, 1034-41, 1998) |
| NY-LU-12 | (Gure A., Chen, Cancer Research, 58, 1034-41, 1998) |
| CASP8 | (Mandruzzato S., Bruggen P, J. Ex. Med 186, 5, 785-793, 1997) |
| RAS | (Sidransky D., Vogelstein B, Science, 256: 102) |
| KIAA0205 | (Gueguen M., Eynde, J.Immunology, 160: 6188-94, 1998) |
| SCCs | (Molina R., Ballesta AM, Tumor Biol, 17(2): 81-9, 1996) |
| p53 | (Hollstein M., Harris CC, Science, 253, 49-53, 1991) |
| p73 | (Kaghad M., Caput D, Cell; 90(4): 809-19, 1997) |
| CEA | (Muraro R., Schlom J, Cancer Research, 45: 5769-55780, 1985) |
| Her 2/neu | (Disis M., Cheever M, Cancer Res 54: 1071, 1994) |
| Melan-A | (Coulie P., Boon T, J. Ex. Med, 180: 35, 1994) |
| gp100 | (Bakker A., Figdor, J. Ex. Med 179: 1005, 1994) |
| Tyrosinase | (Wolfel T., Boon T, E. J. I 24: 759, 1994) |
| TRP2 | (Wang R., Rosenberg S. A, J. Ex. Med 184: 2207, 1996) |
| gp75/TRP1 | (Wang R., Rosenberg S. A, J. Ex. Med 183: 1131, 1996) |
| PSM | (Pinto J. T., Heston W. D. W., Clin Cancer Res 2(9); 1445-1451, 1996) |
| PSA | (Correale P., Tsang K, J. Natl cancer institute, 89: 293-300, 1997) |
| PT1-1 | (Sun Y., Fisher PB, Cancer Research, 57(1): 18-23, 1997) |
| B-catenin | (Robbins P., Rosenberg SA, J. Ex. Med 183: 1185, 1996) |
| PRAME | (Neumann E., Seliger B, Cancer Research, 58, 4090-4095, 1998) |
| Telomearse | (Kishimoto K., Okamoto E, J Surg Oncol, 69(3): 119-124, 1998) |
| FAK | (Kornberg LJ, Head Neck, 20(8): 745-52, 1998) |
| Tn antigen | (Wang Bl, J Submicrosc Cytol Path, 30(4): 503-509, 1998) |
| cyclin D1 protein | (Linggui K., Yaowu Z, Cancer Lett 130(1-2), 93-101, 1998) |
| NOEY2 | (Yu Y., Bat RC, PNAS, 96(1): 214-219, 1999) |
| EGF-R | (Biesterfeld S.---- Cancer Weekly, Feb. 15, 1999) |
| SART-1 | (Matsumoto H., Itoh K, Japanese Journal of Cancer Research, 59, iss12, 1292-1295, 1998) |
| CAPB | (Cancer Weekly, Mar. 29, 4-5, 1999) |
| HPVE7 | (Rosenberg S. A. Immunity, 10, 282-287, 1999) |
| p15 | (Rosenberg S. A., Immunity, 10, 282-287, 1999) |
| Folate receptor | (Gruner B. A., Weitman S. D., Investigational New Drugs, Vol16, iss3, 205-219, 1998) |
| CDC27 | (Wang R. F., Rosenberg SA, Science, vol 284, 1351-1354, 1999) |
| PAGE-1 | (Chen, J. Biol. Chem: 273: 17618-17625, 1998) |

TABLE 10-continued

Tumor Associated Antigens and Genes (TAA)

| ANTIGEN | REFERENCE |
|---|---|
| PAGE-4 | (Brinkmann: PNAS, 95: 10757, 1998) |
| Kallikrein 2 | (Darson: Urology, 49: 857-862, 1997) |
| PSCA | (Reiter R., PNAS, 95: 1735-1740, 1998) |
| DD3 | (Bussemakers M. J. G, European Urology, 35: 408-412, 1999) |
| RBP-1 | (Takahashi T., British Journal of Cancer, 81(2): 342-349, 1999) |
| RU2 | (Eybde V. D., J. Exp. Med, 190 (12): 1793-1799, 1999) |
| Folate binding protein | (Kim D., Anticancer Research, 19: 2907-2916, 1999) |
| EGP-2 | (Heidenreich R., Human Gene Therapy, 11: 9-19, 2000) |

TABLE 11

Tumor-associated antigen (TAA) sequences

CEA SEQ ID NO: 11
MESPSAPPHRWCIPWQRLLLTASLLTFWNPPTTAKLTIESTPFNVAEGKE
VLLLVHNLPQHLFGYSWYKGERVDGNRQIIGYVIGTQQATPGPAYSGREI
IYPNASLLIQNIIQNDTGFYTLHVIKSDLVNEEATGQFRVYPELPKPSIS
SNNSKPVEDKDAVAFTCEPETQDATYLWWVNNQSLPVSPRLQLSNGNRTL
TLFNVTRNDTASYKCETQNPVSARRSDSVILNVLYGPDAPTISPLNTSYR
SGENLNLSCEAASNPPAQYSWFVNGTFQQSTQELFIPNITVNNSGSYTCQ
AHNSDTGLNRTTVTTITVYAEPPKPFITSNNSNPVEDEDAVALTCEPEIQ
NTTYLWWVNNQSLPVSPRLQLSNDNRTLTLLSVTRNDVGPYECGIQNELS
VDHSDPVILNVLYGPDDPTISPSYTYYRPGVNLSLSCHAASNPPAQYSWL
IDGNIQQHTQELFISNITEKNSGLYTCQANNSASGHSRTTVKTITVSAEL
PKPSISSNNSKPVEDKDAVAFTCEPEAQNTTYLWWVNGQSLPVSPRLQLS
NGNRTLTLFNVTRNDARAYVCGIQNSVSANRSDPVTLDVLYGPDTPIISP
PDSSYLSGANLNLSCHSASNPSPQYSWRINGIPQQHTQVLFIAKITPNNN
GTYACFVSNLATGRNNSIVKSITVSASGTSPGLSAGATVGIMIGVLVGVA
LI

Her2/neu SEQ ID NO: 12
MELAALCRWGLLLALLPPGAASTQVCTGTDMKLRLPASPETHLDMLRHLY
QGCQVVQGNLELTYLPTNASLSFLQDIQEVQGYVLIAHNQVRQVPLQRLR
IVRGTQLFEDNYALAVLDNGDPLNNTTPVTGASPGGLRELQLRSLTEILK
GGVLIQRNPQLCYQDTILWKDIFHKNNQLALTLIDTNRSRACHPCSPMCK
GSRCWGESSEDCQSLTRTVCAGGCARCKGPLPTDCCHEQCAAGCTGPKHS
DCLACLHFNIISGICELHCPALVTYNTDTFESMPNPEGRYTFGASCVTAC
PYNYLSTDVGSCTLVCPLHNQEVTAEDGTQRCEKCSKPCARVCYGLGMEH
LREVRAVTSANIQEFAGCKKIFGSLAFLPESFDGDPASNTAPLQPEQLQV
FETLEEITGYLYISAWPDSLPDLSVFQNLQVIRGRILHNGAYSLTLQGLG
ISWLGLRSLRELGSGLALIHHNTHLCFVHTVPWDQLFRNPHQALLHTANR
PEDECVGEGLACHQLCARGHCWGPGPTQCVNCSQFLRGQECVEECRVLQG
LPREYVNARHCLPCHPECQPQNGSVTCFGPEADQCVACAHYKDPPFCVAR
CPSGVKPDLSYMPIWKFPDEEGACQPCPINCTHSCVDLDDKGCPAEQRAS
PLTSIISAVVGRLVVVLGVVFGILIKRRQQKIRKYTMRRLLQETELVEPL
TPSGAMPNQAQMRILKETELRKVKVLGSGAFGTVYKGIWIPDGENVKIPV
AIKVLRENTSPKANKEILDEAYYMAGVGSPYVSRLLGICLTSTVQLVTQL
MPYGCLLDHVRENRGRLGSQDLLNWCMQIAKGMSYLEDVRLVHRDLAARN
VLVKSPNHVKITDFGLARLLDIDETEYHADGGKVPIKWMALESILRRRFT
HQSDVWSYGVTVWELMTFGAKPYDGIPAREIPDLLEKGERLPQPPICTID
VYMIMVKCWMIDSECRPRFRELVSEFSRMARDPQRFVVIQNEDLGPASPL
DSTFYRSLLEDDDMGDLVDAEEYLVPQQGFFCPDPAPGAGGMVHHRHRSS
STRSGGGDLTLGLEPSEEEAPRSPLAPSEGAGSDVEDGDLGMGAAKGLQS
LPTHDPSPLQRYSEDPTVPLPSETDGYVAPLTCSPQPEYVNQPDVRPQPS
SPREGPLPAARPAGATLERPKTLSPGKNGVVKDVFAFGGAVENPEYLTPQ
GGAAPQPHPPPAFSPAFDNLYYWDQDPPERGAPPSTFKGTPTAENPEYLG
LDVPV MAGE2 SEQ ID NO: 13
MPLEQRSQHGKPEEGLEARGEALGLVGAQAPATEEQQTASSSSTLVEVTL
GEVPAADSPSPPHSPQGASSFSTTINYTLWRQSDEGSSNQEEEGPRMFPD
LESEFQAAISRKMVELVHFLLLKYRAREPVTKAEMLESVLRNCQDFFPVI
FSKASEYLQLVFGIEVVEVVPISHLYILVTCLGLSYDGLLGDNQVMPKTG
LLIIVLLAIIAIEGDCAPEEKIWEELSMLEVFEGRRDSVFAHPRKLLMQDL
VQENYLEYRQVPGSDPACYEFLWGPRALIETSYVKVLHHTLKIGGEPHIS
YPPLHERALREGEE MAGE3 SEQ ID NO: 14
MPLEQRSQHCKPEEGLEARGEALGLVGAQAPATEEQEAASSSSTLVEVTL
GEVPAAESPDPPQSPQGASSLPTTMNYPLWSQSYEDSSNQEEEGPSTFPD
LESEFQAALSRKVAELVIHFLLLKYRAREPVTKAEMLGSVVGNWQYFFPV
IFSKASSSLQLVFGIELMEVDPIGHLYIFATCLGLSYDGLLGDNQIMPKA
GLLIIVLAIIAREGDCAPEEKIWEELSVLEVFEGREDSILGDPKKLLTQH
FVQENYLEYRQVPGSDPACYEFLWGPRALVETSYYKVLHHMVKISGGPHI
SYPPLHEWVLREGEE p53 SEQ ID NO: 15
MEEPQSDPSVEPPLSQETFSDLWKLLPENNVLSPLPSQAMDDLMLSPDDI
EQWFTEDPGPDEAPRMPEAAPPVAPAPAAPTPAAPAPAPSWPLSSSVPSQ
KTYQGSYGFRLGFLHSGTAKSVTCTYSPALNKMFCQLAKTCPVQLWVDST
PPPGTRVRAMAIYKQSQHMTEVVRRCPHHECSDSDGLAPPQHLIRVEGNL
RVEYLDDRNTFRHSVVVPYEPPEVGSDGTTLHYNYMCNSSCMGGMNRRPI
LTIITLEDSSGNLLGRNSFEVRVCACPGRDRRTEEENLRKKGEPHHELPP
GSTKRALPNNTSSSPQPKKKPLDGEYFTLQIRGRERFEMFRELNEALELK
DAQAGKEPGGSRAHSSKLKSKKGQSTSRHKKLMFKTEGPDSD

TABLE 12

Hepatitis B Virus Core Protein (SEQ ID NO: 16)

MQLFHLCLIISCSCPTVQASKLCLGWLWGMDIDPYKEFGATVELLSFLPS

DFFPSVRDLLDTASALYREALESPEHCSPHHTALRQAILCWGELMTLATW

VGVNLEDPASRDLVVSYVNTNMGLKFRQLLWFHISCLTFGRETVIEYLVS

FGVWIRTPPAYRPPNAPILSTLPETTVVRRRGRSPRRRTPSPRRRRSQSP

RRRRSQSRESQC

TABLE 13

HLA-A2 Supertype Family Alleles

| Prototype Allele | Additional Supertype Alleles |
|---|---|
| HLA-A*0201 | HLA-A*0202, A*0203, A*0204, A*0205, A*0206, A*0207, A*6802, A*6901 |

TABLE 14

List of Vaccine Epitopes

| Epitope | Sequence | Peptide Number | No. A2 Alleles Crossbound[1] | Wild-type Peptide | CTL Response Tumor Cell | Reference for Wild-type or Analog Epitope |
|---|---|---|---|---|---|---|
| Wild-type Epitopes | | | | | | |
| HER-2/neu.689 | RLLQETELV (SEQ ID NO: 2) | 1013.08 | 2 | + | + | Knutson KL, 2001; Rongeun Y, 1999 |
| MAGE-2.157 | YLQLVFGIEV (SEQ ID NO: 3) | 1090.01 | 4 | + | + | Visseren MJ, 1997; Kawashima I, 1998 |
| Fixed-anchor Analogs | | | | | | |
| CEA.24V9 | LLTFWNPPV (SEQ ID NO: 4) | 1243.08 | 4 | + | + | Kawashima I, 1998 |
| HER-2/neu.369V2V9 | KVFGSLAFV (SEQ ID NO: 5) | 1334.10 | 4 | + | + | Keogh E, 2001 |
| p53.139L2B3 | KLBPVQLWV[2] (SEQ ID NO: 5) | 1323.06 | 4 | + | + | Keogh E, 2001 |
| p53.149M2 | SMPPPGTRV (SEQ ID NO: 6) | 1295.03 | 4 | + | + | Keogh E, 2001; Petersen TR, 2001 |
| Heteroclitic Analogs | | | | | | |
| CEA.691H5 | IMIGHLVGV (SEQ ID NO: 7) | 1352.02 | 5 | + | + | Tangri S, 2001 |
| MAGE-3.11215 | KVAEIVHFL (SEQ ID NO: 8) | 1352.03 | 5 | + | + | Tangri S, 2001 |
| CEA.605D6 | YLSGADLNL (SEQ ID NO: 9) | 1350.01 | 3 | + | + | Zaremba S, 1997 |
| Universal Helper T Cell Epitope | | | | | | |
| PADRE | aKXVAAWTLKAAa[3] (SEQ ID NO: 10) | 965.10 | | | | Alexander J, 1994 |

[1]All peptides bind to the prototype HLA-A2.1 molecule.
[2]B indicates α-aminoisobutyric acid.
[3]X indicates cyclohexylalanine and a indicates d-alanine.

TABLE 15

Peptide Solubility

| Peptide | Acidic conditions (pH 2-4)[1] | Basic conditions (pH 9.6-13)[2] | DMSO |
|---|---|---|---|
| 965.10 | + | −[3] | + |
| 1013.08 | +/−[4] | + | + |
| 1090.01 | −[5] | + | + |
| 1243.08 | +[6] | + | + |
| 1295.03 | + | +[7] | + |
| 1323.06 | +[6] | + | + |
| 1334.10 | + | − | + |
| 1350.01 | +[6] | + | + |
| 1352.02 | + | − | + |
| 1352.03 | + | +[7] | + |

[1]0.1% TFA, 0.15-0.1875 M acetic acid, 25 mM pH4 sodium acetate
[2]25 mM pH 9.6 arginine, 25 mM pH 9.6 sodium bicarbonate, 0.1 M NaOH
[3]Not tested in 0.1 M NaOH, assumed insoluble since not soluble under other basic conditions
[4]Not soluble in pH 4 acetate buffer
[5]Not tested in diluted acetic acid, assumed insoluble under these conditions since insoluble under other acidic conditions
[6]Not tested in diluted acetic acid, assumed soluble under these conditions since soluble in 0.1% TFA
[7]Not tested in 0.1 M NaOH, assumed soluble under these conditions since soluble in other basic buffers

TABLE 16

Release Specifications of Bulk Drug Substance Component Peptides

| Test Name | Test Method | Specification |
|---|---|---|
| Appearance | Visual | White to off-white powder |
| Identity | Mass spectrometry | Molecular Weight |
| | Tandem mass spectrometry | Sequence of peptide |
| | Amino acid analysis | Amino acid composition |
| Purity | HPLC | ≧90% |
| Acetate Content | Ion chromatography | Report result |
| Peptide content | AAA or UV | Report results |
| Residual Organic Volatiles | USP 24 <467> | Isopropanol ≦300 ppm |
| | USP 24 <467> | Methylene chloride ≦20 ppm |
| | USP 24 <467> | Acetonitrile ≦100 ppm |

TABLE 16-continued

Release Specifications of Bulk Drug Substance Component Peptides

| Test Name | Test Method | Specification |
|---|---|---|
| Water Content | USP 24 <921> | Report results |
| Endotoxin | USP 24 <85> | ≤0.5 EU/mg |
| Bioburden | USP 24 <61> | Report results |
| Total Fluorine | Combustion/ISE | Report results |
| Total Mass Balance | Calculation NPC + HOAc + H$_2$O | 90-105% |

TABLE 17

Components and Quantitative Composition of EP-2101 Drug Product

| Component Name | Concentration (g/L) |
|---|---|
| Peptide | |
| 965.10 | 0.5 |
| 1013.08 | 0.5 |
| 1090.01 | 0.5 |
| 1243.08 | 0.5 |
| 1295.03 | 0.5 |
| 1323.06 | 0.5 |
| 1334.10 | 0.5 |
| 1350.01 | 0.5 |
| 1352.02 | 0.5 |
| 1352.03 | 0.5 |
| Adjuvant | |
| Montanide ® ISA 51 | 459 |
| Excipients | |
| Sodium acetate | 2.83 |
| Sodium phosphate, dibasic | 0.33 |
| DMSO (USP) | 50.5 |

TABLE 18

Components for Use in the Manufacture of EP-2101 Drug Product
Components for Manufacture of EP-2101 Drug Product

| | |
|---|---|
| Peptides | 1352.02 |
| | 1295.03 |
| | 1352.03 |
| | 965.10 |
| | 1243.08 |
| | 1350.01 |
| | 1013.08 |
| | 1090.01 |
| | 1323.06 |
| | 1334.10 |
| Chemicals/Solutions | Acetic Acid (USP) |
| | NaOH anhydrous (NF) |
| | DMSO (USP) |
| | Na$_2$HPO$_4$•7H$_2$O (USP) |
| | Sterile Water for Injection (USP) |
| Adjuvant | Montanide ® ISA 51 |

TABLE 19

Pool Assignments for EP-2101 Peptide Epitopes

| Peptide | Amino Acid Sequence | Solution 1 | Solution 2 | Solution 3 |
|---|---|---|---|---|
| 965.10 PADRE® | aKXVAAWTLKAAa (SEQ ID NO: 1) | + | | |
| 1013.08 | RLLQETELV (SEQ ID NO: 2) | | + | |
| 1090.01 | YLQLVFGIEV (SEQ ID NO: 3) | | + | |
| 1243.08 | LLTFWNPPV (SEQ ID NO: 4) | | + | |
| 1295.03 | SMPPPGTRV (SEQ ID NO: 5) | + | | |
| 1323.06 | KLBPVQLWV (SEQ ID NO: 6) | | + | |
| 1334.10 | KVFGSLAFV (SEQ ID NO: 7) | | | + |
| 1350.01 | YLSGADLNL (SEQ ID NO: 8) | | + | |
| 1352.02 | IMIGHLVGV (SEQ ID NO: 9) | + | | |

TABLE 19-continued

Pool Assignments for EP-2101 Peptide Epitopes

| Peptide | Amino Acid Sequence | Solution 1 | Solution 2 | Solution 3 |
|---|---|---|---|---|
| 1352.03 | KVAEIVHFL (SEQ ID NO: 10) | | + | |

+ = solution assignment, a = d-alanine, B = α-aminoisobutyric acid, X = cyclohexylalanine

TABLE 20

Specifications of EP-2101 Bulk Drug Product

| Test Name | Test Method | Specification |
|---|---|---|
| Endotoxin | USP 25 <85> | ≦10 EU/ml |
| Sterility | USP 25 <71> | No growth after 14 days |

TABLE 21

Specifications of EP-2101 Drug Product

| Test Name | Test Method | Specification |
|---|---|---|
| Appearance | Visual | White to pale yellow emulsion |
| Endotoxin | USP 25 <85> | ≦20 EU/ml |
| Sterility | USP 25 <71> (conforms with 21 CFR 610.12) | No growth after 14 days |
| Viscosity | Plate and cone | Report value |
| PH | pH electrode | pH 7.0 ± 1.0 |
| Particle size distribution | Laser light diffraction | Report value |
| Peptide concentration of each peptide | HPLC | 0.50 ± 0.25 mg/ml of emulsion |
| Identity | HPLC | Conforms to standard |
| Extractable volume | Syringe withdrawal | ≧1.00 ml |
| Potency | In vivo immunogenicity | Peptide 1352.02: ≧22 SU and ≦2900 SU<br>Peptide 1334.10: ≧8 SU and ≦3300 SU |

TABLE 22

HPLC Parameters for Determination of Peptide Concentration

HPLC Parameters

Mobile Phase A: 0.1% TFA
Mobile Phase B: 0.1% TFA in 80% Acetonitrile in water,
Column: PLRP-S (300 A, 5 μm, 4.6 × 250 mm), Polymer Laboratories
Flow-rate: 1.0 ml/min
Wavelength: 214 nm
Column temperature: 40° C.
Autosampler temperature: Ambient TABLE 22-continued HPLC Parameters for Determination of Peptide Concentration Solvent Gradient

| Time (min) | Flow (ml/min) | % A | % B | Curve |
|---|---|---|---|---|
| 0.00 | 1.0 | 95.0 | 5.0 | N/A |
| 5.00 | 1.0 | 80.0 | 20.0 | Linear |
| 40.00 | 1.0 | 60.0 | 40.0 | Linear |
| 54.00 | 1.0 | 5.0 | 95.0 | Linear |
| 60.00 | 1.0 | 5.0 | 95.0 | Linear |
| 65.00 | 1.0 | 95.0 | 5.0 | Linear |
| 77.00 | 1.0 | 95.0 | 5.0 | Linear |

What is claimed is:

1. A composition, comprising LLTFWNPPV (SEQ ID NO:4), KVFGSLAFV (SEQ ID NO:7), KLBPVQLWV (SEQ ID NO:6), SMPPPGTRV (SEQ ID NO:5), YLSGADLNL (SEQ ID NO: 8), IMIGHLVGV (SEQ ID NO:9), KVAEIVHFL (SEQ ID NO:10), RLLQETELV (SEQ ID NO:2), YLQLVFGIEV (SEQ ID NO:3), and aKXVAAWTLKAAa (SEQ ID NO:1), wherein a in SEQ ID NO:1 is any of D-alanine or L-alanine and wherein X in SEQ ID NO:1 is any of cyclohexylalanine, phenylalanine or tyrosine and wherein B in SEQ ID NO:6 is any of α-amino butyric acid or cysteine.

2. The composition of claim 1, which further comprises an adjuvant.

3. The composition of claim 2, wherein said adjuvant is a mineral oil adjuvant.

4. The composition of claim 1, wherein the first a in SEQ ID NO:1 is L-alanine and the last a in SEQ ID NO:1 is D-alanine.

5. The composition of claim 1, wherein a in SEQ ID NO:1 is D-alanine.

6. The composition of claim 1, wherein X in SEQ ID NO:1 is cyclohexylalanine.

7. The composition of claim 1, wherein the first a in SEQ ID NO:1 is L-alanine and the last a in SEQ ID NO:1 is D-alanine and wherein X in SEQ ID NO:1 is cyclohexylalanine.

8. The composition of claim 1, wherein a in SEQ ID NO:1 is D-alanine and wherein X in SEQ ID NO:1 is cyclohexylalanine.

9. The composition of claim 1, wherein B in SEQ ID NO:6 is α-amino butyric acid.

10. A method of delaying the recurrence of cancer following surgery, chemotherapy or radiation comprising administering the composition of claim 1 to a patient.

11. The method of claim 10, wherein said cancer is selected from the group consisting of:
   a. colon cancer;
   b. non-small cell lung cancer (NSCLC);
   c. breast cancer;
   d. ovarian cancer; and
   e. a cancer of the head and/or neck.

* * * * *

SEQUENCE LISTING

<160> NUMBER OF SEQ ID NOS: 43

<210> SEQ ID NO 1
<211> LENGTH: 13
<212> TYPE: PRT
<213> ORGANISM: Mus sp.
<220> FEATURE:
<221> NAME/KEY: MISC_FEATURE
<222> LOCATION: (1)..(1)
<223> OTHER INFORMATION: Ala is D-alanine.
<220> FEATURE:
<221> NAME/KEY: MISC_FEATURE

```
<222> LOCATION: (3)..(3)
<223> OTHER INFORMATION: Xaa is cyclohexylalanine.
<220> FEATURE:
<221> NAME/KEY: MISC_FEATURE
<222> LOCATION: (13)..(13)
<223> OTHER INFORMATION: Ala is D-alanine.

<400> SEQUENCE: 1

Ala Lys Xaa Val Ala Ala Trp Thr Leu Lys Ala Ala Ala
1               5                   10

<210> SEQ ID NO 2
<211> LENGTH: 9
<212> TYPE: PRT
<213> ORGANISM: Mus. sp

<400> SEQUENCE: 2

Arg Leu Leu Gln Glu Thr Glu Leu Val
1               5

<210> SEQ ID NO 3
<211> LENGTH: 10
<212> TYPE: PRT
<213> ORGANISM: Mus sp.

<400> SEQUENCE: 3

Tyr Leu Gln Leu Val Phe Gly Ile Glu Val
1               5                   10

<210> SEQ ID NO 4
<211> LENGTH: 9
<212> TYPE: PRT
<213> ORGANISM: Mus sp.

<400> SEQUENCE: 4

Leu Leu Thr Phe Trp Asn Pro Pro Val
1               5

<210> SEQ ID NO 5
<211> LENGTH: 9
<212> TYPE: PRT
<213> ORGANISM: Mus sp.

<400> SEQUENCE: 5

Ser Met Pro Pro Pro Gly Thr Arg Val
1               5

<210> SEQ ID NO 6
<211> LENGTH: 9
<212> TYPE: PRT
<213> ORGANISM: Mus sp.
<220> FEATURE:
<221> NAME/KEY: MISC_FEATURE
<222> LOCATION: (3)..(3)
<223> OTHER INFORMATION: Xaa is alpha-aminoisobutyric acid.

<400> SEQUENCE: 6

Lys Leu Xaa Pro Val Gln Leu Trp Val
1               5

<210> SEQ ID NO 7
<211> LENGTH: 9
<212> TYPE: PRT
<213> ORGANISM: Mus sp.

<400> SEQUENCE: 7

Lys Val Phe Gly Ser Leu Ala Phe Val
```

-continued

<210> SEQ ID NO 8
<211> LENGTH: 9
<212> TYPE: PRT
<213> ORGANISM: Mus sp.

<400> SEQUENCE: 8

Tyr Leu Ser Gly Ala Asp Leu Asn Leu
1               5

<210> SEQ ID NO 9
<211> LENGTH: 9
<212> TYPE: PRT
<213> ORGANISM: Mus sp.

<400> SEQUENCE: 9

Ile Met Ile Gly His Leu Val Gly Val
1               5

<210> SEQ ID NO 10
<211> LENGTH: 9
<212> TYPE: PRT
<213> ORGANISM: Mus sp.

<400> SEQUENCE: 10

Lys Val Ala Glu Ile Val His Phe Leu
1               5

<210> SEQ ID NO 11
<211> LENGTH: 702
<212> TYPE: PRT
<213> ORGANISM: Mus sp.

<400> SEQUENCE: 11

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn

-continued

```
                195                 200                 205
Asp Thr Ala Ser Tyr Lys Cys Glu Thr Gln Asn Pro Val Ser Ala Arg
210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620
```

```
Tyr Ser Trp Arg Ile Asn Gly Ile Pro Gln Gln His Thr Gln Val Leu
625                 630                 635                 640

Phe Ile Ala Lys Ile Thr Pro Asn Asn Gly Thr Tyr Ala Cys Phe
            645                 650                 655

Val Ser Asn Leu Ala Thr Gly Arg Asn Asn Ser Ile Val Lys Ser Ile
        660                 665                 670

Thr Val Ser Ala Ser Gly Thr Ser Pro Gly Leu Ser Ala Gly Ala Thr
        675                 680                 685

Val Gly Ile Met Ile Gly Val Leu Val Gly Val Ala Leu Ile
            690                 695                 700

<210> SEQ ID NO 12
<211> LENGTH: 1255
<212> TYPE: PRT
<213> ORGANISM: Mus sp.

<400> SEQUENCE: 12

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300
```

```
Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
        340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
515                 520                 525

Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735
```

```
Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
            805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
            850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
            885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
            1010                1015                1020

Leu Val Pro Gln Gln Gly Phe Phe Cys Pro Asp Pro Ala Pro Gly
            1025                1030                1035

Ala Gly Gly Met Val His His Arg His Arg Ser Ser Ser Thr Arg
            1040                1045                1050

Ser Gly Gly Gly Asp Leu Thr Leu Gly Leu Glu Pro Ser Glu Glu
            1055                1060                1065

Glu Ala Pro Arg Ser Pro Leu Ala Pro Ser Glu Gly Ala Gly Ser
            1070                1075                1080

Asp Val Phe Asp Gly Asp Leu Gly Met Gly Ala Ala Lys Gly Leu
            1085                1090                1095

Gln Ser Leu Pro Thr His Asp Pro Ser Pro Leu Gln Arg Tyr Ser
            1100                1105                1110

Glu Asp Pro Thr Val Pro Leu Pro Ser Glu Thr Asp Gly Tyr Val
            1115                1120                1125

Ala Pro Leu Thr Cys Ser Pro Gln Pro Glu Tyr Val Asn Gln Pro
            1130                1135                1140

Asp Val Arg Pro Gln Pro Pro Ser Pro Arg Glu Gly Pro Leu Pro
```

```
              1145                1150                1155

Ala  Ala  Arg  Pro  Ala  Gly  Ala  Thr  Leu  Glu  Arg  Pro  Lys  Thr  Leu
     1160                1165                1170

Ser  Pro  Gly  Lys  Asn  Gly  Val  Val  Lys  Asp  Val  Phe  Ala  Phe  Gly
     1175                1180                1185

Gly  Ala  Val  Glu  Asn  Pro  Glu  Tyr  Leu  Thr  Pro  Gln  Gly  Gly  Ala
     1190                1195                1200

Ala  Pro  Gln  Pro  His  Pro  Pro  Ala  Phe  Ser  Pro  Ala  Phe  Asp
     1205                1210                1215

Asn  Leu  Tyr  Tyr  Trp  Asp  Gln  Asp  Pro  Pro  Glu  Arg  Gly  Ala  Pro
     1220                1225                1230

Pro  Ser  Thr  Phe  Lys  Gly  Thr  Pro  Thr  Ala  Glu  Asn  Pro  Glu  Tyr
     1235                1240                1245

Leu  Gly  Leu  Asp  Val  Pro  Val
     1250                1255

<210> SEQ ID NO 13
<211> LENGTH: 314
<212> TYPE: PRT
<213> ORGANISM: Mus sp.

<400> SEQUENCE: 13

Met  Pro  Leu  Glu  Gln  Arg  Ser  Gln  His  Cys  Lys  Pro  Glu  Glu  Gly  Leu
1                    5                   10                  15

Glu  Ala  Arg  Gly  Glu  Ala  Leu  Gly  Leu  Val  Gly  Ala  Gln  Ala  Pro  Ala
                20                  25                  30

Thr  Glu  Glu  Gln  Gln  Thr  Ala  Ser  Ser  Ser  Thr  Leu  Val  Glu  Val
        35                  40                  45

Thr  Leu  Gly  Glu  Val  Pro  Ala  Ala  Asp  Ser  Pro  Ser  Pro  Pro  His  Ser
    50                  55                  60

Pro  Gln  Gly  Ala  Ser  Ser  Phe  Ser  Thr  Thr  Ile  Asn  Tyr  Thr  Leu  Trp
65                   70                  75                  80

Arg  Gln  Ser  Asp  Glu  Gly  Ser  Ser  Asn  Gln  Glu  Glu  Glu  Gly  Pro  Arg
                85                  90                  95

Met  Phe  Pro  Asp  Leu  Glu  Ser  Glu  Phe  Gln  Ala  Ala  Ile  Ser  Arg  Lys
                100                 105                 110

Met  Val  Glu  Leu  Val  His  Phe  Leu  Leu  Leu  Lys  Tyr  Arg  Ala  Arg  Glu
                115                 120                 125

Pro  Val  Thr  Lys  Ala  Glu  Met  Leu  Glu  Ser  Val  Leu  Arg  Asn  Cys  Gln
    130                 135                 140

Asp  Phe  Phe  Pro  Val  Ile  Phe  Ser  Lys  Ala  Ser  Glu  Tyr  Leu  Gln  Leu
145                  150                 155                 160

Val  Phe  Gly  Ile  Glu  Val  Val  Glu  Val  Val  Pro  Ile  Ser  His  Leu  Tyr
                165                 170                 175

Ile  Leu  Val  Thr  Cys  Leu  Gly  Leu  Ser  Tyr  Asp  Gly  Leu  Leu  Gly  Asp
                180                 185                 190

Asn  Gln  Val  Met  Pro  Lys  Thr  Gly  Leu  Leu  Ile  Ile  Val  Leu  Ala  Ile
                195                 200                 205

Ile  Ala  Ile  Glu  Gly  Asp  Cys  Ala  Pro  Glu  Glu  Lys  Ile  Trp  Glu  Glu
    210                 215                 220

Leu  Ser  Met  Leu  Glu  Val  Phe  Glu  Gly  Arg  Glu  Asp  Ser  Val  Phe  Ala
225                  230                 235                 240

His  Pro  Arg  Lys  Leu  Leu  Met  Gln  Asp  Leu  Val  Gln  Glu  Asn  Tyr  Leu
                245                 250                 255

Glu  Tyr  Arg  Gln  Val  Pro  Gly  Ser  Asp  Pro  Ala  Cys  Tyr  Glu  Phe  Leu
```

-continued

```
                            260                 265                 270
Trp Gly Pro Arg Ala Leu Ile Glu Thr Ser Tyr Val Lys Val Leu His
        275                 280                 285
His Thr Leu Lys Ile Gly Gly Glu Pro His Ile Ser Tyr Pro Pro Leu
        290                 295                 300
His Glu Arg Ala Leu Arg Glu Gly Glu Glu
305                 310

<210> SEQ ID NO 14
<211> LENGTH: 314
<212> TYPE: PRT
<213> ORGANISM: Mus sp.

<400> SEQUENCE: 14

Met Pro Leu Glu Gln Arg Ser Gln His Cys Lys Pro Glu Glu Gly Leu
1               5                   10                  15
Glu Ala Arg Gly Glu Ala Leu Gly Leu Val Gly Ala Gln Ala Pro Ala
            20                  25                  30
Thr Glu Glu Gln Glu Ala Ala Ser Ser Ser Thr Leu Val Glu Val
        35                  40                  45
Thr Leu Gly Glu Val Pro Ala Ala Glu Ser Pro Asp Pro Pro Gln Ser
    50                  55                  60
Pro Gln Gly Ala Ser Ser Leu Pro Thr Thr Met Asn Tyr Pro Leu Trp
65                  70                  75                  80
Ser Gln Ser Tyr Glu Asp Ser Ser Asn Gln Glu Glu Glu Gly Pro Ser
                85                  90                  95
Thr Phe Pro Asp Leu Glu Ser Glu Phe Gln Ala Ala Leu Ser Arg Lys
            100                 105                 110
Val Ala Glu Leu Val His Phe Leu Leu Leu Lys Tyr Arg Ala Arg Glu
        115                 120                 125
Pro Val Thr Lys Ala Glu Met Leu Gly Ser Val Val Gly Asn Trp Gln
    130                 135                 140
Tyr Phe Phe Pro Val Ile Phe Ser Lys Ala Ser Ser Ser Leu Gln Leu
145                 150                 155                 160
Val Phe Gly Ile Glu Leu Met Glu Val Asp Pro Ile Gly His Leu Tyr
                165                 170                 175
Ile Phe Ala Thr Cys Leu Gly Leu Ser Tyr Asp Gly Leu Leu Gly Asp
            180                 185                 190
Asn Gln Ile Met Pro Lys Ala Gly Leu Leu Ile Ile Val Leu Ala Ile
        195                 200                 205
Ile Ala Arg Glu Gly Asp Cys Ala Pro Glu Glu Lys Ile Trp Glu Glu
    210                 215                 220
Leu Ser Val Leu Glu Val Phe Glu Gly Arg Glu Asp Ser Ile Leu Gly
225                 230                 235                 240
Asp Pro Lys Lys Leu Leu Thr Gln His Phe Val Gln Glu Asn Tyr Leu
                245                 250                 255
Glu Tyr Arg Gln Val Pro Gly Ser Asp Pro Ala Cys Tyr Glu Phe Leu
            260                 265                 270
Trp Gly Pro Arg Ala Leu Val Glu Thr Ser Tyr Val Lys Val Leu His
        275                 280                 285
His Met Val Lys Ile Ser Gly Gly Pro His Ile Ser Tyr Pro Pro Leu
        290                 295                 300
His Glu Trp Val Leu Arg Glu Gly Glu Glu
305                 310
```

```
<210> SEQ ID NO 15
<211> LENGTH: 393
<212> TYPE: PRT
<213> ORGANISM: Mus sp.

<400> SEQUENCE: 15

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met Ala
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Pro Gln Pro Lys Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
```

385 390

```
<210> SEQ ID NO 16
<211> LENGTH: 212
<212> TYPE: PRT
<213> ORGANISM: Mus sp.

<400> SEQUENCE: 16
```

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

```
<210> SEQ ID NO 17
<211> LENGTH: 9
<212> TYPE: PRT
<213> ORGANISM: Mus sp.

<400> SEQUENCE: 17
```

Asp Leu Met Gly Tyr Ile Pro Leu Val
1               5

```
<210> SEQ ID NO 18
<211> LENGTH: 15
<212> TYPE: PRT
<213> ORGANISM: Mus sp.

<400> SEQUENCE: 18
```

Gly Tyr Lys Val Leu Val Leu Asn Pro Ser Val Ala Ala Thr Leu
1               5                   10                  15

```
<210> SEQ ID NO 19
<211> LENGTH: 13
<212> TYPE: PRT
<213> ORGANISM: Mus sp.
<220> FEATURE:
```

```
<221> NAME/KEY: MISC_FEATURE
<222> LOCATION: (1)..(1)
<223> OTHER INFORMATION: Ala is D-alanine.
<220> FEATURE:
<221> NAME/KEY: MISC_FEATURE
<222> LOCATION: (13)..(13)
<223> OTHER INFORMATION: Ala is D-alanine..

<400> SEQUENCE: 19

Ala Lys Phe Val Ala Ala Trp Thr Leu Lys Ala Ala Ala
1               5                   10

<210> SEQ ID NO 20
<211> LENGTH: 13
<212> TYPE: PRT
<213> ORGANISM: Mus sp.
<220> FEATURE:
<221> NAME/KEY: MISC_FEATURE
<222> LOCATION: (1)..(1)
<223> OTHER INFORMATION: Ala is D-alanine.
<220> FEATURE:
<221> NAME/KEY: MISC_FEATURE
<222> LOCATION: (13)..(13)
<223> OTHER INFORMATION: Ala is D-alanine.

<400> SEQUENCE: 20

Ala Lys Tyr Val Ala Ala Trp Thr Leu Lys Ala Ala Ala
1               5                   10

<210> SEQ ID NO 21
<211> LENGTH: 13
<212> TYPE: PRT
<213> ORGANISM: Mus sp.
<220> FEATURE:
<221> NAME/KEY: MISC_FEATURE
<222> LOCATION: (1)..(1)
<223> OTHER INFORMATION: Ala is D-alanine.
<220> FEATURE:
<221> NAME/KEY: MISC_FEATURE
<222> LOCATION: (13)..(13)
<223> OTHER INFORMATION: Ala is D-alanine.

<400> SEQUENCE: 21

Ala Lys Phe Val Ala Ala Tyr Thr Leu Lys Ala Ala Ala
1               5                   10

<210> SEQ ID NO 22
<211> LENGTH: 13
<212> TYPE: PRT
<213> ORGANISM: Mus sp.
<220> FEATURE:
<221> NAME/KEY: MISC_FEATURE
<222> LOCATION: (1)..(1)
<223> OTHER INFORMATION: Ala is D-alanine.
<220> FEATURE:
<221> NAME/KEY: MISC_FEATURE
<222> LOCATION: (3)..(3)
<223> OTHER INFORMATION: Xaa is cyclohexylalanine.
<220> FEATURE:
<221> NAME/KEY: MISC_FEATURE
<222> LOCATION: (13)..(13)
<223> OTHER INFORMATION: Ala is D-alanine.

<400> SEQUENCE: 22

Ala Lys Xaa Val Ala Ala Tyr Thr Leu Lys Ala Ala Ala
1               5                   10

<210> SEQ ID NO 23
<211> LENGTH: 13
<212> TYPE: PRT
<213> ORGANISM: Mus sp.
<220> FEATURE:
```

```
<221> NAME/KEY: MISC_FEATURE
<222> LOCATION: (1)..(1)
<223> OTHER INFORMATION: Ala is D-alanine.
<220> FEATURE:
<221> NAME/KEY: MISC_FEATURE
<222> LOCATION: (13)..(13)
<223> OTHER INFORMATION: Ala is D-alanine.

<400> SEQUENCE: 23

Ala Lys Tyr Val Ala Ala Tyr Thr Leu Lys Ala Ala Ala
1               5                   10

<210> SEQ ID NO 24
<211> LENGTH: 13
<212> TYPE: PRT
<213> ORGANISM: Mus sp.
<220> FEATURE:
<221> NAME/KEY: MISC_FEATURE
<222> LOCATION: (1)..(1)
<223> OTHER INFORMATION: Ala is D-alanine.
<220> FEATURE:
<221> NAME/KEY: MISC_FEATURE
<222> LOCATION: (13)..(13)
<223> OTHER INFORMATION: Ala is D-alanine.

<400> SEQUENCE: 24

Ala Lys Phe Val Ala Ala His Thr Leu Lys Ala Ala Ala
1               5                   10

<210> SEQ ID NO 25
<211> LENGTH: 13
<212> TYPE: PRT
<213> ORGANISM: Mus sp.
<220> FEATURE:
<221> NAME/KEY: MISC_FEATURE
<222> LOCATION: (1)..(1)
<223> OTHER INFORMATION: Ala is D-alanine.
<220> FEATURE:
<221> NAME/KEY: MISC_FEATURE
<222> LOCATION: (3)..(3)
<223> OTHER INFORMATION: Xaa is cyclohexylalanine.
<220> FEATURE:
<221> NAME/KEY: MISC_FEATURE
<222> LOCATION: (13)..(13)
<223> OTHER INFORMATION: Ala is D-alanine.

<400> SEQUENCE: 25

Ala Lys Xaa Val Ala Ala His Thr Leu Lys Ala Ala Ala
1               5                   10

<210> SEQ ID NO 26
<211> LENGTH: 13
<212> TYPE: PRT
<213> ORGANISM: Mus sp.
<220> FEATURE:
<221> NAME/KEY: MISC_FEATURE
<222> LOCATION: (1)..(1)
<223> OTHER INFORMATION: Ala is  D-alanine.
<220> FEATURE:
<221> NAME/KEY: MISC_FEATURE
<222> LOCATION: (13)..(13)
<223> OTHER INFORMATION: Ala is D-alanine.

<400> SEQUENCE: 26

Ala Lys Tyr Val Ala Ala His Thr Leu Lys Ala Ala Ala
1               5                   10

<210> SEQ ID NO 27
<211> LENGTH: 13
<212> TYPE: PRT
<213> ORGANISM: Mus sp.
<220> FEATURE:
```

```
<221> NAME/KEY: MISC_FEATURE
<222> LOCATION: (1)..(1)
<223> OTHER INFORMATION: Ala is D-alanine.
<220> FEATURE:
<221> NAME/KEY: MISC_FEATURE
<222> LOCATION: (13)..(13)
<223> OTHER INFORMATION: Ala is D-alanine..

<400> SEQUENCE: 27

Ala Lys Phe Val Ala Ala Asn Thr Leu Lys Ala Ala Ala
1               5                   10

<210> SEQ ID NO 28
<211> LENGTH: 13
<212> TYPE: PRT
<213> ORGANISM: Mus sp.
<220> FEATURE:
<221> NAME/KEY: MISC_FEATURE
<222> LOCATION: (1)..(1)
<223> OTHER INFORMATION: Ala is D-alanine.
<220> FEATURE:
<221> NAME/KEY: MISC_FEATURE
<222> LOCATION: (3)..(3)
<223> OTHER INFORMATION: Xaa is cyclohexylalanine.
<220> FEATURE:
<221> NAME/KEY: MISC_FEATURE
<222> LOCATION: (13)..(13)
<223> OTHER INFORMATION: Ala is D-alanine.

<400> SEQUENCE: 28

Ala Lys Xaa Val Ala Ala Asn Thr Leu Lys Ala Ala Ala
1               5                   10

<210> SEQ ID NO 29
<211> LENGTH: 13
<212> TYPE: PRT
<213> ORGANISM: Mus sp.
<220> FEATURE:
<221> NAME/KEY: MISC_FEATURE
<222> LOCATION: (1)..(1)
<223> OTHER INFORMATION: Ala is D-alanine.
<220> FEATURE:
<221> NAME/KEY: MISC_FEATURE
<222> LOCATION: (13)..(13)
<223> OTHER INFORMATION: Ala is D-alanine.

<400> SEQUENCE: 29

Ala Lys Tyr Val Ala Ala Asn Thr Leu Lys Ala Ala Ala
1               5                   10

<210> SEQ ID NO 30
<211> LENGTH: 13
<212> TYPE: PRT
<213> ORGANISM: Mus sp.
<220> FEATURE:
<221> NAME/KEY: MISC_FEATURE
<222> LOCATION: (3)..(3)
<223> OTHER INFORMATION: Xaa is cyclohexylalanine.

<400> SEQUENCE: 30

Ala Lys Xaa Val Ala Ala Trp Thr Leu Lys Ala Ala Ala
1               5                   10

<210> SEQ ID NO 31
<211> LENGTH: 13
<212> TYPE: PRT
<213> ORGANISM: Mus sp.

<400> SEQUENCE: 31

Ala Lys Phe Val Ala Ala Trp Thr Leu Lys Ala Ala Ala
1               5                   10
```

```
<210> SEQ ID NO 32
<211> LENGTH: 13
<212> TYPE: PRT
<213> ORGANISM: alternative PADRE peptide

<400> SEQUENCE: 32

Ala Lys Tyr Val Ala Ala Trp Thr Leu Lys Ala Ala Ala
1               5                   10

<210> SEQ ID NO 33
<211> LENGTH: 13
<212> TYPE: PRT
<213> ORGANISM: Mus sp.

<400> SEQUENCE: 33

Ala Lys Phe Val Ala Ala Tyr Thr Leu Lys Ala Ala Ala
1               5                   10

<210> SEQ ID NO 34
<211> LENGTH: 13
<212> TYPE: PRT
<213> ORGANISM: Mus sp.
<220> FEATURE:
<221> NAME/KEY: MISC_FEATURE
<222> LOCATION: (3)..(3)
<223> OTHER INFORMATION: Xaa is cyclohexylalanine.

<400> SEQUENCE: 34

Ala Lys Xaa Val Ala Ala Tyr Thr Leu Lys Ala Ala Ala
1               5                   10

<210> SEQ ID NO 35
<211> LENGTH: 13
<212> TYPE: PRT
<213> ORGANISM: Mus sp.

<400> SEQUENCE: 35

Ala Lys Tyr Val Ala Ala Tyr Thr Leu Lys Ala Ala Ala
1               5                   10

<210> SEQ ID NO 36
<211> LENGTH: 13
<212> TYPE: PRT
<213> ORGANISM: Mus sp.

<400> SEQUENCE: 36

Ala Lys Phe Val Ala Ala His Thr Leu Lys Ala Ala Ala
1               5                   10

<210> SEQ ID NO 37
<211> LENGTH: 13
<212> TYPE: PRT
<213> ORGANISM: Mus sp.
<220> FEATURE:
<221> NAME/KEY: MISC_FEATURE
<222> LOCATION: (3)..(3)
<223> OTHER INFORMATION: Xaa is cyclohexylalanine.

<400> SEQUENCE: 37

Ala Lys Xaa Val Ala Ala His Thr Leu Lys Ala Ala Ala
1               5                   10

<210> SEQ ID NO 38
<211> LENGTH: 13
<212> TYPE: PRT
<213> ORGANISM: Mus sp.
```

```
<400> SEQUENCE: 38

Ala Lys Tyr Val Ala Ala His Thr Leu Lys Ala Ala Ala
1               5                   10

<210> SEQ ID NO 39
<211> LENGTH: 13
<212> TYPE: PRT
<213> ORGANISM: Mus sp.

<400> SEQUENCE: 39

Ala Lys Phe Val Ala Ala Asn Thr Leu Lys Ala Ala Ala
1               5                   10

<210> SEQ ID NO 40
<211> LENGTH: 13
<212> TYPE: PRT
<213> ORGANISM: Mus sp.
<220> FEATURE:
<221> NAME/KEY: MISC_FEATURE
<222> LOCATION: (3)..(3)
<223> OTHER INFORMATION: Xaa is cyclohexylalanine.

<400> SEQUENCE: 40

Ala Lys Xaa Val Ala Ala Asn Thr Leu Lys Ala Ala Ala
1               5                   10

<210> SEQ ID NO 41
<211> LENGTH: 13
<212> TYPE: PRT
<213> ORGANISM: Mus sp.

<400> SEQUENCE: 41

Ala Lys Tyr Val Ala Ala Asn Thr Leu Lys Ala Ala Ala
1               5                   10

<210> SEQ ID NO 42
<211> LENGTH: 13
<212> TYPE: PRT
<213> ORGANISM: Mus sp.
<220> FEATURE:
<221> NAME/KEY: MISC_FEATURE
<222> LOCATION: (1)..(1)
<223> OTHER INFORMATION: Ala is either D-alanine or L-alanine.
<220> FEATURE:
<221> NAME/KEY: MISC_FEATURE
<222> LOCATION: (3)..(3)
<223> OTHER INFORMATION: Xaa is either cyclohexylalanine, phenylalanine,
      or tyrosine.
<220> FEATURE:
<221> NAME/KEY: MISC_FEATURE
<222> LOCATION: (7)..(7)
<223> OTHER INFORMATION: Xaa is either tryptophan, tyrosine, histidine,
      or asparagine.
<220> FEATURE:
<221> NAME/KEY: MISC_FEATURE
<222> LOCATION: (13)..(13)
<223> OTHER INFORMATION: Ala is either D-alanine or L-alanine.

<400> SEQUENCE: 42

Ala Lys Xaa Val Ala Ala Xaa Thr Leu Lys Ala Ala Ala
1               5                   10

<210> SEQ ID NO 43
<211> LENGTH: 13
<212> TYPE: PRT
<213> ORGANISM: Mus sp.
<220> FEATURE:
<221> NAME/KEY: MISC_FEATURE
<222> LOCATION: (1)..(1)
```

```
<223> OTHER INFORMATION: Ala is D-alanine.
<220> FEATURE:
<221> NAME/KEY: MISC_FEATURE
<222> LOCATION: (3)..(3)
<223> OTHER INFORMATION: Xaa is cyclohexylalanine.
<220> FEATURE:
<221> NAME/KEY: MISC_FEATURE
<222> LOCATION: (13)..(13)
<223> OTHER INFORMATION: Ala is amidated D-alanine.

<400> SEQUENCE: 43

Ala Lys Xaa Val Ala Ala Trp Thr Leu Lys Ala Ala Ala
1               5                   10
```